(12) United States Patent
Lu et al.

(10) Patent No.: US 10,945,954 B2
(45) Date of Patent: *Mar. 16, 2021

(54) ARRDC1-MEDIATED MICROVESICLES (ARMMS) AND USES THEREOF

(71) Applicants: President and Fellows of Harvard College, Cambridge, MA (US); The Board of Trustees of the Leland Stanford Junior University, Stanford, CA (US)

(72) Inventors: Quan Lu, Newton, MA (US); Joseph F. Nabhan, Cambridge, MA (US); Stanley N. Cohen, Palo Alto, CA (US)

(73) Assignees: President and Fellows of Harvard College, Cambridge, MA (US); The Board of Trustees of the Leland Stanford Junior University, Stanford, CA (US)

( * ) Notice: Subject to any disclaimer, the term of this patent is extended or adjusted under 35 U.S.C. 154(b) by 602 days.

This patent is subject to a terminal disclaimer.

(21) Appl. No.: 15/669,720

(22) Filed: Aug. 4, 2017

(65) Prior Publication Data
US 2018/0055768 A1 Mar. 1, 2018

Related U.S. Application Data

(62) Division of application No. 14/376,967, filed as application No. PCT/US2013/024839 on Feb. 6, 2013, now Pat. No. 9,737,480.

(60) Provisional application No. 61/595,416, filed on Feb. 6, 2012.

(51) Int. Cl.
| A61K 9/107 | (2006.01) |
| C07K 14/47 | (2006.01) |
| A61K 47/42 | (2017.01) |
| G01N 33/68 | (2006.01) |

(52) U.S. Cl.
CPC .............. *A61K 9/107* (2013.01); *A61K 47/42* (2013.01); *C07K 14/47* (2013.01); *G01N 33/6893* (2013.01); *C07K 2319/00* (2013.01); *C07K 2319/70* (2013.01); *G01N 2333/47* (2013.01); *G01N 2333/726* (2013.01)

(58) Field of Classification Search
CPC combination set(s) only.
See application file for complete search history.

(56) References Cited

U.S. PATENT DOCUMENTS

| 4,880,635 | A | 11/1989 | Janoff et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 5,270,163 | A | 12/1993 | Gold et al. |
| 5,449,639 | A | 9/1995 | Wei et al. |
| 5,475,096 | A | 12/1995 | Gold et al. |
| 5,496,938 | A | 3/1996 | Gold et al. |
| 5,595,887 | A | 1/1997 | Coolidge et al. |
| 5,767,099 | A | 6/1998 | Harris et al. |
| 5,780,053 | A | 7/1998 | Ashley et al. |
| 5,817,785 | A | 10/1998 | Gold et al. |
| 5,830,430 | A | 11/1998 | Unger et al. |
| 5,851,548 | A | 12/1998 | Dattagupta et al. |
| 5,855,910 | A | 1/1999 | Ashley et al. |
| 5,861,254 | A | 1/1999 | Schneider et al. |
| 5,958,691 | A | 9/1999 | Pieken et al. |
| 5,962,219 | A | 10/1999 | Gold et al. |
| 6,013,443 | A | 1/2000 | Heilig et al. |
| 6,030,776 | A | 2/2000 | Eaton et al. |
| 6,083,696 | A | 7/2000 | Biesecker et al. |
| 6,110,900 | A | 8/2000 | Gold et al. |
| 6,127,119 | A | 10/2000 | Stephens et al. |
| 6,147,204 | A | 11/2000 | Gold et al. |
| 6,376,019 | B1 | 4/2002 | Leung |
| 7,314,923 | B2 | 1/2008 | Kaneko et al. |
| 7,335,765 | B2 | 2/2008 | Kaneko et al. |
| 7,399,845 | B2 | 7/2008 | Seth et al. |
| 7,569,686 | B1 | 8/2009 | Bhat et al. |
| 7,741,457 | B2 | 6/2010 | Seth et al. |
| 7,816,333 | B2 | 10/2010 | Seth et al. |

(Continued)

FOREIGN PATENT DOCUMENTS

| WO | WO 2001/038547 A2 | 5/2001 |
| WO | WO 2011/127219 A1 | 10/2011 |

(Continued)

OTHER PUBLICATIONS

International Search Report and Written Opinion dated Feb. 13, 2018 in connection with Application No. PCT/US/2017/54912.
International Preliminary Report on Patentability dated Apr. 18, 2019 in connection with Application No. PCT/US/2017/54912.
Xu et al., Extracellular vesicle isolation and characterization: toward clinical application. J Clin Invest. Apr. 1, 2016;126(4):1152-62. doi: 10.1172/JCI81129. Epub Apr. 1, 2016.
International Search Report and Written Opinion for PCT/US2013/024839, dated May 28, 2013.

(Continued)

*Primary Examiner* — James D Schultz
(74) *Attorney, Agent, or Firm* — Wolf, Greenfield & Sacks, P.C.

(57) ABSTRACT

The invention provide isolated arrestin domain-containing protein 1 (ARRDC1)-mediated microvesicles (ARMMs). Methods for generating and for isolating ARMMs are also provided herein. ARMMs can be used to deliver agents, for example, nucleic acids (e.g., siRNAs, microRNAs, lincRNAs), proteins (e.g., transcription factors, chromatin modulators, kinases, phosphorylases, or recombinases), or small molecules to target cells in vitro and in vivo, and methods for such ARMM-mediated delivery are provided herein. Diagnostic and therapeutic methods using ARMMs are also described herein.

20 Claims, 16 Drawing Sheets

Specification includes a Sequence Listing.

(56) References Cited

U.S. PATENT DOCUMENTS

| | | |
|---|---|---|
| 8,022,193 B2 | 9/2011 | Seth et al. |
| 8,795,965 B2 | 8/2014 | Zhang |
| 9,061,043 B2 | 6/2015 | Sullenger et al. |
| 9,737,480 B2 | 8/2017 | Lu et al. |
| 9,816,080 B2 | 11/2017 | Lu et al. |
| 10,260,055 B2 | 4/2019 | Lu et al. |
| 2003/0083294 A1 | 5/2003 | Sullenger et al. |
| 2003/0175703 A1 | 9/2003 | Sullenger et al. |
| 2006/0188560 A1 | 8/2006 | Cheresh et al. |
| 2011/0009471 A1 | 1/2011 | Kaneko et al. |
| 2011/0053157 A1 | 3/2011 | Skog et al. |
| 2011/0151460 A1 | 6/2011 | Klass et al. |
| 2014/0273226 A1 | 9/2014 | Wu |
| 2014/0364588 A1 | 12/2014 | Haugwitz et al. |
| 2015/0037421 A1 | 2/2015 | Lu et al. |
| 2015/0071903 A1 | 3/2015 | Liu |
| 2015/0093433 A1 | 4/2015 | Leonard et al. |
| 2015/0315252 A1 | 11/2015 | Haugwitz et al. |
| 2016/0201089 A1 | 7/2016 | Gersbach et al. |
| 2016/0206566 A1 | 7/2016 | Lu et al. |
| 2018/0119118 A1 | 5/2018 | Lu et al. |
| 2019/0241876 A1 | 8/2019 | Lu et al. |

FOREIGN PATENT DOCUMENTS

| | | |
|---|---|---|
| WO | WO 2013/119602 A1 | 8/2013 |
| WO | WO 2014/093655 A2 | 6/2014 |
| WO | WO 2014/165825 A2 | 10/2014 |
| WO | WO 2015/002956 A1 | 1/2015 |
| WO | WO 2015/042308 A2 | 3/2015 |

OTHER PUBLICATIONS

International Preliminary Report on Patentability for PCT/US2013/024839, dated Aug. 21, 2014.
Invitation to Pay Additional Fees for PCT/US/2017/54912, dated Dec. 12, 2017.
Genbank Submission; NIH/NCBI, Accession No. NC_015683. Trost et al., Jul 6, 2013.
Genbank Submission; NIH/NCBI, Accession No. NC_016782. Trost et al., Jun 11, 2013.
Genbank Submission; NIH/NCBI, Accession No. NC_016786. Trost et al., Aug. 28, 2013.
Genbank Submission; NIH/NCBI, Accession No. NC_017053. Fittipaldi et al., Jul. 6, 2013.
Genbank Submission; NIH/NCBI, Accession No. NC_017317. Trost et al., Jun. 11, 2013.
Genbank Submission; NIH/NCBI, Accession No. NC_017861. Heidelberg et al., Jun. 11, 2013.
Genbank Submission; NIH/NCBI, Accession No. NC_018010. Lucas et al., Jun. 11, 2013.
Genbank Submission; NIH/NCBI, Accession No. NC_018721. Feng et al., Jun. 11, 2013.
Genbank Submission; NIH/NCBI, Accession No. NC_021284. Ku et al., Jul. 12, 2013.
Genbank Submission; NIH/NCBI, Accession No. NC_021314. Zhang et al., Jul. 15, 2013.
Genbank Submission; NIH/NCBI, Accession No. NC_021846. Lo et al., Jul. 22, 2013.
Genbank Submission; NIH/NCBI, Accession No. NM_015277.5. Wilkars et al., Aug. 16, 2014. 9 pages.
Genbank Submission; NIH/NCBI, Accession No. NP_001155957. Skarnes et al., Feb. 26, 2014.
Genbank Submission; NIH/NCBI, Accession No. NP_006283. Rush et al., May 4, 2014.
Genbank Submission; NIH/NCBI, Accession No. NP_056092.2. Wilkars et al., Aug. 16, 2014. 3 pages.
Genbank Submission; NIH/NCBI, Accession No. NP_068684. Gunn et al., Feb. 26, 2014.
Genbank Submission; NIH/NCBI, Accession No. NP_472073. Glaser et al., Jun. 27, 2013.
Genbank Submission; NIH/NCBI, Accession No. NP_689498. Puca et al., Mar. 22, 2014.
Genbank Submission; NIH/NCBI, Accession No. NP_848495. Skarnes et al., Feb. 26, 2014.
Genbank Submission; NIH/NCBI, Accession No. NP_853659. Leithe et al., Aug. 10, 2014.
Genbank Submission; NIH/NCBI, Accession No. YP_002342100. Bernardini et al., Jun. 10, 2013.
Genbank Submission; NIH/NCBI, Accession No. YP_002344900. Gundogdu et al., Jul. 11, 2013.
Genbank Submission; NIH/NCBI, Accession No. YP_820832. Makarova et al., Aug. 27, 2013.
Uniprot Submission; UniProt, Accession No. O00308. Last modified Oct. 29, 2014, version 141.
Uniprot Submission; UniProt, Accession No. P46934. Last modified Oct. 29, 2014, version 152.
Uniprot Submission; UniProt, Accession No. Q76N89. Last modified Oct. 29, 2014, version 95.
Uniprot Submission; UniProt, Accession No. Q96J02. Last modified Oct. 29, 2014, version 129.
Uniprot Submission; UniProt, Accession No. Q9H0M0. Last modified Oct. 29, 2014, version 136.
Uniprot Submission; UniProt, Accession No. Q9HAU4. Last modified Oct. 29, 2014, version 143.
Uniprot Submission; UniProt, Accession No. Q9HCE7.Last modified Oct. 29, 2014, version 136.
Uniprot Submission; UniProt, Accession No. Q9P2P5. Last modified Oct. 29, 2014, version 105.
Altschul et al., Basic local alignment search tool. J Mol Biol. Oct. 5, 1990;215(3):403-10.
Alvarez, On the origins of arrestin and rhodopsin. BMC Evol Biol. Jul. 29, 2008;8:222. doi: 10.1186/1471-2148-8-222.
Andriole et al., Mortality results from a randomized prostate-cancer screening trial. N Engl J Med. Mar. 26, 2009;360(13):1310-9. doi: 10.1056/NEJMoa0810696. Epub Mar. 18, 2009. Erratum in: N Engl J Med. Apr. 23, 2009;360(17):1797.
Babst et al., Mammalian tumor susceptibility gene 101 (TSG101) and the yeast homologue, Vps23p, both function in late endosomal trafficking. Traffic. Mar. 2000;1(3):248-58.
Babst, A protein's final ESCRT. Traffic. Jan. 2005;6(1):2-9.
Bache et al., Hrs regulates multivesicular body formation via ESCRT recruitment to endosomes. J Cell Biol. Aug. 4, 2003;162(3):435-42.
Bieniasz, The cell biology of HIV-1 virion genesis. Cell Host Microbe. Jun. 18, 2009;5(6):550-8. doi: 10.1016/j.chom.2009.05.015.
Bork et al., The WW domain: a signaling site in dystrophin? Trends Biochem Sci. Dec. 1994;19(12):531-3.
Brown et al., Serine recombinases as tools for genome engineering. Methods. Apr. 2011;53(4):372-9. doi: 10.1016/j.ymeth.2010.12.031. Epub Dec. 30, 2010.
Carillo et al., The multiple sequence alignment problem in biology. SIAM J Appl Math. 1988;48:1073-1082.
Carroll, Progress and prospects: zinc-finger nucleases as gene therapy agents. Gene Ther. Nov. 2008;15(22):1463-8. doi: 10.1038/gt.2008.145. Epub Sep. 11, 2008.
Chantry, WWP2 ubiquitin ligase and its isoforms: new biological insight and promising disease targets. Cell Cycle. Aug. 1, 2011;10(15):2437-9. Epub Aug. 1, 2011.
Chavez et al., Therapeutic applications of the ΦC31 integrase system. Curr Gene Ther. Oct. 2011;11(5):375-81.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cong et al., Multiplex genome engineering using CRISPR/Cas systems. Science. Feb. 15, 2013;339(6121):819-23. doi: 10.1126/science.1231143. Epub Jan. 3, 2013.
Cramer et al., Ovarian cancer biomarker performance in prostate, lung, colorectal, and ovarian cancer screening trial specimens. Cancer Prev Res (Phila). Mar. 2011;4(3):365-74. doi: 10.1158/1940-6207.CAPR-10-0195.

(56) References Cited

OTHER PUBLICATIONS

Deltcheva et al., CRISPR RNA maturation by trans-encoded small RNA and host factor RNase III. Nature. Mar. 31, 2011;471(7340):602-7. doi: 10.1038/nature09886.
Demirov et al., Overexpression of the N-terminal domain of TSG101 inhibits HIV-1 budding by blocking late domain function. Proc Natl Acad Sci U S A. Jan. 22, 2002;99(2):955-60.
Demirov et al., Retrovirus budding. Virus Res. Dec. 2004;106(2):87-102.
Denzer et al., Exosome: from internal vesicle of the multivesicular body to intercellular signaling device. J Cell Sci. Oct. 2000;113 Pt 19:3365-74.
Devereux et al., A comprehensive set of sequence analysis programs for the VAX. Nucleic Acids Res. Jan. 11, 1984;12(1 Pt 1):387-95.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Draheim et al., ARRDC3 suppresses breast cancer progression by negatively regulating integrin beta4. Oncogene. Sep. 9, 2010;29(36):5032-47. doi: 10.1038/onc.2010.250. Epub Jul. 5, 2010.
Esvelt et al., Genome-scale engineering for systems and synthetic biology. Mol Syst Biol. 2013;9:641. doi: 10.1038/msb.2012.66.
Ferretti et al., Complete genome sequence of an M1 strain of *Streptococcus pyogenes*. Proc Natl Acad Sci U S A Apr. 10, 2001;98(8):4658-63.
Freed et al., The cell biology of HIV-1 and other retroviruses. Retrovirology. Nov. 3, 2006;3:77.
Fujii et al., Beyond Tsg101: the role of Alix in 'ESCRTing' HIV-1. Nat Rev Microbiol. Dec. 2007;5(12):912-6.
Garrus et al., Tsg101 and the vacuolar protein sorting pathway are essential for HIV-1 budding. Cell. Oct. 5, 2001;107(1):55-65.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Gottlinger et al., Effect of mutations affecting the p6 gag protein on human immunodeficiency virus particle release. Proc Natl Acad Sci U S A. Apr. 15, 1991;88(8):3195-9.
Groth et al., Phage integrases: biology and applications. J Mol Biol. Jan. 16, 2004;335(3):667-78.
Hammarstedt et al., Passive and active inclusion of host proteins in human immunodeficiency virus type 1 gag particles during budding at the plasma membrane. J Virol. Jun. 2004;78(11):5686-97.
Henne et al., The ESRCT pathway. Dev Cell. Jul. 19, 2011;21(1):77-91. doi: 10.1016/j.devcel.2011.05.015.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Huang et al., p6Gag is required for particle production from full-length human immunodeficiency virus type 1 molecular clones expressing protease. J Virol. Nov. 1995;69(11):6810-8.
Hurley et al., Membrane budding. Cell. Dec. 10, 2010;143(6):875-87. doi: 10.1016/j.cell.2010.11.030.
Hurley et al., Molecular mechanisms of ubiquitin-dependent membrane traffic. Annu Rev Biophys. 2011;40:119-42. doi: 10.1146/annurev-biophys-042910-155404.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012.
Katzmann et al., Receptor downregulation and multivesicular-body sorting. Nat Rev Mol Cell Biol. Dec. 2002;3(12):893-905.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Komada et al., Hrs, a FYVE finger protein localized to early endosomes, is implicated in vesicular traffic and required for ventral folding morphogenesis. Genes Dev. Jun. 1, 1999;13(11):1475-85.
Kosaka et al., Secretory mechanisms and intercellular transfer of microRNAs in living cells. J Biol Chem. Jun. 4, 2010;285(23):17442-52.
Kuo et al., ARRDC1 as a mediator of microvesicle budding. PNAS. Mar. 2012;109(11):4025-4026.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Lu et al., TSG101 interaction with HRS mediates endosomal trafficking and receptor down-regulation. PNAS. Jun. 24, 2003;100(13):7626-31. Epub Jun. 11, 2003.
Mali et al., RNA-guided human genome engineering via Cas9. Science. Feb. 15, 2013;339(6121):823-6. doi: 10.1126/science.1232033. Epub Jan. 3, 2013.
Mani et al., Design, engineering, and characterization of zinc finger nucleases. Biochem Biophys Res Commun. Sep. 23, 2005;335(2):447-57.
Martin-Serrano et al., HIV-1 and Ebola virus encode small peptide motifs that recruit Tsg101 to sites of particle assembly to facilitate egress. Nat Med. Dec. 2001;7(12):1313-9.
Martin-Serrano et al., Host factors involved in retroviral budding and release. Nat Rev Microbiol. Jun. 16, 2011;9(7):519-31. doi: 10.1038/nrmicro2596.
Martin-Serrano et al., Role of ESCRT-I in retroviral budding. J Virol. Apr. 2003;77(8):4794-804.
Mathivanan et al., Proteomics analysis of A33 immunoaffinity-purified exosomes released from the human colon tumor cell line LIM1215 reveals a tissue-specific protein signature. Mol Cell Proteomics. Feb. 2010;9(2):197-208. doi: 10.1074/mcp.M900152-MCP200. Epub Oct. 16, 2009.
Morita et al., Retrovirus budding. Annu Rev Cell Dev Biol. 2004;20:395-425.
Murphy, Phage recombinases and their applications. Adv Virus Res. 2012;83:367-414. doi: 10.1016/B978-0-12-394438-2.00008-6.
Myers et al., Optimal alignments in linear space. Comput Appl Biosci. 1988;4(1):11-17. doi: 10.1093/bioinformatics/4.1.11.
Nabhan et al., Arrestin domain-containing protein 3 recruits the NEDD4 E3 ligase to mediate ubiquitination of the beta2-adrenergic receptor. EMBO Rep. Aug. 2010;11(8):605-11. doi: 10.1038/embor.2010.80. Epub Jun. 18, 2010.
Nabhan et al., Formation and release of arrestin domain-containing protein 1-mediated microvesicles (ARMMs) at plasma membrane by recruitment of TSG101 protein. Proc Natl Acad Sci U S A. Mar. 13, 2012;109(11):4146-51. doi: 10.1073/pnas.1200448109. Epub Feb. 6, 2012.
Nichols et al., Formation of pluripotent stem cells in the mammalian embryo depends on the POU transcription factor Oct4. Cell. Oct. 30, 1998;95(3):379-91.

(56) References Cited

OTHER PUBLICATIONS

Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.

Ono et al., Cell-type-dependent targeting of human immunodeficiency virus type 1 assembly to the plasma membrane and the multivesicular body. J Virol. Feb. 2004;78(3):1552-63.

Ono et al., Relationship between human immunodeficiency virus type 1 Gag multimerization and membrane binding. J Virol. Jun. 2000;74(11):5142-50.

Pennisi, The CRISPR craze. Science. Aug. 23, 2013;341(6148):833-6. doi: 10.1126/science.341.6148.833.

Perbal, Practical Guide to Molecular Cloining. John Wiley & Sons, Inc. 1984.

Perez et al., Establishment of HIV-1 resistance in CD4+ T cells by genome editing using zinc-finger nucleases. Nat Biotechnol. Jul. 2008;26(7):808-16. doi: 10.1038/nbt1410. Epub Jun. 29, 2008.

Pisitkun et al., Identification and proteomic profiling of exosomes in human urine. Proc Natl Acad Sci U S A. Sep. 7, 2004;101(36):13368-73. Epub Aug. 23, 2004.

Pornillos et al., HIV Gag mimics the Tsg101-recruiting activity of the human Hrs protein. J Cell Biol. Aug. 4, 2003;162(3):425-34.

Pornillos et al., Structure and functional interactions of the Tsg101 UEV domain. EMBO J. May 15, 2002;21(10):2397-406.

Pornillos et al., Structure of the Tsg101 UEV domain in complex with the PTAP motif of the HIV-1 p6 protein. Nat Struct Biol. Nov. 2002;9(11):812-7.

Properzi et al., Exosomes: the future of biomarkers in medicine. Biomark Med. Oct. 2013;7(5):769-78.

Qi et al., Repurposing CRISPR as an RNA-guided platform for sequence-specific control of gene expression. Cell. Feb. 28, 2013;152(5):1173-83. doi: 10.1016/j.cell.2013.02.022.

Rauch et al., Multiple interactions between the ESCRT machinery and arrestin-related proteins: implications for PPXY-dependent budding. J Virol. Apr. 2011;85(7):3546-56. doi: 10.1128/Jvi.02045-10. Epub Dec. 29, 2010.

Razi et al., Distinct roles for Tsg101 and Hrs in multivesicular body formation and inward vesiculation. Mol Biol Cell. Aug. 2006;17(8):3469-83. Epub May 17, 2006.

Rotin et al., Physiological functions of the HECT family of ubiquitin ligases. Nat Rev Mol Cell Biol. Jun. 2009;10(6):398-409. doi: 10.1038/nrm2690. Epub May 13, 2009.

Roy et al., Candidate prognostic markers in breast cancer: focus on extracellular proteases and their inhibitors. Breast Cancer (Dove Med Press). Jul. 3, 2014;6:81-91. doi: 10.2147/BCTT.S46020.

Schorey et al., Exosome function: from tumor immunology to pathogen biology. Traffic. Jun. 2008;9(6):871-81. doi: 10.1111/j.1600-0854.2008.00734.x. Epub Mar. 6, 2008.

Schröder et al., Screening and prostate-cancer mortality in a randomized European study. N Engl J Med. Mar. 26, 2009;360(13):1320-8. doi: 10.1056/NEJMoa0810084. Epub Mar. 18, 2009.

Scott et al., Structural and mechanistic studies of VPS4 proteins. EMBO J. Oct. 19, 2005;24(20):3658-69. Epub Sep. 29, 2005.

Sen et al., Cellular unfolded protein response against viruses used in gene therapy. Front Microbiol. May 26, 2014;5:250. doi: 10.3389/fmicb.2014.00250. eCollection 2014.

Skog et al., Glioblastoma microvesicles transport Rna and proteins that promote tumour growth and provide diagnostic biomarkers. Nat Cell Biol. Dec. 2008;10(12):1470-6. doi: 10.1038/ncb1800. Epub Nov. 16, 2008.

Sundquist et al., Ubiquitin recognition by the human TSG101 protein. Mol Cell. Mar. 26, 2004;13(6):783-9.

Thery et al., Exosomes: composition, biogenesis and function. Nat Rev Immunol. Aug. 2002;2(8):569-79.

Thery et al., Membrane vesicles as conveyors of immune responses. Nat Rev Immunol. Aug. 2009;9(8):581-93. doi: 10.1038/nri2567. Epub Jun. 5, 2009.

Turan et al., Site-specific recombinases: from tag-and-target- to tag-and-exchange-based genomic modifications. Faseb J. Dec. 2011;25(12):4088-107. doi: 10.1096/fj.11-186940. Epub Sep. 2, 2011.

Tykodi, PD-1 as an emerging therapeutic target in renal cell carcinoma: current evidence. Onco Targets Ther. Jul. 25, 2014;7:1349-59. doi: 10.2147/OTT.S48443.

Urnov et al., Highly efficient endogenous human gene correction using designed zinc-finger nucleases. Nature. Jun. 2, 2005;435(7042):646-51. Epub Apr. 3, 2005.

Valadi et al., Exosome-mediated transfer of mRNAs and microRNAs is a novel mechanism of genetic exchange between cells. Nat Cell Biol. Jun. 2007;9(6):654-9. Epub May 7, 2007.

Venken et al., Genome-wide manipulations of Drosophila melanogaster with transposons, Flp recombinase, and ΦC31 integrase. Methods Mol Biol. 2012;859:203-28. doi: 10.1007/978-1-61779-603-6_12.

Verplank et al., Tsg101, a homologue of ubiquitin-conjugating (E2) enzymes, binds the L domain in HIV type 1 Pr55(Gag). Proc Natl Acad Sci U S A. Jul. 3, 2001;98(14):7724-9. Epub Jun. 26, 2001.

Von Schwedler et al., The protein network of HIV budding. Cell. Sep. 19, 2003;114(6):701-13.

Wehman et al., The P4-ATPase TAT-5 inhibits the budding of extracellular vesicles in C. elegans embryos. Curr Biol. Dec. 6, 2011;21(23):1951-9. doi: 10.1016/j.cub.2011.10.040. Epub Nov. 17, 2011.

Welton et al., Proteomics analysis of bladder cancer exosomes. Mol Cell Proteomics. Jun. 2010;9(6):1324-38. doi: 10.1074/mcp.M000063-MCP201. Epub Mar. 11, 2010.

Zhang et al., Conditional gene manipulation: Cre-ating a new biological era. J Zhejiang Univ Sci B. Jul. 2012;13(7):511-24. doi: 10.1631/jzus.B1200042.

EP 17859007.1, dated May 12, 2020, Extended European Search Report.

Extended European Search Report for EP 17859007.1, dated May 12, 2020.

Baccile et al., Modular synthesis of photocleavable peptides using click chemistry. Tetrahedron Lett. Apr. 11, 2012;53(15):1933-5.

Buchwald, Long-term, continuous intravenous heparin administration by an implantable infusion pump in ambulatory patients with recurrent venous thrombosis. Surgery. Oct. 1980;88(4):507-16.

Buys et al., Effect of screening on ovarian cancer mortality: the Prostate, Lung, Colorectal and Ovarian (PLCO) Cancer Screening Randomized Controlled Trial. JAMA. Jun. 8, 2011;305(22):2295-303. doi: 10.1001/jama.2011.766.

Cai et al., Solution structure of P22 transcriptional antitermination N peptide-boxB RNA complex. Nat Struct Biol. Mar. 1998;5(3):203-12.

Chen et al., Design of an in vivo cleavable disulfide linker in recombinant fusion proteins. Biotechniques. Jul. 2010;49(1):513-8. doi: 10.2144/000113450.

Chen et al., Fusion protein linkers: property, design and functionality. Adv Drug Deliv Rev. Oct. 2013;65(10):1357-69. doi:10.1016/j.addr.2012.09.039. Epub Sep. 29, 2012.

Choi et al., Protease-activated drug development. Theranostics. 2012;2(2):156-78. doi: 10.7150/thno.4068. Epub Feb. 8, 2012.

Cilley et al., Structural mimicry in the phage φ21 N peptide-boxB RNA complex. RNA. Jun. 2003;9(6):663-76.

Cochrane et al., The human immunodeficiency virus rev protein is a nuclear phosphoprotein. Virology. Jul. 1989;171(1):264-6.

Cook et al., Characterization of HIV-1 REV protein: binding stoichiometry and minimal RNA substrate. Nucleic Acids Res. Apr. 11, 1991;19(7):1577-83.

Cordingley et al., Sequence-specific interaction of Tat protein and Tat peptides with the transactivation-responsive sequence element of human immunodeficiency virus type 1 in vitro. Proc Natl Acad Sci U S A. Nov. 1990;87(22):8985-9.

Dingwall et al., Human immunodeficiency virus 1 tat protein binds trans-activation-responsive region (TAR) RNA in vitro. Proc Natl Acad Sci U S A. Sep. 1989;86(18):6925-9.

Dingwall et al., The nucleoplasmin nuclear location sequence is larger and more complex than that of SV-40 large T antigen. J Cell Biol. Sep. 1988;107(3):841-9.

(56) References Cited

OTHER PUBLICATIONS

Dowdy, Overcoming cellular barriers for Rna therapeutics. Nat Biotechnol. Mar. 2017;35(3):222-229. doi: 10.1038/nbt.3802. Epub Feb. 27, 2017.
During et al., Controlled release of dopamine from a polymeric brain implant: in vivo characterization. Ann Neurol. Apr. 1989;25(4):351-6.
Fernandes et al., The HIV-1 Rev response element: an RNA scaffold that directs the cooperative assembly of a homo-oligomeric ribonucleoprotein complex. RNA Biol. Jan. 2012;9(1):6-11. doi: 10.4161/rna.9.1.18178. Epub Jan. 1, 2012.
Gatignol et al., Characterization of a human TAR RNA-binding protein that activates the HIV-1 LTR. Science. Mar. 29, 1991;251(5001):1597-600.
Gatignol et al., Identification of cellular proteins that bind to the human immunodeficiency virus type 1 trans-activation-responsive TAR element RNA. Proc Natl Acad Sci U S A. Oct. 1989;86(20):7828-32.
Gaynor et al., Specific binding of a HeLa cell nuclear protein to RNA sequences in the human immunodeficiency virus transactivating region. Proc Natl Acad Sci U S A. Jul. 1989;86(13):4858-62.
Grate et al., Role REVersal: understanding how RRE RNA binds its peptide ligand. Structure. Jan. 15, 1997;5(1):7-11.
Hatahet et al., Disruption of reducing pathways is not essential for efficient disulfide bond formation in the cytoplasm of E. coli. Microb Cell Fact. Sep. 13, 2010;9:67. doi: 10.1186/14752859-9-67.
Heaphy et al., HIV-1 regulator of virion expression (Rev) protein binds to an RNA stem-loop structure located within the Rev response element region. Cell. Feb. 23, 1990;60(4):685-93.
Howard et al., Intracerebral drug delivery in rats with lesion-induced memory deficits. J Neurosurg. Jul. 1989;71(1):105-12.
Kakiyama et al., A peptide release system using a photo-cleavable linker in a cell array format for cell-toxicity analysis. Polymer Journal. Feb. 27, 2013;45:535-9.
Kalderon et al., A short amino acid sequence able to specify nuclear location. Cell. Dec. 1984;39(3 Pt 2):499-509.
Kamine et al., Mapping of HIV-1 Tat protein sequences required for binding to Tar RNA. Virology. Jun. 1991;182(2):570-7.
Keryer-Bibens et al., Tethering of proteins to RNAs by bacteriophage proteins. Biol Cell. Feb. 2008;100(2):125-38. doi: 10.1042/BC20070067.
Kole et al., RNA therapeutics: beyond RNA interference and antisense oligonucleotides. Nat Rev Drug Discov. Jan. 20, 2012;11(2):125-40. doi: 10.1038/nrd3625.
Kosugi et al., Six classes of nuclear localization signals specific to different binding grooves of importin α. J Biol Chem. Jan. 2, 2009;284(1):478-85. doi: 10.1074/jbc.M807017200. Epub Nov. 10, 2008.
Langer et al., Chemical and physical structure of polymers as carriers for controlled release of bioactive agents: A review. J Macromol Sci C. 1983;23(1):61-126. doi: 10.1080/07366578308079439. Epub Dec. 19, 2006.
Langer, New methods of drug delivery. Science. Sep. 28, 1990;249(4976):1527-33.
Legault et al., NMR structure of the bacteriophage lambda N peptide/boxB RNA complex: recognition of a GNRA fold by an arginine-rich motif. Cell. Apr. 17, 1998;93(2):289-99.
Levary et al., Protein-protein fusion catalyzed by sortase A. PLoS One. Apr. 6, 2011;6(4):e18342. doi: 10.1371/journal.pone.0018342.
Levy et al., Inhibition of calcification of bioprosthetic heart valves by local controlled-release diphosphonate. Science. Apr. 12, 1985;228(4696):190-2.
Loh et al., The Oct4 and Nanog transcription network regulates pluripotency in mouse embryonic stem cells. Nat Genet. Apr. 2006;38(4):431-40. Epub Mar. 5, 2006.
Makkerh et al., Comparative mutagenesis of nuclear localization signals reveals the importance of neutral and acidic amino acids. Curr Biol. Aug. 1, 1996;6(8):1025-7.
Marciniak et al., Identification and characterization of a HeLa nuclear protein that specifically binds to the trans-activation-response (TAR) element of human immunodeficiency virus. Proc Natl Acad Sci U S A. May 1990;87(9):3624-8.
McElroy et al., The use of alveolar epithelial type I cell-selective markers to investigate lung injury and repair. Eur Respir J. Oct. 2004;24(4):664-73.
Muesing et al., Regulation of mRNA accumulation by a human immunodeficiency virus trans-activator protein. Cell. Feb. 27, 1987;48(4):691-701.
Nimjee et al., Aptamers: an emerging class of therapeutics. Annu Rev Med. 2005;56:555-83.
Olejnik et al., Photocleavable biotin phosphoramidite for 5'-end-labeling, affinity purification and phosphorylation of synthetic oligonucleotides. Nucleic Acids Res. Jan. 15, 1996;24(2):361-6.
Parrott et al., RNA aptamers for the MS2 bacteriophage coat protein and the wild-type RNA operator have similar solution behaviour. Nucleic Acids Res. Jan. 15, 2000;28(2):489-97.
Patel, Adaptive recognition in RNA complexes with peptides and protein modules. Curr Opin Struct Biol. Feb. 1999;9(1):74-87.
Potti et al., Regulatable aptamers in medicine: focus on antithrombotic strategies. Expert Opin Biol Ther. Oct. 2004;4(10):1641-7.
Ray et al., Quantitative tracking of protein trafficking to the nucleus using cytosolic protein delivery by nanoparticle-stabilized nanocapsules. Bioconjug Chem. Jun. 17, 2015;26(6):1004-7. doi: 10.1021/acs.bioconjchem.5b00141. Epub Jun. 2, 2015.
Roy et al., A bulge structure in HIV-1 TAR RNA is required for Tat binding and Tat-mediated trans-activation. Genes Dev. Aug. 1990;4(8):1365-73.
Roy et al., Control of the interferon-induced 68-kilodalton protein kinase by the HIV-1 tat gene product. Science. Mar. 9, 1990;247(4947):1216-9.
Saudek et al., A preliminary trial of the programmable implantable medication system for insulin delivery. N Engl J Med. Aug. 31, 1989;321(9):574-9.
Sefton, Implantable pumps. Crit Rev Biomed Eng. 1987;14(3):201-40.
Shui et al., RNA aptamers that functionally interact with green fluorescent protein and its derivatives. Nucleic Acids Res. Mar. 2012;40(5):e39. doi: 10.1093/nar/gkr1264. Epub Dec. 20, 2011.
Srisawat et al., Streptavidin aptamers: affinity tags for the study of RNAs and ribonucleoproteins. RNA. Apr. 2001;7(4):632-41.
Stockley et al., Probing sequence-specific RNA recognition by the bacteriophage MS2 coat protein. Nucleic Acids Res. Jul. 11, 1995;23(13):2512-8.
Theile et al., Site-specific N-terminal labeling of proteins using sortase-mediated reactions. Nat Protoc. Sep. 2013;8(9):1800-7. doi: 10.1038/nprot.2013.102. Epub Aug. 29, 2013.
Tuerk et al., Systematic evolution of ligands by exponential enrichment: RNA ligands to bacteriophage T4 DNA polymerase. Science. Aug. 3, 1990;249(4968):505-10.
Ulrich et al., DNA and RNA aptamers: from tools for basic research towards therapeutic applications. Comb Chem High Throughput Screen. Sep. 2006;9(8):619-32.
Wang et al., ARMMs as a versatile platform for intracellular delivery of macromolecules. Nat Commun. Mar. 6, 2018;9(1):960. doi: 10.1038/s41467-018-03390-x.
Weeks et al., Fragments of the HIV-1 Tat protein specifically bind TAR RNA. Science. Sep. 14, 1990;249(4974):1281-5.
Weeks et al., RNA binding assays for Tat-derived peptides: implications for specificity. Biochemistry. Oct. 27, 1992;31(42):10281-7.
Weiss, RNA-mediated signaling in transcription. Nat Struct Biol. May 1998;5(5):329-33.
Witherell et al., Specific interaction between RNA phage coat proteins and RNA. Prog Nucleic Acid Res Mol Biol. 1991;40:185-220.
Zhang et al., Stabilized plasmid-lipid particles for regional gene therapy: formulation and transfection properties. Gene Ther. Aug. 1999;6(8):1438-47.

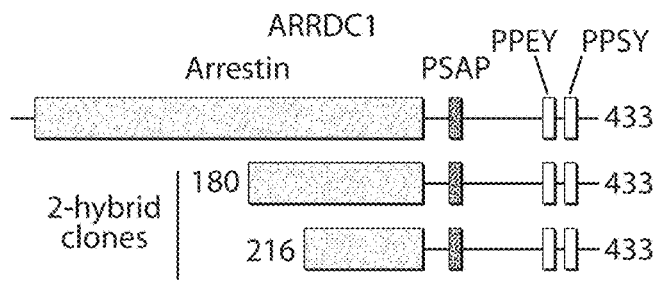
Fig. 1A
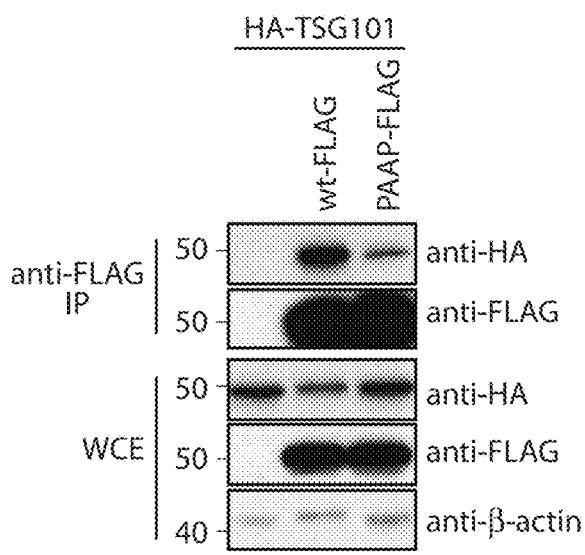
Fig. 1B
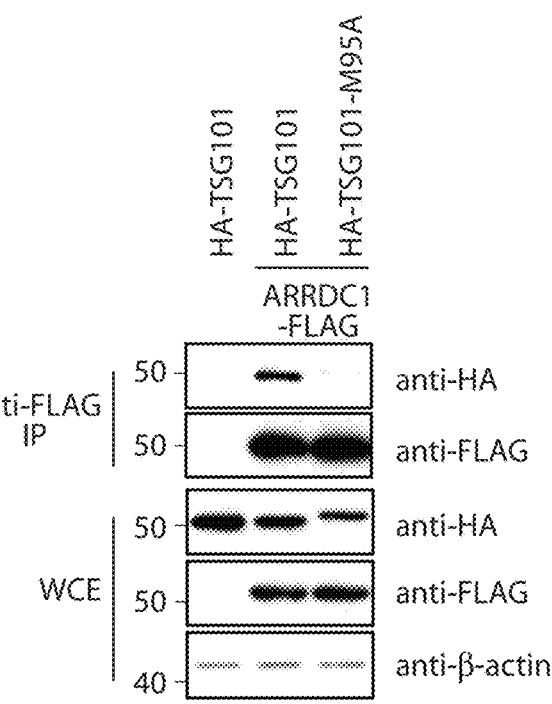
Fig. 1C
Fig. 1D

ARRDC1-MEDIATED MICROVESICLES (ARMMS) AND USES THEREOF

RELATED APPLICATION

This application is a divisional of and claims priority under 35 U.S.C. § 120 to U.S. patent application Ser. No. 14/376,967, filed Aug. 6, 2014, now U.S. Pat. No. 9,737,480, which is a national stage filing under 35 U.S.C. § 371 of international PCT application, PCT/US2013/024839, filed Feb. 6, 2013, which claims priority under 35 U.S.C. § 119(e) to U.S. provisional patent application Ser. No. 61/595,416, filed Feb. 6, 2012, each of which is incorporated herein by reference.

GOVERNMENT SUPPORT

This invention was made with government support under contract HDTRA1-06-C-0039 awarded by the Defense Threat Reduction Agency and under contract HL114769 awarded by the National Institutes of Health. The government has certain rights in the invention.

BACKGROUND OF THE INVENTION

Mammalian cells are capable of delivering multiple types of membrane capsules, also referred to as microvesicles, extracellularly. Such microvesicles shed by one cell can be taken up by another cell, thus allowing for intercellular communication and transport of molecules contained within the microvesicles. For example, the limiting membrane of late endosomes can fuse with the plasma membrane, leading to the extracellular release of multivesicular bodies (MVBs), initially contained within the endosomes, as exosomes. Also, budding viruses exploit the tumor susceptibility gene 101 (TSG101) protein and the highly conserved ESCRT (Endosomal Sorting Complex Required for Transport) machinery used for MVB formation to mediate the egress of viral particles from host cells.

SUMMARY OF THE INVENTION

Some aspects of this invention relate to the discovery of a virus-independent cellular process that generates microvesicles that are distinct from exosomes and which, like budding viruses, are produced by direct plasma membrane budding (DPMB). DPMB is driven by a specific interaction of TSG101 with a tetrapeptide PSAP motif of an accessory protein, the arrestin-domain-containing protein ARRDC1—which, as described herein, is localized to the plasma membrane through its arrestin domain. The ARRDC1/TSG101 interaction results in relocation of TSG101 from endosomes to the plasma membrane and mediates the release of microvesicles that contain TSG101, ARRDC1, and other cellular components, including, for example, proteins and nucleic acids.

Unlike exosomes, which are derived from MVBs, ARRDC1-mediated microvesicles (ARMMs) lack known late endosomal markers. ARMM formation involves VPS4 ATPase and is enhanced by the E3 ligase WWP2, which interacts with and ubiquitinates ARRDC1. Some aspects of this invention relate to the discovery of an intrinsic cellular mechanism that results in direct budding of microvesicles from the plasma membrane, providing a formal paradigm for the evolutionary recruitment of ESCRT proteins in the release of budding viruses. Some aspects of this invention relate to the surprising discovery that ARRDC1 protein discharged into ARMMs can be transferred to co-cultured cells, suggesting a role for ARMMs in intercellular communication, and allowing for the use of ARMMs as vectors for the delivery of various biomolecules (e.g., proteins, polypeptides, nucleic acids, RNAi agents) to a target cell without the need for genetically modifying a target cell. Other agents such as, for example, small molecules, can also be delivered via ARMMs.

In some aspects of this invention isolated ARMMs are provided. Such ARMMs may be isolated from a subject, a biological sample, or a cell culture, or ARMMs may be prepared synthetically. Methods for generating and/or isolating ARMMs, including ARMMs that include an agent to be delivered to a target cell or target cell population, are also provided herein. Methods for the use of ARMMs to deliver agents, for example, nucleic acids (e.g., siRNAs, microRNAs, lincRNAs), proteins or peptides (e.g., transcription factors, chromatin modulators, kinases, phosphorylases, or recombinases), or small molecules to target cells in vitro and in vivo are also provided, as are diagnostic and therapeutic methods using ARMMs.

Some aspects of this invention provide an isolated arrestin domain-containing protein 1 (ARRDC1)-mediated microvesicle (ARMM) comprising a lipid bilayer and an ARRDC1 protein, or fragment thereof. In some embodiments, the ARRDC1 protein or fragment thereof comprises an ARRDC1 PSAP domain. In some embodiments, the ARMM further comprises a TSG101 protein or fragment thereof. In some embodiments, the TSG101 protein fragment comprises a TSG101 UEV domain. In some embodiments, the ARMM further comprises a cell surface protein (e.g., receptor) or a cytosolic protein (e.g., enzyme). In some embodiments, the ARMM further comprises an integrin, a receptor tyrosine kinase, a G-protein coupled receptor, a membrane-bound immunoglobulin, or a protein listed in Table 1. In some embodiments, the microvesicle comprises an integrin chosen from the group consisting of α1β1, α2β1, α4β1, α5β1, α6β1, αLβ2, αMβ2, αIIbβ3, αVβ3, αVβ5, αVβ6, and α6β4 integrins; a receptor tyrosine kinase chosen from the group consisting of an EGF receptor (ErbB family), insulin receptor, PDGF receptor, FGF receptor, VEGF receptor, HGF receptor, Trk receptor, Eph receptor, AXL receptor, LTK receptor, TIE receptor, ROR receptor, DDR receptor, RET receptor, KLG receptor, RYK receptor, and MuSK receptor; a G-protein coupled receptor chosen from the group consisting of a rhodopsin-like receptor, secretin receptor, metabotropic glutamate/pheromone receptor, cyclic AMP receptor, frizzled/smoothened receptor, CXCR4, CCR5, or beta-adrenergic receptor; and/or an exocyst protein listed in Table 1 chosen from EXOC7, EXOC8, EXOC1, and EXOC2.

In some embodiments, the ARMM does not include an exosomal biomarker. In some embodiments, the ARMM does not include one or more exosomal biomarkers. In some embodiments, the exosomal biomarker is chosen from the group consisting of CD63, Lamp-1, Lamp-2, CD9, HSPA8, GAPDH, CD81, SDCBP, PDCD6IP, ENO1, ANXA2, ACTB, YWHAZ, HSP90AA1, ANXA5, EEF1A1, YWHAE, PPIA, MSN, CFL1, ALDOA, PGK1, EEF2, ANXA1, PKM2, HLA-DRA, and YWHAB.

Some embodiments of this invention provide ARMMs comprising an agent, for example, a protein, a nucleic acid, or a small molecule. In some embodiments, the agent is conjugated to the ARRDC1 protein, the ARRDC1 fragment, the TSG101 protein, or the TSG101 fragment. In some embodiments, the nucleic acid is an RNA. In some embodiments, the nucleic acid is an RNAi agent. In some embodiments, the nucleic acid is a coding RNA, a non-coding RNA, an antisense RNA, an mRNA, a small RNA, an siRNA, an shRNA, a microRNA, an snRNA, a snoRNA, a lincRNA, a structural RNA, a ribozyme, or a precursor thereof. In some embodiments, the nucleic acid is a DNA. In some embodiments, the nucleic acid comprises a restrotransposon sequence, a LINE sequence, a SINE sequence, a composite SINE sequence, or an LTR-retrotransposon sequence. In some embodiments, the nucleic acid encodes a protein. In some embodiments, the agent comprises a detectable label. In some embodiments, the agent is a therapeutic agent. In some embodiments, the agent is a drug approved for human or veterinary use by a governmental agency. In some embodiments, the agent is a cytotoxic agent. In some embodiments, the agent is a protein. In some embodiments, the agent is a transcription factor, a transcriptional repressor, a fluorescent protein, a kinase, a phosphatase, a protease, a ligase, or a recombinase. In some embodiments, the agent is a small molecule. In some embodiments, the agent is covalently bound to the ARRDC1 protein or fragment thereof, the TSG101 protein or fragment thereof, or another protein of the ARMM. In some embodiments, agent is conjugated to the ARRDC1 protein or fragment thereof, the TSG101 protein or fragment thereof, or other protein via a linker. In some embodiments, the linker is a cleavable linker. In some embodiments, the linker comprises a protease recognition site. In some embodiments, the linker is a UV-cleavable linker. In certain embodiments, the linker is cleaved under specific conditions such as pH, redox conditions, etc. In some embodiments, the microvesicle diameter is from about 30 nm to about 500 nm.

Some aspects of this invention provide an ARRDC1 fusion protein that comprises an ARRDC1 protein or a fragment thereof, and a polypeptide conjugated to the ARRDC1 protein or fragment thereof. In some embodiments, the ARRDC1 fragment comprises a PSAP domain. Some aspects of this invention provide a TSG101 fusion protein, comprising a TSG101 protein or a fragment thereof, and a polypeptide conjugated to the TSG101 protein or fragment thereof. In some embodiments, the TSG101 fragment comprises a UEV domain. In some embodiments, the conjugated polypeptide comprises a transcription factor, a transcriptional repressor, a fluorescent protein, a kinase, a phosphatase, a protease, a ligase, or a recombinase. In some embodiments, the polypeptide is conjugated to the ARRDC1 protein, the ARRDC1 protein fragment, the TSG101 protein, the TSG101 protein fragment, or other ARMM-associated protein via a covalent bond. In some embodiments, the polypeptide is conjugated to the ARRDC1 protein, the ARRDC1 protein fragment, the TSG101 protein, or the TSG101 protein fragment via a linker. In some embodiments, the linker is a cleavable linker.

Some aspects of this invention provide a microvesicle-producing cell that comprises a recombinant expression construct encoding an ARRDC1 protein, or a PSAP domain-comprising fragment thereof, under the control of a heterologous promoter. In some embodiments, the expression of ARRDC1 induces or increases ARMM production of the cell. In some embodiments, the cell expresses or contains an agent in its cytoplasm or its plasma membrane that is included in ARMMs produced by the cell. Some aspects of this invention provide a microvesicle-producing cell that comprises a recombinant expression construct encoding a TSG101 protein, or a UEV domain-comprising fragment thereof, under the control of a heterologous promoter. In some embodiments, the expression construct further encodes a polypeptide fused to the ARRDC1 protein or the TSG101 protein. In some embodiments, the polypeptide comprises a transcription factor, a transcriptional repressor, a fluorescent protein, a kinase, a phosphatase, a protease, a ligase, or a recombinase. In some embodiments, the cells is a eukaryotic cell. In some embodiments, the cell is a mammalian cell. In some embodiments, the cell is a human cell. In some embodiments, the cell further comprises a recombinant expression construct encoding an RNAi agent. In some embodiments, the RNAi agent is a nucleic acid. In some embodiments, the nucleic acid is a non-coding RNA, an antisense RNA, a small RNA, an siRNA, an shRNA, a microRNA, an snRNA, a snoRNA, a lincRNA, or a precursor thereof. In some embodiments, the cell further comprises a recombinant expression construct encoding a ribozyme.

Some aspects of this invention provide methods of delivering an agent to a target cell comprising contacting the target cell with a microvesicle with an agent to be delivered, as described herein. In other aspects of this invention provided are methods of delivering an agent to a target cell by exposing the target cell to a microvesicle-producing cell (e.g., by co-culturing both cells). In certain embodiments, the invention provides methods of delivering an agent to a target cell comprising contacting the target cell with an isolated microvesicle that comprises a lipid bilayer, an ARRDC1 protein or fragment thereof, and the agent to be delivered. In certain embodiments, the target cell is a mammalian cell. In some embodiments, the target cell is a human cell. In some embodiments, the target cell is a stem cell. In some embodiments, the target cell is a cell in vitro or ex vivo, and the method comprises administering the microvesicle to the cell in vitro, or co-culturing the target cell with the microvesicle-producing cell in vitro. In some embodiments, the target cell is a cell in a subject, and the method comprises administering the microvesicle or the microvesicle-producing cell to the subject. In some embodiments, the subject is a mammalian subject. In some embodiments, the subject is a human subject. In some embodiments, the target cell is a pathological cell. In some embodiments, the target cell is a cancer cell. In some embodiments, the microvesicle includes a targeting agent that selectively binds an antigen of the target cell. In some embodiments, the antigen of the target cell is a cell surface antigen. In some embodiments, the targeting agent is a membrane-bound immunoglobulin, an integrin, a receptor, a receptor ligand, an aptamer, a small molecule, or a fragment thereof.

Some aspects of this invention provide an in vitro cell culture system comprising (a) a microvesicle-producing cell population comprising a recombinant expression construct encoding (i) an ARRDC1 protein or fragment thereof under the control of a heterologous promoter, and/or (ii) a TSG101 protein or fragment thereof under the control of a heterologous promoter; and (b) a target cell population. In some embodiments, the ARRDC1 fragment comprises a PSAP domain, and/or the TSG101 fragment comprises a UEV domain. In some embodiments, the expression construct further encodes a polypeptide fused to the ARRDC1 protein or fragment thereof. In some embodiments, the expression construct further encodes a polypeptide fused to the TSG101 protein or fragment thereof. In some embodiments, the polypeptide fused to the ARRDC1 protein or fragment, or to the TSG101 protein or fragment, independently comprises a transcription factor, a transcriptional repressor, a fluorescent protein, a kinase, a phosphatase, a protease, a ligase, or a recombinase. In some embodiments, the microvesicle-producing cell is a mammalian cell. In some embodiments, the microvesicle-producing cell is a non-proliferating cell. In some embodiments, the microvesicle-producing cell is a feeder cell. In some embodiments, the microvesicle-producing cell is an immortalized cell. For example, in some embodiments, the microvesicle-producing cell is a HEK293T cell, a HeLa cell, or an A549 cell. In some embodiments, the target cell is a mammalian cell. In some embodiments, the target cell is a human cell. In some embodiments, the target cell is a differentiated cell. In some embodiments, the target cell is a stem cell.

In yet other aspects, the invention provides methods of detecting a condition in a subject. The detection of ARMMs or certain characteristics of the ARMM may be used to diagnose a specific condition or disease in a subject. For example, the detection of ARMMs may be used to diagnose cancer in subject. In certain embodiments, the inventive method comprises (a) obtaining or detecting an ARMM from the subject or a biological sample from the subject; and (b) detecting a biomarker profile indicative of the condition in the ARMM obtained from the subject; wherein the presence of the biomarker profile in the ARMM obtained from the subject indicates the presence of the condition in the subject. In some embodiments, the method further comprises obtaining a biological sample from the subject that comprises an ARMM. In some embodiments, a method is provided that comprises detecting the presence of an ARMM or a level of ARMMs to diagnose a disease. Some aspects of this invention provide methods of detecting a pathological cell or cell population in a subject comprising (a) detecting a level of ARMMs produced by a cell or cell population obtained from the subject; and (b) comparing the level of ARMMs to a control level, wherein, if the level of ARMMs produced by the cell or cell population obtained from the subject is higher than the control level, then the cell or cell population is indicative of a pathological cell or cell population. In some embodiments, the method further comprises obtaining a sample from the subject comprising a cell or cell population producing ARMMs. Some aspects of this invention provide methods of detecting a pathological cell or cell population in a subject comprising (a) obtaining an ARMM from the subject; and (b) detecting a biomarker profile indicative of the pathological cell or cell population in the ARMM obtained from the subject; wherein the presence of the biomarker profile in the ARMM obtained from the subject indicates the presence of the pathological cell or cell population condition in the subject. In some embodiments, the method further comprises obtaining a sample from the subject comprising an ARMM. In some embodiments, the pathological cell or cell population is a malignant cell or cell population.

Some aspects of this invention provide an expression construct comprising (a) a nucleotide sequence encoding an ARRDC1 protein, or fragment thereof operably, linked to a heterologous promoter, and (b) a restriction site or a recombination site positioned adjacent to the ARRDC1-encoding nucleotide sequence allowing for the insertion of a nucleotide sequence encoding an additional polypeptide in frame with the ARRDC1-encoding nucleotide sequence. Such expression constructs are useful for generating ARRDC1 fusion proteins that can be expressed in a cell, which, in turn, induces or increases ARMM production in the cell. An ARMM produced by a cell expressing such an ARRDC1 fusion protein will, in some embodiments, comprise the ARRDC1 fusion protein encoded by the expression construct. ARRDC1 and TSG101 fusion proteins can be used as research tools to investigate ARMM generation or trace the respective fusion proteins or the ARMMs that they are incorporated into. For example, in some embodiments, an expression construct encoding an ARRDC1 or TSG101 fusion protein comprising a fluorescent protein are provided. Some aspects of this invention provide an expression construct comprising (a) a nucleotide sequence encoding a TSG101 protein or fragment thereof operably linked to a heterologous promoter, and (b) a restriction site or a recombination site positioned adjacent to the TSG101-encoding nucleotide sequence allowing for the insertion of a nucleotide sequence encoding an additional polypeptide in frame with the TSG101-encoding nucleotide sequence.

Other advantages, features, and uses of the invention will be apparent from the detailed description of certain exemplary, non-limiting embodiments; the drawings; the non-limiting working examples; and the claims.

BRIEF DESCRIPTION OF THE DRAWINGS

FIGS. 1A-1E. ARRDC1 interacts with and recruits TSG101 to the cell membrane via a conserved PSAP motif. (FIG. 1A) Schematic representation of the ARRDC1 protein, indicating relevant structural domains: the N-terminal arrestin domain (gray box), and the C-terminal PSAP motif (filled box), and PPXY motifs (open boxes). Also depicted are the ARRDC1 fragments identified in the yeast two-hybrid screen using the UEV domain of TSG101 as the bait. The sequences, from left to right, correspond to SEQ ID NOs: 37-39. (FIG. 1B) Alignment of fragments of ARRDC1 orthologs showing conservation of the PSAP motif. Sequences correspond, from top to bottom, to SEQ ID NOs: 8 to 13. (FIG. 1C) Western blot analysis of the interaction between FLAG-tagged wild-type (wt) ARRDC1 or the PSAP mutant (PAAP (SEQ ID NO: 32)) and HA-tagged TSG101. Anti-FLAG immunoprecipitates and whole cell extracts (WCE) from 293T cells transfected with the indicated constructs were examined by immunoblotting using the indicated antibodies. (FIG. 1D) Western blot analysis of the interaction between HA-tagged wild type or a mutant (M95A) TSG101 with ARRDC1, as in (FIG. 1C). (FIG. 1E) Localization of mCherry-TSG101 fusion protein in 293T cells co-transfected with GFP, ARRDC1-GFP, or its PSAP mutant (PAAP (SEQ ID NO: 32)). Cells were fixed and examined by confocal microscopy. More than twenty cells expressing both ARRDC1-GFP and mcherry-TSG101 were examined and all showed similar localization pattern. Representative images are shown in the figure.

(FIG. 2A) Western blot analysis, using the indicated antibodies, of whole cell extracts and of the corresponding extracellular vesicles produced by 293T cells transfected with constructs expressing GFP, wt ARRDC1-GFP (wt), or HIV GAG-GFP. (FIG. 2B) Electron microscopy of extracellular vesicles derived from 293T cells transfected with an ARRDC1 expression construct. Scale bar=100 nm. (FIG. 2C) Western blot analysis of whole cell extracts (WCEs) and extracellular vesicles from 293T cells transfected with non-targeting shRNA or ARRDC1-targeting shRNA lentiviruses. (FIG. 2D) Anti-ARRDC1 and anti-CD63 immunogold labeling of collagen-embedded extracellular vesicle cryosections. Arrows indicate immunogold-positive labeling. Scale bar=100 nm. (FIG. 2E) Transfer of ARRDC1-containing vesicles from donor to recipient cells. Cells transfected by increasing amounts of constructs expressing ARRDC1-GFP or GFP were washed and seeded in 0.4 μm transwells atop untransfected cells. Western blot analysis of the corresponding lysates from transfected donor cells and untransfected recipient cells was carried out using the indicated antibodies.

(FIG. 3A) ARRDC1 and TSG101 are required for ARMMs release. Western blot analysis of ARMMs and whole cell extracts (WCE) from 293T cells subjected to transfection by indicated siRNAs. The results shown are representative of three independent replication experiments. (FIG. 3B) PSAP mutant ARRDC1 is released less efficiently into ARMMs. Cells were transfected with wt or PSAP mutant (PAAP (SEQ ID NO: 32)) ARRDC1-GFP and the corresponding WCEs and ARMMs were analyzed by Western blotting probed by the indicated antibodies. (FIG. 3C) ARMMs release requires functional VPS4 ATPase activity. 293T cells were co-transfected with constructs expressing HA-ARRDC1 and 0.5 or 1 μg of VPS4a or VPS4a E228Q (VPS4a DN) GFP fusion proteins. WCEs and ARMMs were analyzed by Western blotting using the indicated antibodies.

(FIG. 4A) ARMMs bud at the cell surface. Cryosections of 293T cells transfected with constructs expressing mCherry or ARRDC1-mCherry were immunogold labeled with anti-mCherry. White arrows in the right panel indicate presumptive outward budding at the cell membrane adjacent to immunogold-positive ARMMs captured from the intercellular space. An untransfected cell is indicated in the same field and shows no staining. Scale bar=100 nm. (FIG. 4B) Disruption of conserved arrestin residues alters localization of ARRDC1. Conserved arrestin domain residues among arrestins 1-4 and the known membrane-associated ARRDC1 and ARRDC3 were identified by ClustalW alignment and were mutated. The corresponding mCherry fusion mutants were expressed in 293T cells and showed altered localization compared to wt or PAAP ARRDC1. The sequences in the schematic, from top to bottom and left to right, correspond to SEQ ID NOs: 14-31. (FIG. 4C) 293T cells were transfected with constructs expressing the indicated ARRDC1 mutants fused to mCherry. The corresponding ARMMs and WCEs were analyzed by Western blotting with the indicated antibodies. The sequence corresponds to SEQ ID NO: 32.

(FIG. 5A) Deletion of PPXY motifs reduced ARRDC1 ubiquitination and ARMMs release. 293T cells were transfected with wt or PPXY deletion (ΔΔPPXY) ARRDC1 fused to mCherry and visualized by confocal microscopy. The corresponding cell lysates and ARMMs were analyzing by Western blotting as indicated. (FIG. 5B) PPXY motifs in ARRDC1 interact with WWP2. 293T cells were co-transfected with GFP-tagged WWP2 and HA-tagged wt or ΔΔPPXY ARRDC1. Anti-HA immunoprecipitates and WCEs were examined by Western blotting as indicated. WWP2 expression potentiates ARRDC1 ubiquitination in ARMMs. 293T cells were co-transfected with constructs expressing HA-ARRDC1 and WWP2-GFP or the WW domain of WWP2 fused to GFP. WCEs and ARMMs from each transfected group were analyzed by immunoblotting as indicated. WWP2 knockdown diminishes ARRDC1 in ARMMs. 293T was subjected to transfection with non-targeting (NT) or WWP2-targeting siRNAs. Corresponding WCEs and ARMMs were analyzed by Western blotting.

(FIG. 7A) 293T cells were seeded on cover slips and transfected with 20 ng of Flag-ARRDC1 expression plasmid. 48 h later, cells were fixed, permeabilized, and stained with anti-ARRDC1 primary antibody (1:200) or no primary as a control, followed by incubation with secondary anti-Rabbit IgG antibody conjugated to TRITC (Sigma; 1:500). Cover slips were mounted on glass slides and visualized by confocal microscopy. (FIG. 7B) 293T, HeLa, and A549 cells were seeded on cover slips, transfected with 100 ng of the ARRDC1-GFP construct, and visualized by confocal microscopy. DAPI staining was used to visualize the nuclei.

DEFINITIONS

Figure 1E:
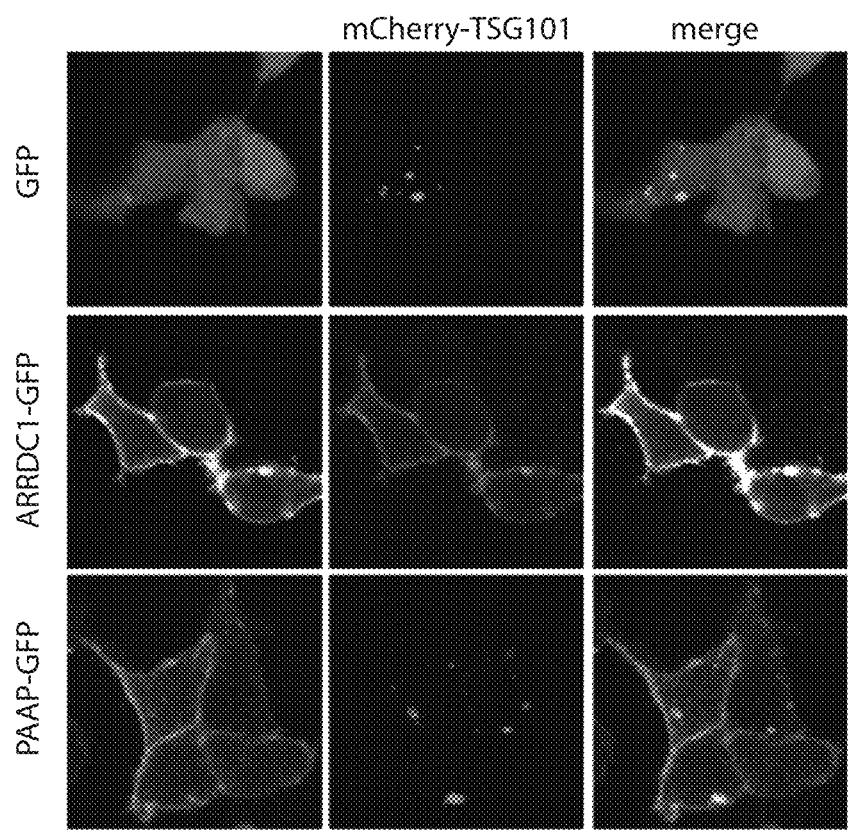

Agent and agent to be delivered: As used herein, the term "agent" refers to a substance that can be incorporated in an ARMM, for example, into the liquid phase of the ARMM or into the lipid bilayer of the ARMM. The term "agent to be delivered" refers to any substance that can be delivered to a subject, organ, tissue, or cell. In some embodiments, the agent is an agent to be delivered to a target cell. In some embodiments, the agent to be delivered is a biologically active agent, i.e., it has activity in a cell, biological system, and/or subject. For instance, a substance that, when administered to an subject, has a biological effect on that subject, is considered to be biologically active. In some embodiments, an agent to be delivered is a therapeutic agent. As used herein, the term "therapeutic agent" refers to any agent that, when administered to a subject, has a beneficial effect. The term "therapeutic agent" refers to any agent that, when administered to a subject, has a therapeutic, diagnostic, and/or prophylactic effect and/or elicits a desired biological and/or pharmacological effect. As used herein, the term "therapeutic agent" may be a nucleic acid that is delivered to a cell via its association with or inclusion into an ARMM. In certain embodiments, the agent to be delivered is a nucleic acid. In certain embodiments, the agent to be delivered is DNA. In certain embodiments, the agent to be delivered is RNA. In certain embodiments, the agent to be delivered is a peptide or protein. In some embodiments, the functional protein or peptide to be delivered into a cell is a transcription factor, a tumor suppressor, a developmental regulator, a growth factor, a metastasis suppressor, a pro-apoptotic protein, a zinc finger nuclease, or a recombinase. In some embodiments, the protein to be delivered is p53, Rb (retinoblastoma protein), BRCA1, BRCA2, PTEN, APC, CD95, ST7, ST14, a BCL-2 family protein, a caspase; BRMS1, CRSP3, DRG1, KAI1, KISS1, NM23, a TIMP-family protein, a BMP-family growth factor, EGF, EPO, FGF, G-CSF, GM-CSF, a GDF-family growth factor, HGF, HDGF, IGF, PDGF, TPO, TGF-α, TGF-β, VEGF; a zinc finger nuclease targeting a site within the human CCR5 gene, Cre, Dre, or FLP recombinase. In certain embodiments, the agent to be delivered is a small molecule. In some embodiments, the agent to be delivered is a diagnostic agent. In some embodiments, the agent to be delivered is useful as an imaging agent. In some of these embodiments, the diagnostic or imaging agent is, and in others it is not, biologically active.

Animal: As used herein, the term "animal" refers to any member of the animal kingdom. In some embodiments, "animal" refers to humans of either sex at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone. In some embodiments, the animal is a transgenic non-human animal, genetically-engineered non-human animal, or a non-human clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more entities, for example, moieties, molecules, and/or ARMMs, means that the entities are physically associated or connected with one another, either directly or via one or more additional moieties that serves as a linker, to form a structure that is sufficiently stable so that the entities remain physically associated under the conditions in which the structure is used, e.g., physiological conditions. An ARMM is typically associated with an agent, for example, a nucleic acid, protein, or small molecule, by a mechanism that involves a covalent or non-covalent association. In certain embodiments, the agent to be delivered is covalently bound to a molecule that is part of the ARMM, for example, an ARRCD1 protein or fragment thereof, a TSG101 protein or fragment thereof, or a lipid or protein that forms part of the lipid bilayer of the ARMM. In some embodiments, a peptide or protein is associated with an ARRCD1 protein or fragment thereof, a TSG101 protein or fragment thereof, or a lipid bilayer-associated protein by a covalent bond (e.g., an amide bond). In some embodiments, the association is via a linker, for example, a cleavable linker. In some embodiments, an entity is associated with an ARMM by inclusion in the ARMM, for example, by encapsulation of an entity (e.g., an agent) within the ARMM. For example, in some embodiments, an agent present in the cytoplasm of an ARMM-producing cell is associated with an ARMM by encapsulation of agent-comprising cytoplasm in the ARMM upon ARMM budding. Similarly, a membrane protein, or other molecule associated with the cell membrane of an ARMM producing cell may be associated with an ARMM produced by the cell by inclusion into the ARMM membrane upon budding.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, where a nucleic acid is biologically active, a portion of that nucleic acid that shares at least one biological activity of the whole nucleic acid is typically referred to as a "biologically active" portion.

Biomarker: The term "biomarker" as used herein in the context of ARMM-based diagnostics, refers to a detectable molecule (e.g., a protein, a peptide, a proteoglycan, a glycoprotein, a lipoprotein, a carbohydrate, a lipid, a nucleic acid (e.g., DNA, such as cDNA or amplified DNA, or RNA, such as mRNA), an organic or inorganic chemical, a small molecule (e.g., second messenger, a metabolite), or a discriminating molecule or discriminating fragment of any of the foregoing), that is present in or derived from a biological sample containing ARMMs, or any ratio of such molecules, or any other characteristic that is objectively measured and evaluated as an indicator of a specific biologic feature or process, for example, of cell or vesicle identity, of a normal or a pathogenic processes, or a pharmacologic response to a therapeutic intervention, or an indication thereof. See Atkinson, A. J., et al., Biomarkers and Surrogate Endpoints: Preferred Definitions and Conceptual Framework, *Clinical Pharm. & Therapeutics,* 2001 March; 69(3): 89-95. In this context, the term "derived from" refers to a compound that, when detected, is indicative of a particular molecule being present in the biological sample. For example, detection of a particular cDNA can be indicative of the presence of a particular RNA transcript or protein in the biological sample. As another example, detection of or binding to a particular antibody can be indicative of the presence of a particular antigen (e.g., protein) in the biological sample. In some embodiments, a discriminating molecule or fragment is a molecule or fragment that, when detected, indicates presence or abundance of an above-identified compound. A biomarker can, for example, be isolated from an ARMM, directly measured as part of an ARMM, or detected in or determined to be included in an ARMM. In some embodiments, the amount of ARMMs detected in a sample from a subject or in a cell population derived from a sample obtained from a subject, or the rate of ARMM generation within a sample or cell population obtained from a subject serves as a biomarker. Methods for the detection of biomarkers are known to those of skill in the art and include nucleic acid detection methods, protein detection methods, carbohydrate detection methods, antigen detection methods, and other suitable methods.

A "biomarker profile" comprises one or more biomarkers (e.g., an mRNA molecule, a cDNA molecule, a protein, and/or a carbohydrate, or an indication thereof). The biomarkers of the biomarker profile can be in the same or different classes, such as, for example, a nucleic acid, a carbohydrate, a metabolite, and a protein. A biomarker profile may comprise at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more biomarkers. In some embodiments, a biomarker profile comprises hundreds, or even thousands, of biomarkers. A biomarker profile can further comprise one or more controls or internal standards. In some embodiments, the biomarker profile comprises at least one biomarker that serves as an internal standard. In some embodiments, the presence or level of ARRDC1 or TSG101 in a sample or cell population is used as an internal standard. Biomarker profiles for several conditions, diseases, pathologies, and also for normal states are known to those of skill in the art, and the invention is not limited to any particular biomarker profile. In some embodiments, the biomarker profile used in the context of ARMM-based diagnostic methods as described herein is a biomarker profile that has been described to be useful for exosome-base diagnostics. Exosomal biomarker profiles are known to those of skill in the art and biomarker profiles useful for the diagnosis of various disease, including different cancers, stroke, autism, and other diseases, have been described, for example, in U.S. patent application Ser. No. 13/009,285, filed on Jan. 19, 2011 (published as US 2011/0151460 A1) by Kaas et al., and entitled *Methods And Systems Of Using Exosomes For Determining Phenotypes*, the entire contents of which are incorporated herein by reference.

Conserved: As used herein, the term "conserved" refers to nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Functional: As used herein, a "functional" biological molecule is a biological molecule in a form in which it exhibits a property and/or activity by which it is characterized or useful.

Fusion protein: As used herein, a "fusion protein" includes a first protein moiety, e.g., an ARRCD1 protein or fragment thereof, or a TSG101 protein or fragment thereof, having a peptide linkage with a second protein moiety, for example, a protein to be delivered to a target cell. In certain embodiments, the fusion protein is encoded by a single fusion gene.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as RNAi agents, ribozymes, tRNAs, etc. For the purpose of clarity it should be noted that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein—coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Green fluorescent protein: As used herein, the term "green fluorescent protein" (GFP) refers to a protein originally isolated from the jellyfish *Aequorea victoria* that fluoresces green when exposed to blue light or a derivative of such a protein (e.g., an enhanced or wavelength-shifted version of the protein). The amino acid sequence of wild type GFP is as follows:

```
                                          (SEQ ID NO: 1)
MSKGEELFTG  VVPILVELDG  DVNGHKFSVS  GEGEGDATYG

KLTLKFICTT  GKLPVPWPTL  VTTFSYGVQC  FSRYPDHMKQ

HDFFKSAMPE  GYVQERTIFF  KDDGNYKTRA  EVKFEGDTLV

NRIELKGIDF  KEDGNILGHK  LEYNYNSHNV  YIMADKQKNG

IKVNFKIRHN  IEDGSVQLAD  HYQQNTPIGD  GPVLLPDNHY

LSTQSALSKD  PNEKRDHMVL  LEFVTAAGIT  HGMDELYK
```

Proteins that are at least 70%, at least 75%, at least 80%, at least 85%, at least 90%, at least 95%, at least 98%, or at least 99% homologous are also considered to be green fluorescent proteins.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (nucleotides sequences or amino acid sequences). In accordance with the invention, two nucleotide sequences are considered to be homologous if the polypeptides they encode are at least about 50% identical, at least about 60% identical, at least about 70% identical, at least about 80% identical, or at least about 90% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for nucleotide sequences to be considered homologous. For nucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical, at least about 70% identical, at least about 80% identical, or at least about 90% identical for at least one stretch of at least about 20 amino acids.

Identity: As used herein, the term "identity" refers to the overall relatedness between polymeric molecules, e.g., between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Atschul, S. F. et al., *J. Molec. Biol.*, 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of gene expression may be determined using standard techniques for measuring mRNA and/or protein levels.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe).

Isolated: As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

microRNA (miRNA): As used herein, the term "microRNA" or "miRNA" refers to an RNAi agent that is approximately 21 nucleotides (nt)-23 nt in length. miRNAs can range between 18 nt-26 nt in length. Typically, miRNAs are single-stranded. However, in some embodiments, miRNAs may be at least partially double-stranded. In certain embodiments, miRNAs may comprise an RNA duplex (referred to herein as a "duplex region") and may optionally further comprises one to three single-stranded overhangs. In some embodiments, an RNAi agent comprises a duplex region ranging from 15 bp to 29 bp in length and optionally further comprising one or two single-stranded overhangs. An miRNA may be formed from two RNA molecules that hybridize together, or may alternatively be generated from a single RNA molecule that includes a self-hybridizing portion. In general, free 5' ends of miRNA molecules have phosphate groups, and free 3' ends have hydroxyl groups. The duplex portion of an miRNA usually, but does not necessarily, comprise one or more bulges consisting of one or more unpaired nucleotides. One strand of an miRNA includes a portion that hybridizes with a target RNA. In certain embodiments, one strand of the miRNA is not precisely complementary with a region of the target RNA, meaning that the miRNA hybridizes to the target RNA with one or more mismatches. In some embodiments, one strand of the miRNA is precisely complementary with a region of the target RNA, meaning that the miRNA hybridizes to the target RNA with no mismatches. Typically, miRNAs are thought to mediate inhibition of gene expression by inhibiting translation of target transcripts. However, in some embodiments, miRNAs may mediate inhibition of gene expression by causing degradation of target transcripts.

The term "microvesicle," as used herein, refers to a droplet of liquid surrounded by a lipid bilayer. In some embodiments, a microvesicle has a diameter of about 10 nm to about 1000 nm. In some embodiments, a microvesicle has a diameter of at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 125 nm, at least about 150 nm, at least about 175 nm, at least about 200 nm, at least about 250 nm, at least about 300 nm, at least about 400 nm, or at least about 500 nm. In some embodiments, a microvesicle has a diameter of less than about 1000 nm, less than about 900 nm, less than about 800 nm, less than about 700 nm, less than about 600 nm, lesson about 500 nm, less than about 400 nm, less than about 300 nm, less than about 250 nm, less than about 200 nm, lesson about 150 nm, less than about 100 nm, less than about 90 nm, less than about 80 nm, lesson about 70 nm, lesson about 60 nm, or less than about 50 nm. The term microvesicle includes microvesicle shed from cells as well as synthetically produced microvesicles. Microvesicles shed from cells typically comprise the antigenic content of the cells from which they originate. Microvesicles shed from cells also typically comprise an asymmetric distribution of phospholipids, reflecting the phospholipid distribution of the cells from which they originate. In some embodiments, the inner membrane of microvesicles provided herein, e.g., of some ARMMs, comprises the majority of aminophospholipids, phosphatidylserine, and/or phosphatidylethanolamine within the lipid bilayer.

The term "ARMM," as used herein, refers to a microvesicle comprising an ARRDC1 protein or fragment thereof, and/or TSG101 protein or fragment thereof. The molecular mechanism by which ARMMs are produced is described in more detail elsewhere herein. In some embodiments, the ARMM is shed from a cell, and comprises a molecule, for example, a nucleic acid, protein, or small molecule, present in the cytoplasm of the cell. In some embodiments, the ARMM is shed from a transgenic cell comprising a recombinant expression construct that includes the transgene, and the ARMM comprises a gene product, for example, a transcript or a protein encoded by the expression construct. In some embodiments, the ARMM is produced synthetically, for example, by contacting lipid bilayer within ARRDC1 protein in a cell free system in the presence of TSG101, HECT domain ligase, and VPS4a. In some embodiments, an ARMM lacks a late endosomal marker. Some ARMMs as provided herein do not include, or are negative for, one or more exosomal biomarker. Exosomal biomarkers are known to those of skill in the art and include, but are not limited to CD63, Lamp-1, Lamp-2, CD9, HSPA8, GAPDH, CD81, SDCBP, PDCD6IP, ENO1, ANXA2, ACTB, YWHAZ, HSP90AA1, ANXA5, EEF1A1, YWHAE, PPIA, MSN, CFL1, ALDOA, PGK1, EEF2, ANXA1, PKM2, HLA-DRA, and YWHAB. For example, some ARMMs provided herein lack CD63, some ARMMs lack LAMP1, some ARMMs lack CD9, some ARMMs lack CD81, some ARMMs lack CD63 and Lamp-1, some ARMMs lack CD63, Lamp-1, and CD9, some ARMMs lack CD63, Lamp-1, CD81 and CD9, and so forth. Certain ARMMs provided herein may include an exosomal biomarker. Accordingly, some ARMMs may be negative for one or more exosomal biomarker, but positive for one or more different exosomal biomarker. For example, such an ARMM may be negative for CD63 and Lamp-1, but may include PGK1 or GAPDH; or may be negative for CD63, Lamp-1, CD9 and CD81, but may be positive for HLA-DRA. In some embodiments, ARMMs include an exosomal biomarker, but at a lower level than a level found in exosomes. For example, some ARMMs include one or more exosomal biomarkers at a level of less than about 1%, less than about 5%, less than about 10%, less than about 20%, less than about 30%, less than about 40%, or less than about 50% of the level of that biomarker found in exosomes. To give a non-limiting example, in some embodiments, an ARMM may be negative for CD63 and Lamp-1, include CD9 at a level of less than about 5% of the level of CD9 typically found in exosomes, and be positive for ACTB. Exosomal biomarkers in addition to those listed above are known to those of skill in the art, and the invention is not limited in this regard.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably to refer to a polymer of nucleotides (e.g., a string of at least two nucleotides). In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g. polynucleotides and residues, including nucleotides and/or nucleosides) that have not been chemically modified in order to facilitate or achieve delivery.

Protein: The term "protein" is used herein interchangeably with the terms polypeptide and peptide, and refers to a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., addition of a chemical entity such as a carbohydrate group, a phosphate group, a farnesyl group, an isofarnesyl group, a fatty acid group, an amide group, a terminal acetyl group, a linker for conjugation, functionalization, or other modification (e.g., alpha amidation), etc. In certain embodiments, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, the modifications of the peptide lead to a more biologically active peptide. In some embodiments, polypeptides may comprise natural amino acids, non-natural amino acids, synthetic amino acids, amino acid analogs, and combinations thereof.

Reprogramming factor: As used herein, the term "reprogramming factor" refers to a factor that, alone or in combination with other factors, can change the state of a cell from a somatic, differentiated state into a pluripotent stem cell state. Non-limiting examples of reprogramming factors include a protein (e.g., a transcription factor), a peptide, a nucleic acid, or a small molecule. Known reprogramming factors that are useful for cell reprogramming include, but are not limited to Oct4, Sox2, Klf4, and c-myc. Similarly, a programming factor may be used to modulate cell differentiation, for example, to facilitate or induce cell differentiation towards a desired lineage.

RNA interference (RNAi): As used herein, the term "RNA interference" or "RNAi" refers to sequence-specific inhibition of gene expression and/or reduction in target RNA levels mediated by an RNA, which RNA comprises a portion that is substantially complementary to a target RNA. Typically, at least part of the substantially complementary portion is within the double stranded region of the RNA. In some embodiments, RNAi can occur via selective intracellular degradation of RNA. In some embodiments, RNAi can occur by translational repression.

RNAi agent: As used herein, the term "RNAi agent" or "RNAi" refers to an RNA, optionally including one or more nucleotide analogs or modifications, having a structure characteristic of molecules that can mediate inhibition of gene expression through an RNAi mechanism. In some embodiments, RNAi agents mediate inhibition of gene expression by causing degradation of target transcripts. In some embodiments, RNAi agents mediate inhibition of gene expression by inhibiting translation of target transcripts. Generally, an RNAi agent includes a portion that is substantially complementary to a target RNA. In some embodiments, RNAi agents are at least partly double-stranded. In some embodiments, RNAi agents are single-stranded. In some embodiments, exemplary RNAi agents can include siRNA, shRNA, and/or miRNA. In some embodiments, RNAi agents may be composed entirely of natural RNA nucleotides (i.e., adenine, guanine, cytosine, and uracil). In some embodiments, RNAi agents may include one or more non-natural RNA nucleotides (e.g., nucleotide analogs, DNA nucleotides, etc.). Inclusion of non-natural RNA nucleic acid residues may be used to make the RNAi agent more resistant to cellular degradation than RNA. In some embodiments, the term "RNAi agent" may refer to any RNA, RNA derivative, and/or nucleic acid encoding an RNA that induces an RNAi effect (e.g., degradation of target RNA and/or inhibition of translation). In some embodiments, an RNAi agent may comprise a blunt-ended (i.e., without overhangs) dsRNA that can act as a Dicer substrate. For example, such an RNAi agent may comprise a blunt-ended dsRNA which is ≥25 base pairs length, which may optionally be chemically modified to abrogate an immune response.

RNAi-inducing agent: As used herein, the term "RNAi-inducing agent" encompasses any entity that delivers, regulates, and/or modifies the activity of an RNAi agent. In some embodiments, RNAi-inducing agents may include vectors (other than naturally occurring molecules not modified by the hand of man) whose presence within a cell results in RNAi and leads to reduced expression of a transcript to which the RNAi-inducing agent is targeted. In some embodiments, RNAi-inducing agents are RNAi-inducing vectors. In some embodiments, RNAi-inducing agents are compositions comprising RNAi agents and one or more pharmaceutically acceptable excipients and/or carriers. In some embodiments, an RNAi-inducing agent is an "RNAi-inducing vector," which refers to a vector whose presence within a cell results in production of one or more RNAs that self-hybridize or hybridize to each other to form an RNAi agent (e.g. siRNA, shRNA, and/or miRNA). In various embodiments, this term encompasses plasmids, e.g., DNA vectors (whose sequence may comprise sequence elements derived from a virus), or viruses (other than naturally occurring viruses or plasmids that have not been modified by the hand of man), whose presence within a cell results in production of one or more RNAs that self-hybridize or hybridize to each other to form an RNAi agent. In general, the vector comprises a nucleic acid operably linked to expression signal(s) so that one or more RNAs that hybridize or self-hybridize to form an RNAi agent are transcribed when the vector is present within a cell. Thus the vector provides a template for intracellular synthesis of the RNA or RNAs or precursors thereof. For purposes of inducing RNAi, presence of a viral genome in a cell (e.g., following fusion of the viral envelope with the cell membrane) is considered sufficient to constitute presence of the virus within the cell. In addition, for purposes of inducing RNAi, a vector is considered to be present within a cell if it is introduced into the cell, enters the cell, or is inherited from a parental cell, regardless of whether it is subsequently modified or processed within the cell. An RNAi-inducing vector is considered to be targeted to a transcript if presence of the vector within a cell results in production of one or more RNAs that hybridize to each other or self-hybridize to form an RNAi agent that is targeted to the transcript, i.e., if presence of the vector within a cell results in production of one or more RNAi agents targeted to the transcript.

Short, interfering RNA (siRNA): As used herein, the term "short, interfering RNA" or "siRNA" refers to an RNAi agent comprising an RNA duplex (referred to herein as a "duplex region") that is approximately 19 base pairs (bp) in length and optionally further comprises one to three single-stranded overhangs. In some embodiments, an RNAi agent comprises a duplex region ranging from 15 bp to 29 bp in length and optionally further comprising one or two single-stranded overhangs. An siRNA may be formed from two RNA molecules that hybridize together, or may alternatively be generated from a single RNA molecule that includes a self-hybridizing portion. In general, free 5'-ends of siRNA molecules have phosphate groups, and free 3'-ends have hydroxyl groups. The duplex portion of an siRNA may, but typically does not, comprise one or more bulges consisting of one or more unpaired nucleotides. One strand of an siRNA includes a portion that hybridizes with a target transcript. In certain embodiments, one strand of the siRNA is precisely complementary with a region of the target transcript, meaning that the siRNA hybridizes to the target transcript without a single mismatch. In some embodiments, one or more mismatches between the siRNA and the targeted portion of the target transcript may exist. In some embodiments in which perfect complementarity is not achieved, any mismatches are generally located at or near the siRNA termini. In some embodiments, siRNAs mediate inhibition of gene expression by causing degradation of target transcripts.

Short hairpin RNA (shRNA): As used herein, the term "short hairpin RNA" or "shRNA" refers to an RNAi agent comprising an RNA having at least two complementary portions hybridized or capable of hybridizing to form a double-stranded (duplex) structure sufficiently long to mediate RNAi (typically at least approximately 19 bp in length), and at least one single-stranded portion, typically ranging between approximately 1 nucleotide (nt) and approximately 10 nt in length that forms a loop. In some embodiments, an shRNA comprises a duplex portion ranging from 15 bp to 29 bp in length and at least one single-stranded portion, typically ranging between approximately 1 nt and approximately 10 nt in length that forms a loop. The duplex portion may, but typically does not, comprise one or more bulges consisting of one or more unpaired nucleotides. In some embodiments, siRNAs mediate inhibition of gene expression by causing degradation of target transcripts. shRNAs are thought to be processed into siRNAs by the conserved cellular RNAi machinery. Thus shRNAs may be precursors of siRNAs. Regardless, siRNAs in general are capable of inhibiting expression of a target RNA, similar to siRNAs.

Small molecule: In general, a "small molecule" refers to a substantially non-peptidic, non-oligomeric organic compound either prepared in the laboratory or found in nature. Small molecules, as used herein, can refer to compounds that are "natural product-like," however, the term "small molecule" is not limited to "natural product-like" compounds. Rather, a small molecule is typically characterized in that it contains several carbon-carbon bonds, and has a molecular weight of less than 1500 g/mol, less than 1250 g/mol, less than 1000 g/mol, less than 750 g/mol, less than 500 g/mol, or less than 250 g/mol, although this characterization is not intended to be limiting for the purposes of the present invention. In certain other embodiments, natural-product-like small molecules are utilized.

Similarity: As used herein, the term "similarity" refers to the overall relatedness between polymeric molecules, e.g. between nucleic acid molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Vector: As used herein, "vector" refers to a nucleic acid molecule which can transport another nucleic acid to which it has been linked. In some embodiment, vectors can achieve extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION OF CERTAIN EMBODIMENTS OF THE INVENTION

The plasma membrane is a dynamic structure that can bud inward or outward to generate membrane-encapsulated vesicles (1, 2). Inward budding leads to the formation of endosomes, which can mediate the sorting and degradation of receptors and other plasma membrane proteins by a highly conserved ESCRT (Endosomal Sorting Complex Required for Transport) machinery that recognizes and guides ubiquitinated receptors from plasma membranes to late endosomes and then to lysosomes, where the receptors are degraded (for reviews, see refs (1, 3, 4)). Tumor susceptibility gene 101 (TSG101), an essential ESCRT component, is central to endosomal sorting (5, 6). Using a unique ubiquitin enzyme variant (UEV) domain that binds to ubiquitin and recognizes the tetrapeptide protein motif, PS/TAP (7-9), TSG101 interacts with the early endosomal protein Hrs (6, 10, 11) and late endosome-associated Alix (12), to mediate the trafficking of ubiquitinated receptors from early endosomes to late endosomes; there, additional ESCRT proteins and an ATPase (VPS4) drive the formation of, and delivery of endosomal cargo to, endosomal-membrane-derived vesicles known as multivesicular bodies (MVBs) (3, 13). Fusion of MVBs with lysosomes leads to degradation of the cargo, whereas trafficking and fusion of MVB-containing late endosomes with the plasma membrane deliver small vesicles termed "exosomes" into the extracellular space (2, 14, 15).

Outward budding of plasma membranes occurs during egress of budding viruses from cells. The best characterized example of viral budding, which hijacks the ESCRT machinery, involves the human immunodeficiency virus (HIV) (16-18). HIV budding is driven by the viral Gag protein, which localizes to the plasma membrane of host cells. In the "late domain" of HIV Gag is a critical PTAP motif that interacts with the UEV domain of TSG101 (19, 20), enabling Gag to recruit TSG101 and other ESCRT proteins, which normally reside on endosomal membranes, to the cell surface (12, 21, 22). By such recruitment, Gag can initiate plasma membrane budding. Disruption of the Gag/TSG101 interaction through either mutation of the PTAP motif in Gag or overexpression of mutant TSG101 can block the release of HIV viral particles (23-25). Many other viruses also recruit TSG101 or other ESCRT components to aid their budding at the cell surface (26, 27).

While viral budding and MVB formation are topologically similar in that both processes utilize the ESCRT machinery and involve the budding of membranes away from the cytosol, the two events are in fact functionally and structurally distinct. MVBs are formed by invagination of late endosome limiting membranes into the lumen of the organelle, whereas budding of viruses normally occurs at the cell surface and results in release of viral particles from the cytoplasm extracellularly (evagination). Thus, the analogy between MVB formation and viral budding (18, 26) is incomplete.

Some aspects of this invention relate to the discovery of an intrinsic cellular process, termed DPMB (direct plasma membrane budding) that underlies MVB-independent vesicle formation at the cell surface. As described in more detail elsewhere herein, DPMB involves the recruitment of TSG101 to the cell surface by the ARRDC1 protein and is mechanistically distinct from MVB formation and from MVB-related exosome formation, and leads directly to evagination of the plasma membrane and the release of a novel type of microvesicle, termed ARMM, into the extracellular space.

Microvesicles

Some aspects of this invention provide isolated arrestin domain-containing protein 1 (ARRDC1)-mediated microvesicles (ARMMs). Such ARMMs typically include a lipid bilayer and an ARRDC1 protein or fragment thereof. In some embodiments, an ARMM further includes a TSG101 protein or fragment thereof. In some embodiments, an ARMM includes additional or different markers, for example, proteins and molecules associated with the cellular ESCRT machinery.

ARRDC1

ARRDC1 is a protein that comprises a PSAP and a PPXY motif, also referred to herein as a PSAP and PPXY domain, respectively, in its C-terminus, and interacts with TSG101 as shown herein. Exemplary, non-limiting ARRDC1 protein sequences are provided herein, and additional, suitable ARRDC1 protein sequences, isoforms, and fragments according to aspects of this invention are known in the art. It will be appreciated by those of skill in the art that this invention is not limited in this respect. Exemplary ARRDC1 sequences include the following (PSAP and PPXY motifs are marked):

>gi|22748653|ref|NP_689498.1| arrestin domain-containing protein 1 [Homo sapiens]
(SEQ ID NO: 2)

MGRVQLFEISLSHGRVVYSPGEPLAGTVRVRLGAPLPFRAIRVTCIGSCGVSNKANDT

AWVVEEGYFNSSLSLADKGSLPAGEHSFPFQFLLPATAPTSFEGPFGKIVHQVRAAIH

```
TPRFSKDHKCSLVFYILSPLNLNSIPDIEQPNVASATKKFSYKLVKTGSVVLTASTDLR

GYVVGQALQLHADVENQSGKDTSPVVASLLQKVSYKAKRWIHDVRTIAEVEGAGV

KAWRRAQWHEQILVPALPQSALPGCSLIHIDYYLQVSLKAPEATVTLPVFIGNIAVNH

APVSPRPGLGLPPGAPPLVV[PSAP]PQEEAEAEAAAGGPHFLDPVFLSTKSHSQRQPLL

ATLSSVPGAPEPCPQDGSPASHPLHPPLCISTGATVPYFAEGSGGPVPTTSTLIL[PPEY]S

SWGYPYEAPPSYEQSCGGVEPSLTPES
```

>gi|244798004|ref|NP_001155957.1| arrestin domain-containing protein 1 isoform a [*Mus musculus*]

```
                                                  (SEQ ID NO: 3)
MGRVQLFEIRLSQGRVVYGPGEPLAGTVHLRLGAPLPFRAIRVTCMGSCGVSTKAND

GAWVVEESYFNSSLSLADKGSLPAGEHNFPFQFLLPATAPTSFEGPFGKIVHQVRASI

DTPRFSKDHKCSLVFYILSPLNLNSIPDIEQPNVASTTKKFSYKLVKTGNVVLTASTDL

RGYVVGQVLRLQADIENQSGKDTSPVVASLLQKVSYKAKRWIYDVRTIAEVEGTGV

KAWRRAQWQEQILVPALPQSALPGCSLIHIDYYLQVSMKAPEATVTLPLFVGNIAVN

QTPLSPCPGRESSPGTLSLVV[PSAP]PQEEAEAVASGPHFSDPVSLSTKSHSQQQPLSAP

LGSVSVTTTEPWVQVGSPARHSLHPPLCISIGATVPYFAEGSAGPVPTTSALIL[PPEY]S

SWGYPYEAPPSYEQSCGAAGTDLGLIPGS
```

>gi|244798112|ref|NP_848495.2| arrestin domain-containing protein 1 isoform b [*Mus musculus*]

```
                                                  (SEQ ID NO: 4)
MGRVQLFEIRLSQGRVVYGPGEPLAGTVHLRLGAPLPFRAIRVTCMGSCGVSTKAND

GAWVVEESYFNSSLSLADKGSLPAGEHNFPFQFLLPATAPTSFEGPFGKIVHQVRASI

DTPRFSKDHKCSLVFYILSPLNLNSIPDIEQPNVASTTKKFSYKLVKTGNVVLTASTDL

RGYVVGQVLRLQADIENQSGKDTSPVVASLLQVSYKAKRWIYDVRTIAEVEGTGVK

AWRRAQWQEQILVPALPQSALPGCSLIHIDYYLQVSMKAPEATVTLPLFVGNIAVNQ

TPLSPCPGRESSPGTLSLVV[PSAP]PQEEAEAVASGPHFSDPVSLSTKSHSQQQPLSAPL

GSVSVTTTEPWVQVGSPARHSLHPPLCISIGATVPYFAEGSAGPVPTTSALIL[PPEY]SS

WGYPYEAPPSYEQSCGAAGTDLGLIPGS
```

TSG101

Tumor susceptibility gene 101, also referred to herein as TSG101, is a protein encoded by this gene belongs to a group of apparently inactive homologs of ubiquitin-conjugating enzymes. The protein contains a coiled-coil domain that interacts with stathmin, a cytosolic phosphoprotein implicated in tumorigenesis. TSG101 is a protein that comprises a UEV domain, and interacts with ARRDC1 as shown herein. Exemplary, non-limiting TSG101 protein sequences are provided herein, and additional, suitable TSG101 protein sequences, isoforms, and fragments according to aspects of this invention are known in the art. It will be appreciated by those of skill in the art that this invention is not limited in this respect. Exemplary TSG101 sequences include the following:

>gi|5454140|ref|NP_006283.1| tumor susceptibility gene 101 protein [*Homo sapiens*]

```
                                                  (SEQ ID NO: 5)
MAVSESQLKKMVSKYKYRDLTVRETVNVITLYKDLKPVLDSYVFNDG

SSRELMNLTGTIPVPYRGNTYNIPICLWLLDTYPYNPPICFVKPTSS

MTIKTGKHVDANGKIYLPYLHEWKHPQSDLLGLIQVMIVVFGDEPPV
```

-continued

FSRPISASYPPYQATGPPNTSYMPGMPGGISPYPSGYPPNPSGYPGC

PYPPGGPYPATTSSQYPSQPPVTTVGPSRDGTISEDTIRASLISAVS

DKLRWRMKEEMDRAQAELNALKRTEEDLKKGHQKLEEMVTRLDQEVA

EVDKNIELLKKKDEELSSALEKMENQSENNDIDEVIIPTAPLYKQIL

NLYAEENAIEDTIFYLGEALRRGVIDLDVFLKHVRLLSRKQFQLRAL

MQKARKTAGLSDLY

>gi|11230780|ref|NP_068684.1| tumor susceptibility gene 101 protein [*Mus musculus*]

(SEQ ID NO: 6)
MAVSESQLKKMMSKYKYRDLTVRQTVNVIAMYKDLKPVLDSYVFNDG

SSRELVNLTGTIPVRYRGNIYNIPICLWLLDTYPYNPPICFVKPTSS

MTIKTGKHVDANGKIYLPYLHDWKHPRSELLELIQIMIVIFGEEPPV

FSRPTVSASYPPYTATGPPNTSYMPGMPSGISAYPSGYPPNPSGYPG

CPYPPAGPYPATTSSQYPSQPPVTTVGPSRDGTISEDTIRASLISAV

SDKLRWRMKEEMDGAQAELNALKRTEEDLKKGHQKLEEMVTRLDQEV

AEVDKNIELLKKKDEELSSALEKMENQSENNDIDEVIIPTAPLYKQI

LNLYAEENAIEDTIFYLGEALRRGVIDLDVFLKHVRLLSRKQFQLRA

LMQKARKTAGLSDLY

>gi|48374087|ref|NP_853659.2| tumor susceptibility gene 101 protein [*Rattus norvegicus*]

(SEQ ID NO: 7)
MAVSESQLKKMMSKYKYRDLTVRQTVNVIAMYKDLKPVLDSYVFNDG

SSRELVNLTGTIPVRYRGNIYNIPICLWLLDTYPYNPPICFVKPTSS

MTIKTGKHVDANGKIYLPYLHDWKHPRSELLELIQIMIVIFGEEPPV

FSRPTVSASYPPYTAAGPPNTSYLPSMPSGISAYPSGYPPNPSGYPG

CPYPPAGPYPATTSSQYPSQPPVTTAGPSRDGTISEDTIRASLISAV

SDKLRWRMKEEMDGAQAELNALKRTEEDLKKGHQKLEEMVTRLDQEV

AEVDKNIELLKKKDEELSSALEKMENQSENNDIDEVIIPTAPLYKQI

LNLYAEENAIEDTIFYLGEALRRGVIDLDVFLKHVRLLSRKQFQLRA

LMQKARKTAGLSDLY

The UEV domain in these sequences includes amino acids 1-145 (underlined in the sequences above). The structure of UEV domains is known to those of skill in the art (see, e.g., Owen Pornillos et al., Structure and functional interactions of the Tsg101 UEV domain, *EMBO J.* 2002 May 15; 21(10): 2397-2406, the entire contents of which are incorporated herein by reference).

In some embodiments, microvesicle, e.g., ARMMs, are provided that comprise an ARRDC1 protein fragment, and/or a TSG101 protein fragment. In some embodiments, fusion proteins are provided that comprise an ARRDC1 protein fragment and/or a TSG101 protein fragment. In some embodiments, expression construct are provided that encode an ARRDC1 protein fragment and/or a TSG101 protein fragment. In some embodiments, the ARRDC1 protein fragment is a C-terminal ARRDC1 protein fragment. In some embodiments, the ARRDC1 protein fragment comprises the PSAP motif and at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the ARRCD1 sequence. In some embodiments, the TSG101 protein fragment comprises a TSG101 UEV domain. In some embodiments, the TSG101 protein fragment comprises the UEV domain and comprises at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the TSG101 sequence.

In some embodiments, the inventive microvesicles, e.g., ARMMs, further comprise a cell surface protein, for example, an integrin, a receptor tyrosine kinase, a G-protein coupled receptor, or a membrane-bound immunoglobulin. Other cell surface proteins may also be included in an ARMM. Integrins, receptor tyrosine kinases, G-protein coupled receptors, and a membrane-bound immunoglobulins suitable for use with embodiments of this invention will be apparent to those of skill in the art and the invention is not limited in this respect. For example, in some embodiments, the integrin is an α1β1, α2β1, α4β1, α5β1, α6β1, αLβ2, αMβ2, αIIbβ3, αVβ3, αVβ5, αVβ6, or a α6β4 integrin. In some embodiments, the receptor tyrosine kinase is a an EGF receptor (ErbB family), insulin receptor, PDGF receptor, FGF receptor, VEGF receptor, HGF receptor, Trk receptor, Eph receptor, AXL receptor, LTK receptor, TIE receptor, ROR receptor, DDR receptor, RET receptor, KLG receptor, RYK receptor, or MuSK receptor. In some embodiments, the G-protein coupled receptor is a rhodopsin-like receptor, the secretin receptor, metabotropic glutamate/pheromone receptor, cyclic AMP receptor, frizzled/smoothened receptor, CXCR4, CCR5, or beta-adrenergic receptor.

Some aspects of this invention relate to the recognition that ARMMs are taken up by target cells, and ARMM uptake results in the release of the contents of the ARMM into the cytoplasm of the target cells. Some aspects of this invention relate to the recognition that this can be used to deliver an agent in ARMMs to the target cell or a population of target cells, for example, by contacting the target cell with ARMMs comprising the agent to be delivered. Accordingly, some aspects of this invention provide ARMMs that comprise an agent, for example, a recombinant nucleic acid, a recombinant protein, or a synthetic small molecule.

In some embodiments, the agent is an agent that effects a desired change in the target cell, for example, a change in cell survival, proliferation rate, a change in differentiation stage, a change in a cell identity, a change in chromatin state, a change in the transcription rate of one or more genes, a change in the transcriptional profile, or a post-transcriptional change in gene compression of the target cell. It will be understood by those of skill in the art, that the agent to be delivered will be chosen according to the desired effect in the target cell. For example, to effect a change in the differentiation stage of a target cell, for example, to reprogram a differentiated target cell into an embryonic stem cell-like stage, the cell is contacted, in some embodiments, with ARMMs with reprogramming factors, for example, Oct4, Sox2, c-Myc, and/or KLF4. Similarly, to effect the change in the chromatin state of a target cell, the cell is contacted, in some embodiments, with ARMMs containing a chromatin modulator, for example, a DNA methyltransferase, or a histone deacetylase. For another example, if survival of the target cell is to be diminished, the target cell, in some embodiments, is contacted with ARMMs comprising a cytotoxic agent, for example, a chemotherapeutic drug. Additional agents suitable for inclusion into ARMMs and for a ARMM-mediated delivery to a target cell or target cell population will be apparent to those skilled in the art, and the invention is not limited in this respect.

In some embodiments, the agent is included in the ARMMs by contacting cells producing the ARMMs with the agent. For example, if the agent is a small molecule, for example a therapeutic drug to be delivered to a target cell population within the body of a subject, ARMMs containing the drug are produced by contacting cells expressing ARRDC1 and TSG101 with the drug in an amount and for a time sufficient to generate ARMMs containing the drug. For another example, if the agent is a nucleic acid or a protein, ARMMs containing nucleic acid or the protein are produced by expressing the nucleic acid or the protein in cells expressing ARRDC1 and TSG101, for example, from a recombinant expression construct.

In some embodiments, the agent is conjugated to the ARRDC1 protein, the ARRDC1 fragment, the TSG101 protein, or the TSG101 fragment. In some embodiments, where the agent is a protein, the protein may be conjugated to the ARRDC protein, the ARRDC1 fragment, the TSG101 protein, or the TSG101 fragment, by expressing the protein agent as a fusion with the ARRDC1 protein, the ARRDC1 fragment, the TSG101 protein, or the TSG101 fragment.

In some embodiments, ARMMs are provided that include a recombinant or a synthetic nucleic acid. Such ARMMs can be used to deliver the recombinant or synthetic nucleic acids to a target cell or target cell population. In some embodiments, the recombinant nucleic acid comprises an RNA, for example, an RNA encoding a protein (e.g., an mRNA), or a non-coding RNA. In some embodiments, the nucleic acid comprises an RNAi agent, for example, an antisense RNA, a small interfering RNA (siRNA), a small hairpin RNA (shRNA), a microRNA (miRNA), a small nuclear RNA (snRNA), a small nucleolar RNA (snoRNA), or a long intergenic non-coding RNA (lincRNA), or a precursor thereof. Some embodiments, ARMMs are provided that include a recombinant structural RNA, a ribozyme, or a precursor thereof.

Coding RNAs, RNAi agents, structural RNAs, and ribozymes, as well as precursors thereof, are well known to those skilled in the art and suitable RNAs and RNAi agents according to aspects of this invention will be apparent to the skilled artisan. It will be appreciated that the invention is not limited in this respect. ARMMs including RNA can be used to express the RNA function in a target cell without the need for genetic manipulation of the target cell. For example, ARMMs including protein-encoding nucleic acids can be used to express the encoded protein in a target cell or cell population upon ARMMs uptake without the need to genetically manipulate the target cell or cell population. For another example, ARMMs including an RNAi agent can be used to knock down a gene of interest in the target cell or the target cell population without the need to genetically amended claims department cell or cell population. For a third example, ARMMs including a ribozyme can be used to modulate the expression of a target nucleic acid, or to edit a target mRNA and a target cell without the need for genetic manipulation.

In some embodiments, ARMMs are provided that include a DNA, for example, a vector including an expression construct, a LINE sequence, a SINE sequence, a composite SINE sequence, or an LTR-retrotransposon sequence. ARMMs containing DNA allow for the transfer of genes or DNA elements from cell to cell, or, in some embodiments, for the targeted insertion of genes or DNA elements into a target cell or target cell type, for example a pathological target cell type in a subject. In some embodiments, ARMMs are provided that include a DNA encoding a protein. In some embodiments, ARMMs are provided that include a DNA encoding a non-coding RNA, for example, an antisense RNA, a small interfering RNA (siRNA), a small hairpin RNA (shRNA), a microRNA (miRNA), a small nuclear RNA (snRNA), a small nucleolar RNA (snoRNA), or a long intergenic non-coding RNA (lincRNA), or a precursor thereof. In some embodiments, the use of ARMMs containing a DNA has the advantage that a higher level of expression or a more sustained expression of the encoded protein or RNA can be achieved in a target cell as compared to direct delivery of the protein or RNA. In some embodiments, the DNA included in the ARMMs comprises a cell type specific promoter controlling the conscription of the encoded protein or RNA. The use of a cell type specific promoter allows for the targeted expression of the proteins were RNA encoded by the ARMM-delivered DNA, which can be used, for example in some therapeutic embodiments, to minimize the effect on subpopulations that are not targeted but may take up ARMMs.

In some embodiments, ARMMs are provided that include a detectable label. Such ARMMs allow for the labeling of a target cell without genetic manipulation. Detectable labels suitable for direct delivery to target cells are known in the art, and include, but are not limited to, fluorescent proteins, fluorescent dyes, membrane-bound dyes, and enzymes, for example, membrane-bound enzymes, catalyzing the reaction resulting in a detectable reaction product. Detectable labels suitable according to some aspects of this invention further include membrane-bound antigens, for example, membrane-bound ligands that can be detected with commonly available antibodies or antigen binding agents.

In some embodiments, ARMMs are provided that comprise a therapeutic agent. It will be appreciated, that any therapeutic agent that can be introduced into a cell shedding ARMMs or that can be packaged into synthetic ARMMs is suitable for inclusion into ARMMs according to some aspects of this invention. Suitable therapeutic agents include, but are not limited to, small organic molecules, also referred to as small molecules, or small compounds, and biologics, for example, therapeutic proteins, or protein fragments. Some non-limiting examples of therapeutic agents suitable for inclusion in ARMMs include antibacterial agents, antifungal antibiotics, antimyobacterials, neuraminidase inhibitors, antineoplastic agents, cytotoxic agents, cholinergic agents, parasympathomimetics, anticholinergic agents, antidepressants, antipsychotics, respiratory and cerebral stimulants, proton pump inhibitors, hormones and synthetic substitutes, receptor ligands, kinase inhibitors, chemotherapeutic agents, signaling molecules, kinases, phosphatases, proteases, RNA editing enzymes, nucleases, and zinc finger proteins, In some embodiments, ARMMs are provided that comprise a protein to be delivered to a target cell. In some embodiments, the protein is or comprises a transcription factor, a transcriptional repressor, a fluorescent protein, a kinase, a phosphatase, a protease, a ligase, a chromatin modulator, or a recombinase. In some embodiments, the protein is a therapeutic protein. In some embodiments the protein is a protein that effects a change in the state or identity of a target cell. For example, in some embodiments, the protein is a reprogramming factor. Suitable transcription factors, transcriptional repressors, fluorescent proteins, kinases, phosphatases, proteases, ligases, chromatin modulators, recombinases, and reprogramming factors are known to those skilled in the art, and the invention is not limited in this respect.

In some embodiments, ARMMs are provided that comprise an agent, for example, a small molecule, a nucleic acid, or a protein, that is covalently or non-covalently bound, or conjugated, to an ARRDC1 protein or fragment thereof, or a TSG101 protein or fragment thereof. In some embodiments, agent is conjugated to the ARRDC1 protein or fragment thereof, or the TSG101 protein or fragment thereof, via a linker. The linker may be cleavable or uncleavable. In some embodiments, the linker comprises an amide, ester, ether, carbon-carbon, or disulfide bond, although any covalent bond in the chemical art may be used. In some embodiments, the linker comprises a labile bond, cleavage of which results in separation of the supercharged protein from the peptide or protein to be delivered. In some embodiments, the linker is cleaved under conditions found in the target cell (e.g., a specific pH, a reductive environment, or the presence of a cellular enzyme). In some embodiments, the linker is cleaved by a cellular enzyme. In some embodiments, the cellular enzyme is a cellular protease or a cellular esterase. In some embodiments, the cellular protease is a cytoplasmic protease, an endosomal protease, or an endosomal esterase. In some embodiments, the cellular enzyme is specifically expressed in a target cell or cell type, resulting in preferential or specific release of the functional protein or peptide in the target cell or cell type. The target sequence of the protease may be engineered into the linker between the agent to be delivered and the ARRDC1 protein or the TSG101 protein or fragment thereof. In some embodiments, the target cell or cell type is a cancer cell or cancer cell type, a cell or cell type of the immune system, or a pathologic or diseased cell or cell type, and the linker is cleaved by an enzyme or based on a characteristic specific for the target cell. In some embodiments, the linker comprises an amino acid sequence chosen from the group including AGVF (SEQ ID NO: 33), GFLG (SEQ ID NO: 34), FK (SEQ ID NO: 35), AL, ALAL, or ALALA (SEQ ID NO: 36). Other suitable linkers will be apparent to those of skill in the art. In some embodiments, the linker is a cleavable linker. In some embodiments, the linker comprises a protease recognition site. In certain embodiments, the linker is a UV-cleavable moiety. Suitable linkers, for example, linkers comprising a protease recognition site, or linkers comprising a UV cleavable moiety are known to those of skill in the art. In some embodiments, the agent is conjugated to the ARRDC1 protein or fragment thereof, or the TSG101 protein or fragment thereof, via a sortase reaction, and the linker comprises an LPXTG motif. Methods and reagents for conjugating agents according to some aspects of this invention to proteins are known to those of skill in the art. Accordingly, suitable method for conjugating and agents to be included in an ARMM to an ARRDC1 protein or fragment thereof or a TSG101 protein or fragment thereof will be apparent to those of skill in the art based on this disclosure.

Methods for isolating ARMMs are also provided herein. One exemplary method includes collecting the culture medium, or supernatant, of a cell culture comprising microvesicle-producing cells. In some embodiments, the cell culture comprises cells obtained from a subject, for example, cells suspected to exhibit a pathological phenotype, e.g., a hyperproliferative phenotype. In some embodiments, the cell culture comprises genetically engineered cells producing ARMMs, for example, cells expressing a recombinant ARMM protein, for example, a recombinant ARRDC1 or TSG101 protein, such as an ARRDC1 or TSG101 fusion protein. In some embodiments, the supernatant is pre-cleared of cellular debris by centrifugation, for example, by two consecutive centrifugations of increasing G value (e.g., 500 G and 2000 G). In some embodiments, the method comprises passing the supernatant through a 0.2 μm filter, eliminating all large pieces of cell debris and whole cells. In some embodiments, the supernatant is subjected to ultracentrifugation, for example, at 120,000 g for 2 h, depending on the volume of centrifugate. The pellet obtained comprises microvesicles. In some embodiments, exosomes are depleted from the microvesicle pellet by staining and/or sorting (e.g., by FACS or MACS) using an exosome marker as described herein. Isolated or enriched ARMMs can be suspended in culture media or a suitable buffer, as described herein.

Fusion Proteins

Some aspects of this invention provide ARRDC1 fusion proteins that comprise an ARRDC1 protein or a fragment thereof, and a polypeptide conjugated to the ARRDC1 protein or fragment thereof. In some embodiments, the ARRDC1 fragment comprises a PSAP motif or domain (comprising the amino acid sequence PSAP (SEQ ID NO: 37)). In some embodiments, the ARRDC1 protein fragment comprises the PSAP motif and at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the ARRCD1 sequence.

Some aspects of this invention provide TSG101 fusion proteins, comprising an TSG101 protein or a fragment thereof, and a polypeptide conjugated to the TSG101 protein or fragment thereof. In some embodiments, the TSG101 fragment comprises a UEV domain. UEV domains are well known to those of skill in the art, and exemplary UEV domains are described herein (e.g., the 145 N-terminal amino acids of the human, rat, and mouse TSG101 protein sequence provided herein. Additional UEV domain sequences will be apparent to those of skill in the art, and the invention is not limited in this respect. In some embodiments, the TSG101 protein fragment comprises the UEV domain and at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the TSG101 sequence.

In some embodiments, the polypeptide is fused to the C terminus of the ARRDC1 protein or protein fragment, or to the C terminus of the TSG101 protein or protein fragment. In some embodiments, the polypeptide is fused to the N terminus of the ARRDC1 protein or protein fragment, or to the C terminus of the TSG101 protein or protein fragment.

In some embodiments, the polypeptide fused to the ARRDC1 protein or protein fragment or to the TSG101 protein or protein fragment comprises a transcription factor, a transcriptional repressor, a fluorescent protein, a kinase, a phosphatase, a protease, a chromatin modulator, a ligase, or a recombinase.

In some embodiments, the polypeptide is conjugated to the ARRDC1 protein, the ARRDC1 protein fragment, the TSG101 protein, or the TSG101 protein fragment via a covalent bond. In some embodiments, the polypeptide is conjugated to the ARRDC1 protein, the ARRDC1 protein fragment, the TSG101 protein, or the TSG101 protein fragment via a linker. In some embodiments, the linker is a cleavable linker. In some embodiments, the linker comprises a protease recognition site or a UV-cleavable moiety. Some embodiments, the protease recognition site is recognized by a protease expressed in a target cell, resulting in the polypeptide fused to the ARRDC1 protein or fragment thereof or the TSG101 protein fragment thereof being released into the cytoplasm of the target cell upon uptake of the ARMM.

Cells Producing Microvesicles

Some aspects of this invention provide a microvesicle-producing cell that comprises a recombinant expression construct encoding an ARRDC1 protein, or a PSAP domain-comprising fragment thereof under the control of a heterologous promoter. Some aspects of this invention provide a microvesicle-producing cell that comprises a recombinant expression construct encoding a TSG101 protein, or a UEV domain-comprising fragment thereof, under the control of a heterologous promoter.

In some embodiments, the expression construct comprised in the microvesicle producing cell further encodes a polypeptide fused to the ARRDC1 protein or the TSG101 protein. In some embodiments, ARMMs produced by such a cell comprise the encoded fusion protein. In some embodiments, the polypeptide comprises a transcription factor, a transcriptional repressor, a fluorescent protein, a kinase, a phosphatase, a protease, a ligase, or a recombinase.

In some embodiments, the cell further comprises a recombinant expression construct encoding a protein. In some embodiments, the encoded protein comprises a transcription factor, a transcriptional repressor, a fluorescent protein, a chromatin modulator, a kinase, a phosphatase, a protease, a ligase, or a recombinase. ARMMs produced by such a cell typically comprise the protein encoded by the expression construct.

In some embodiments, the cell further comprises a recombinant expression construct encoding an RNAi agent. In some embodiments, ARMMs produced by such a cell comprise the RNAi agent encoded by the expression construct. In some embodiments, the RNAi agent is an RNAi agent as described herein, for example, a nucleic acid, a non-coding RNA, an antisense RNA, a small RNA, an siRNA, an shRNA, a microRNA, an snRNA, a snoRNA, a lincRNA, or a precursor thereof.

In some embodiments, the cell further comprises a recombinant expression construct encoding a ribozyme. In some embodiments, the ribozyme is a cis-splicing ribozyme. In some embodiments, the ribozyme is a trans-splicing ribozyme.

In some embodiments, the expression construct is stably inserted into the genome of the cell. In some embodiments, the expression construct is maintained in the cell, but not inserted into the genome of the cell. In some embodiments, the expression construct is comprised in a vector, for example, a plasmid vector, a cosmid vector, a viral vector, or an artificial chromosome. In some embodiments, the expression construct further comprises additional sequences or elements that facilitate the maintenance and/or the replication of the expression construct in the microvesicle-producing cell, or that improve the expression of the ARRDC1 protein or fragment thereof in the cell. Such additional sequences or elements may include, for example, an origin of replication, and antibiotic resistance cassette, a poly a sequence, or a transcriptional isolator. Some expression constructs suitable for the generation of microvesicle producing cells according to aspects of this invention are described elsewhere herein. Methods and reagents for the generation of additional expression constructs suitable for the generation of microvesicle producing cells according to aspects of this invention will be apparent to those of skill in the art based on the present disclosure.

In some embodiments, the microvesicle producing cell is a mammalian cell, for example, a mouse cell, a rat cell, a hamster cell, a rodent cell, or a nonhuman primate cell. In some embodiments, the microvesicle producing cell is a human cell.

Methods of Microvesicle-Mediated Agent Delivery

Some aspects of this invention provide a method of delivering an agent, for example, a therapeutic agent, a small molecule, a protein, or a nucleic acid, to a target cell. The target cell can be contacted with an ARMM in different ways. For example, in some embodiments, a target cell is contacted directly with an ARMM as described herein, for example, with an isolated ARMM shed by a microvesicle producing cell, or with an isolated ARMM. The contacting can be done in vitro by administering the ARMM to the target cell in a culture dish, or in vivo by administering the ARMM to a subject harboring the target cell. Alternatively, the target cell can be contacted with a microvesicle producing cell as described herein, for example, in vitro by co-culturing the target cell and the microvesicle producing cell, or in vivo by administering a microvesicle producing cell to a subject harboring the target cell.

Accordingly, in some embodiments, the method comprises contacting the target cell with a microvesicle, for example, an ARMM comprising the agent to be delivered, as described herein. In some embodiments, the method comprises contacting the target cell with a microvesicle-producing cell as described herein. In some embodiments, the method comprises contacting the target cell with an isolated microvesicle that comprises a lipid bilayer, an ARRDC1 protein or fragment thereof, and the agent.

In some embodiments, the target cell is a mammalian cell, for example, a mouse cell, a rat cell, hamster cell, a rodent cell, or a nonhuman primate cell. In some embodiments, the target cell is a human cell. In some embodiments, the target cell is a stem cell. In some embodiments, the target cell is a cell in vitro, and the method comprises administering the microvesicle to the cell in vitro, or co-culturing the target cell with the microvesicle-producing cell in vitro. In some embodiments, the target cell is a cell in a subject, and the method comprises administering the microvesicle or the microvesicle-producing cell to the subject.

In some embodiments, the subject is a mammalian subject, for example, a rodent, a mouse, a rat, a hamster, or a non-human primate. In some embodiments, the subject is a human subject.

In some embodiments, the target cell is a pathological cell. In some embodiments, the target cell is a cancer cell. In some embodiments, the microvesicle is conjugated to a binding agent that selectively binds an antigen of the target cell. In some embodiments, the antigen of the target cell is a cell surface antigen. In some embodiments, the binding agent is a membrane-bound immunoglobulin, an integrin, a receptor, or a receptor ligand. Suitable surface antigens of target cells, for example of specific target cell types, e.g. cancer cells, are known to those of skill in the art, as are suitable binding agents that specifically bind such antigens. Methods for producing membrane-bound binding agents, for example, membrane-bound immunoglobulin, for example membrane-bound antibodies or antibody fragments specifically binding a surface antigen expressed on the cell surface of cancer cells, are also known to those of skill in the art. The choice of the binding agent will depend, of course, on the identity or the type of the target cell. Cell surface antigens specifically expressed on various types of cells that can be targeted by ARMMs comprising membrane-bound binding agents will be apparent to those of skill in the art. It will be appreciated, that the present invention is not limited in this respect.

Co-Culture Systems

Some aspects of this invention provide in vitro cell culture systems comprising at least two types of cells: microvesicle producing cells and target cells that take up the microvesicles produced. Accordingly, in the co-culture systems provided herein, there is a shuffling of the contents of the microvesicles produced to the target cells. Such co-culture systems allow for the expression of a gene product or multiple gene products generated by the microvesicle producing cells in the target cells without genetic manipulation of the target cells.

In some embodiments, a co-culture system is provided that comprises (a) a microvesicle-producing cell population, comprising a recombinant expression construct encoding (i) an ARRDC1 protein or fragment thereof under the control of a heterologous promoter, and/or (ii) a TSG101 protein or fragment thereof under the control of a heterologous promoter; and (b) a target cell population. In some embodiments, the ARRDC1 fragment comprises a PSAP motif, and/or the TSG101 fragment comprises a UEV domain. In some embodiments, the expression construct further encodes a polypeptide fused to the ARRDC1 protein or fragment thereof. In some embodiments, the expression construct further encodes a polypeptide fused to the TSG101 protein or fragment thereof. In some embodiments, the host cell comprises a plurality of expression constructs encoding a plurality of ARRDC1 fusion proteins and/or TSG101 fusion proteins. In some embodiments, the polypeptide fused to the ARRDC1 protein or fragment, or to the TSG101 protein or fragment, independently comprises a transcription factor, a transcriptional repressor, a fluorescent protein, a kinase, a phosphatase, a protease, a chromatin modulator, a ligase, or a recombinase.

One exemplary application of a co-culture system as provided herein is the programming or reprogramming of a target cell without genetic manipulation. For example, in some embodiments, the target cell if a differentiated cell, for example, a fibroblast cell. In some embodiments, the microvesicle producing cells, are feeder cells, or non-proliferating cells. In some embodiments, the microvesicle producing cells produce ARMMs comprising a reprogramming factor, or a plurality of reprogramming factors, either as isolated proteins or as fusion proteins with ARRDC1 or TSG101 proteins or fragments. In some embodiments, co-culture of the differentiated target cells with the microvesicle producing cells results in the reprogramming of the differentiated target cells to an embryonic state. In some embodiments, co-culture of the differentiated target cells with the microvesicle producing cells results in the programming, or trans-differentiation, of the target cells to a differentiated cell states that is different from the original cell state of the target cells. For example, in some embodiments, the target cells are fibroblast cells, and the microvesicle producing cells express a transcription factor the expression of which can reprogram fibroblast cells to a neuronal state.

Another exemplary application of a co-culture system as provided herein is the directed differentiation of embryonic stem cells. In some embodiments, the target cells are undifferentiated embryonic stem cells, and the microvesicle producing cells express one or more differentiation factors, for example signaling molecules, or transcription factors, that trigger or facilitate the differentiation of the embryonic stem cells into differentiated cells of a desired lineage, for example neuronal cells, or mesenchymal cells.

Yet another exemplary application of a co-culture system as provided herein is the maintenance of stem cells, for example, of embryonic stem cells or of adult stem cells in an undifferentiated state in vitro. In some such embodiments, the microvesicle producing cells express signaling molecules and/or transcription factors that promote stem cell maintenance and/or inhibit stem cell differentiation. In some embodiments, the microvesicle producing cells thus create a microenvironment for the stem cells that mimics a naturally occurring stem cell niche in vitro.

In some embodiments, the microvesicle-producing cell is a mammalian cell. In some embodiments, the microvesicle-producing cell is a non-proliferating cell. In some embodiments, the microvesicle-producing cell is a feeder cell. In some embodiments, the target cell is a mammalian cell. In some embodiments, the target cell is a human cell. In some embodiments, the target cell is a differentiated cell. In some embodiments, the target cell is a stem cell.

Methods of Microvesicle-Based Diagnostics

Some aspects of this invention provide a method of detecting a condition in a subject based on the presence or absence of ARMMs, or based on the presence or absence of a biomarker or a biomarker profile in ARMMs obtained from the subject. In some embodiments, the method comprises (a) obtaining an ARMM from the subject; and (b) detecting a biomarker profile indicative of the condition in the ARMM obtained from the subject; wherein the presence of the biomarker profile in the ARMM obtained from the subject indicates the presence of the condition in the subject.

Some aspects of this invention provide a method of detecting a pathological cell or cell population in a subject based on the presence or absence or the level of ARMMs, or based on the presence or absence of a biomarker or a biomarker profile in ARMMs obtained from the subject. In some embodiments, the method comprises (a) detecting a level of ARMMs produced by a cell or cell population obtained from the subject; and (b) comparing the level of ARMMs of (a) to a control level, wherein, if the level of ARMMs produced by the cell or cell population obtained from the subject is higher than the control level, then the cell or cell population is indicated to be a pathological cell or cell population. In some embodiments, the method comprises (a) obtaining an ARMM from the subject; and (b) detecting a biomarker profile indicative of the pathological cell or cell population in the ARMM obtained from the subject; wherein the presence of the biomarker profile in the ARMM obtained from the subject indicates the presence of the pathological cell or cell population condition in the subject.

In some embodiments, the method further comprises obtaining a sample from the subject that comprises an ARMM. In some embodiments, the method further comprises obtaining a sample from the subject comprising a cell or cell population producing ARMMs. In some embodiments, the pathological cell or cell population is a malignant cell or cell population. In some embodiments, the pathological cell or cell population produces an increased amount of ARMMs as compared to a normal or control cell or cell population. In some embodiments, a subject having a disease harbors an increased amount of ARMMs in the diseased tissue, or systemically, as compared to a healthy or control subject. In some embodiments, an increased amount of ARMMs is amount of ARMMs that is increased at least about 2-fold, at least about 3-fold, at least about 4-fold, at least about 5-fold, at least about 10-fold, at least about 20-fold, at least about 25-fold, at least about 50-fold, at least about 100-fold, at least about 1,000-fold, at least about 10,000-fold, at least about 100,000-fold, or at least to about 1,000,000-fold as compared to a control cell population or control subject.

Expression Constructs

Some aspects of this invention provide an expression constructs that induce or facilitate the generation of ARMMs in cells harboring such a construct. In some embodiments, the expression constructs encode and ARRDC1 protein or fragment thereof and/or a TSG101 protein or fragment thereof. In some embodiments, overexpression of either or both of these gene products in a cell in use or increase the production of ARMMs in the cell, thus turning the cell into a microvesicle producing cell. In some embodiments, the expression constructs allows for the cloning of a polypeptide to be fused to the ARRDC1 protein or protein fragments or to the TSG101 protein or protein fragment. In some embodiments, such an expression construct comprises a restriction or recombination sites that allows in-frame cloning of a nucleotide sequence encoding the polypeptide to be fused, either at the C terminus, or at the N terminus of the encoded ARRDC1 and/or TSG101 protein or protein fragment.

In some embodiments, the expression constructs comprises (a) a nucleotide sequence encoding an ARRDC1 protein or fragment thereof operably linked to a heterologous promoter, and (b) a restriction site or a recombination site positioned adjacent to the ARRDC1-encoding nucleotide sequence allowing for the insertion of a nucleotide sequence encoding an additional polypeptide in frame with the ARRDC1-encoding nucleotide sequence. Some aspects of this invention provide an expression construct comprising (a) a nucleotide sequence encoding a TSG101 protein or fragment thereof operably linked to a heterologous promoter, and (b) a restriction site or a recombination site positioned adjacent to the TSG101-encoding nucleotide sequence allowing for the insertion of a nucleotide sequence encoding an additional polypeptide in frame with the TSG101-encoding nucleotide sequence.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Materials and Methods

ARMMs Isolation and Transfer.

Culture media atop nascent or transfected cells were collected and precleared of cellular debris by two consecutive centrifugations (500 g and 2000 g). Media were then passed through a 0.2 μm filter (Sarstedt) and subjected to ultracentrifugation using the Beckman LTA110 rotor in an Optima LTX centrifuge (Beckman), or using the SW41 Ti rotor in a L8-M centrifuge (Beckman) at 120,000 g for 2 h, depending on the volume of centrifugate. Media were then aspirated and pellets were washed twice with ice cold phosphate buffered saline (PBS). ARMMs were then resuspended either in 1.3× Lithium dodecyl sulfate (LDS; Invitrogen) supplemented with β-mercaptoethanol (β-ME) or in PBS. To calibrate ARMMs production with cell number, protein concentrations of the corresponding cytosolic lysates were measured using the Protein 660 nm assay (Pierce). For ARMMs transfer assays, transfected cells were washed thoroughly and seeded atop a 0.4 μm transwell membrane (Costar) for 16 h before transferring transwell to a plate containing untransfected 293T cells. ARMMs transfer was allowed to proceed for 30 h before harvesting. Alternatively, purified ARMMs resuspended in PBS were added to culture media containing untransfected 293T cells and incubated for 24-30 h before harvesting.

Immunogold Labeling and Electron Microscopy.

For immunogold staining of budding vesicles or vesicles in intercellular spaces, cells were washed, gently detached with 0.5 mM EDTA, and layered on a cushion of 8% PFA in 0.1 M sodium phosphate buffer. Cell pellets were collected by centrifugation at 3000 RPM for 3 min and pellets were replenished with 4% PFA fixative for 2 h at room temperature before freezing and processing for visualization.

Yeast Two-Hybrid Screen.

The two-hybrid screen was done as previously described (6) using the UEV domain of TSG101 (amino acid residue 1-145) as the bait.

Cell Culture and Transfections.

HEK293T, HeLa and A549 cells were cultured in Dulbecco's Modified Eagle Medium (DMEM; Invitrogen) supplemented with 10% Fetal Bovine Serum (FBS; Invitrogen) and 20 mM HEPES (Invitrogen). Cells were maintained at 37° C. with 5% $CO_2$. Plasmid transfections were carried out using Fugene 6 (Roche). siRNA transfections used Dharmafect I (Dharmacon).

Plasmid Constructs.

HA- and Flag-tagged ARRDC1 expression constructs have been described previously (40). Mutant derivatives of the constructs were made by site-directed mutagenesis (QuikChange kit; Stratagene). EGFP fusion constructs were made by cloning of target genes into pEGFP-N1 (CLONTECH). mCherry-expressing constructs were made by cloning of fused mCherry-target gene fragments into pCI-neo vector (Promega). pEGFPN1-VPS4a and the VPS4a-E228Q dominant negative mutant constructs were provided by Wesly Sundquist (University of Utah). GFP-tagged WWP2 constructs were obtained from Daniela Rotin (University of Toronto Antibodies.

Antibodies were obtained as follows: anti-FLAG HRP-conjugated (Sigma); anti-HA HRP-conjugated (Roche); anti-β-actin (Santa Cruz Biotech); anti-GFP (Invitrogen); anti-TSG101 (Genetex); anti-LAMP1 (Transduction Labs); anti-LAMP3/CD63 (for immunoblotting or immunogold labeling: Santa Cruz Biotech; for immunogold labeling: BD Pharmingen); anti-mCherry (Genetex); anti-WWP2 (Bethyl Labs); anti-ARRDC1 (raised by us in rabbits against purified 6×His-ARRDC1). For immunoprecipitation, anti-FLAG M2 or anti-HA EZview beads (Sigma) were used as indicated.

Western Blotting and Immunoprecipitation.

Cells were lysed in NP-40 lysis buffer (0.5% NP-40, 50 mM TrisCl, 150 mM NaCl) supplemented with a protease inhibitor cocktail (Roche). Lysates or ARMMs resuspended in LDS sample buffer were typically resolved on a 4-12% Nupage gel (Invitrogen) using MOPS running buffer supplemented with Nupage antioxidant (Invitrogen) before transfer onto a nitrocellulose membrane (GE Amersham) and probing with the indicated antibodies. For immunoprecipitation of cytosolic proteins, 200-300 µg of cell lysate was pre-cleared with protein A agarose beads (Santa Cruz Biotech) followed by overnight incubation at 4° C. with bait-specific antibodies conjugated to beads. Beads are then washed twice for 10 mins in lysis buffer and eluted in 2×LDS sample buffer supplemented with 10% β-ME for Western blot analysis. For immunoprecipitation of ARMMs associated proteins, ARMMs were prepared as described above and then lysed in NP-40 lysis buffer for immunoprecipitation of the bait, as described for cellular proteins.

Confocal Microscopy.

Cells grown on glass cover slips were washed twice with PBS then incubated in 4% paraformaldehyde (PFA) for 10 min at room temperature. To quench PFA-derived auto-fluorescence cells were washed three times in Tris buffered saline (TBS) containing 1 mM $CaCl_2$ before being mounted on glass slides using the Vectashield mounting medium (Vector Labs). Image acquisition was carried out using a Leica TCS-NT laser scanning confocal microscope (Leica) equipped with air-cooled argon and krypton lasers. Images were then processed using ImageJ (NIH).

Electron Microscopy.

For microvesicle visualization, an aliquot from ARMMs preparation in PBS (5-10 µl) was adsorbed for 1 min to a carbon-coated grid. Excess liquid was removed with Whatman #1 filter paper (Whatman) followed by staining for 30 s with 0.75% uranyl formate. Adsorbed ARMMs were examined on a JEOL 1200EX transmission electron microscope and images were recorded with an AMT 2 k CCD camera. For immunogold staining of ARMMs, a microvesicle pellet was fixed in 4% PFA for 2 h, resuspended in 20% gelatin and infiltrated with 2.3 M sucrose in PBS containing 0.2 M glycine for 15 min to quench free aldehyde groups. Frozen samples were sectioned (80-90 nm sections) at −120° C. and sections were transferred to formvar carbon-coated grids for staining. Primary staining was carried out in 1% BSA with the indicated antibodies before washing four times with PBS and incubation with Protein A gold beads (5 nm). Stained grids were contrasted and embedded with 0.3% uranyl acetate in 2% methyl cellulose for 10 mins. Grids were examined as described above. For visualization of ARMMs budding and for assessment of ARMMs numbers (FIG. 2D), transfected cells were incubated in fixing solution (2.5% glutaraldehyde, 1.25% PFA, and 0.03% picric acid in 0.1M sodium cacodylate buffer, pH 7.4) for 2 h at room temperature. The cell pellet was then washed in 0.1 M cacodylate buffer, post-fixed in a solution containing osmium tetroxide ($OsO_4$) and 1.5% potassium ferrocyanide, and then treated with 1% aqueous uranyl acetate. Samples were then dehydrated, treated for 1 h with propylene oxide and soaked overnight in a 1:1 mixture of propylene oxide and TAAB Epon (Marivac Canada) before polymerization in TAAB Epon at 60° C. for 48 h. Ultrathin sections (80-90 nm) were obtained using a Reichert Ultracut-S microtome and mounted on copper grids stained with lead citrate. Samples were examined as above.

Results

ARRDC1 Recruits TSG101 to the Plasma Membrane.

Using a yeast two-hybrid screen and the UEV domain of TSG101 as the bait, we identified two independent clonal isolates that correspond to the C-terminal fragments of human arrestin-domain-containing protein, ARRDC1 (FIG. 1A). This finding is consistent with a previous study that reported co-immunoprecipitation of ARRDC1 with TSG101 (28). ARRDC1 contains a highly conserved PSAP motif (FIG. 1B), and mutational alteration of this motif to PAAP (SEQ ID NO: 32) markedly reduced the interaction between ARRDC1 and TSG101 (FIG. 1C). Additionally a mutation of amino acid residue methionine 95 of TSG101, which is known to be required for PS/TAP binding (7, 8), abolished the ARRDC1/TSG101 interaction (FIG. 1D). Together, these results demonstrate that ARDDC1 interacts with TSG101 through specific UEV/PSAP binding.

Figure 7A:
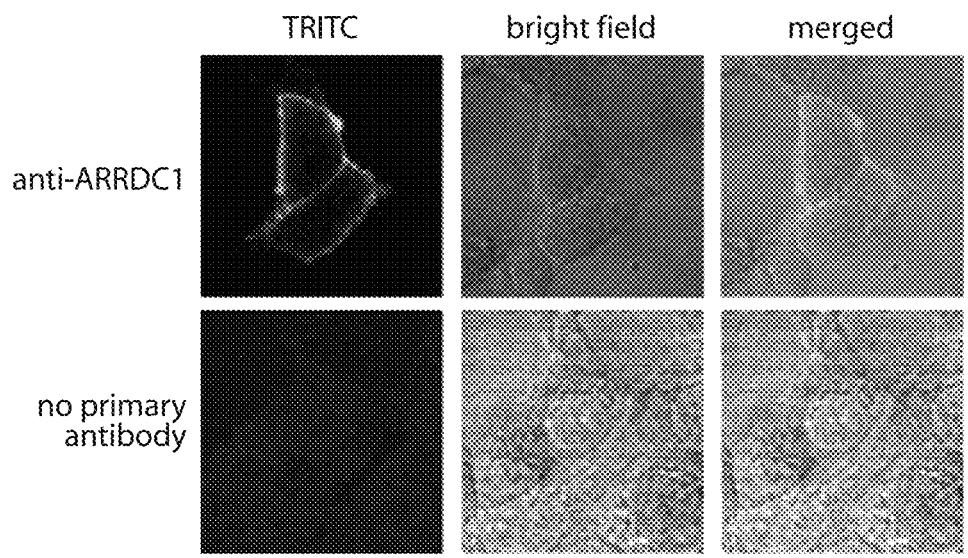
FIGS. 7A-7B. Plasma membrane localization of ARRDC1.
Figure 7B:
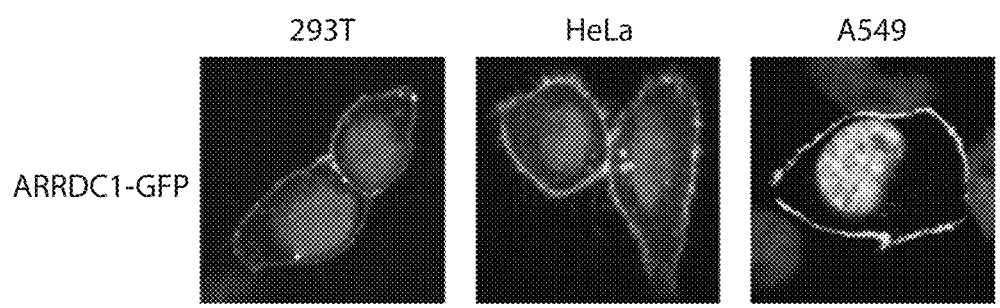

To better understand the biological consequences of the ARRDC1/TSG101 interaction, we investigated the cellular locations of individually expressed or co-expressed proteins that were differentially labeled (ARRDC1-GFP and mCherry-TSG101). We discovered that ARRDC1-GFP localized almost exclusively to the plasma membrane (FIG. 1E), a finding that was reproduced using Flag-tagged ARRDC1 (FIG. 7A) and in multiple cell lines tested (FIG. 7B). Consistent with our previous study (6), adventitiously expressed TSG101 was observed in the cytoplasm in multiple punctate foci, as is characteristic of endosome-associated localization (FIG. 1E). However, when co-expressed with ARRDC1, TSG101 was almost completely redistributed to the plasma membrane (FIG. 1E). Importantly, co-expression of TSG101 with the PSAP mutant of ARRDC1 did not result in redistribution of TSG101 to the cell membrane, indicating that recruitment of TSG101 to this location is dependent on the PSAP motif in ARRDC1.

ARRDC1 Drives the Release of Extracellular Microvesicles.

Figure 2A:
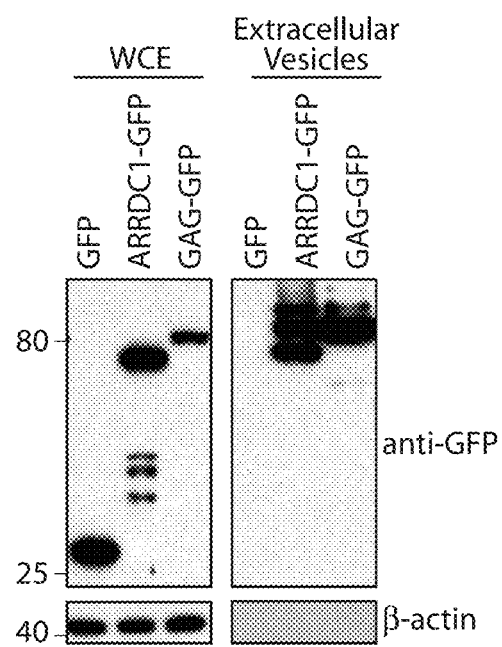
FIGS. 2A-2E. ARRDC1 expression potentiates release of vesicles that are devoid of exosomal markers and can fuse with recipient cells.
Figure 2B:
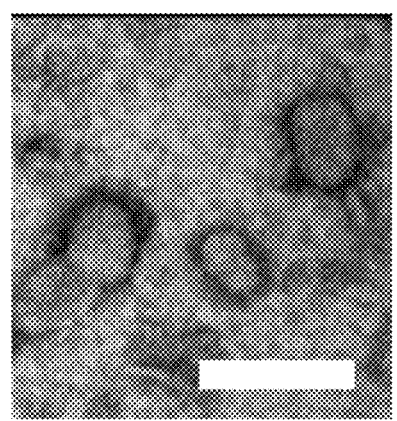

The dramatic relocalization of TSG101 from endosomes to plasma membrane by ARRDC1 is reminiscent of TSG101 recruitment by the HIV Gag protein during HIV budding (21, 22, 29). Given the striking parallel between ARRDC1 and Gag in recruitment of TSG101 from the cytosol to the plasma membrane, we hypothesized that ARRDC1 may function like Gag to mediate the direct release of plasma membrane-derived vesicles. To test this hypothesis, we expressed GFP, ARRDC1-GFP, or Gag-GFP in 293T cells and, 24 h later, harvested the conditioned media, and collected extracellular vesicles that were released by the cultured cells. Western blot analysis showed that Gag-GFP and ARRDC1-GFP proteins were robustly present in extracellular vesicles, while the control GFP protein was not (FIG. 2A). Consistent with this finding, ARRDC1 was included among the many proteins identified by mass spectrometry in microvesicles derived from human urine (30), bladder (31) and colon cancer cells (32). Electron microscopic examination of the released extracellular vesicles from ARRDC1-transfected cells indicated that the vesicles are less than 100 nm in diameter with an average of ~45 nm (FIG. 2B).

Figure 2C:
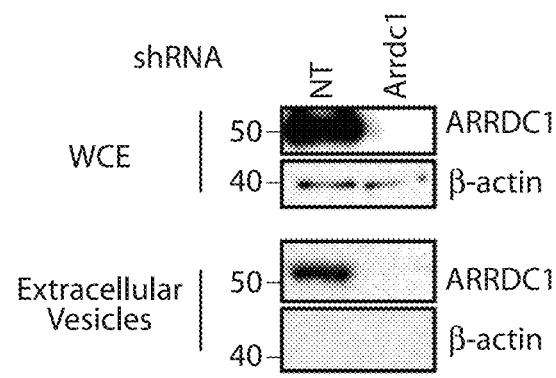
Figure 2D:
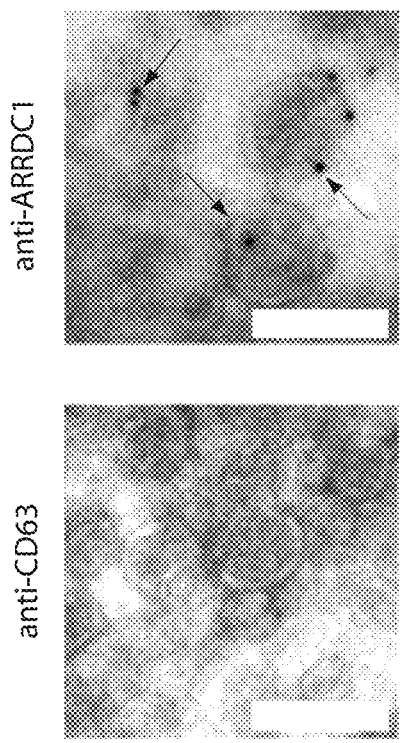

We next determined whether native ARRDC1 produced endogenously is released into microvesicles. As shown in FIG. 2C, extracellular vesicles collected from HEK293T cells contained ARRDC1 protein, indicating that ARRDC1 release into extracellular microvesicles is a process intrinsic to these cells. Additionally, depletion of ARRDC1 by siRNA resulted in loss of the extracellular ARRDC1 immunopositive signal (FIG. 2C), indicating that the released ARRDC1 protein is of cellular origin and is not derived from the fetal bovine serum supplementing the culture media. To further demonstrate the presence of ARRDC1 in the microvesicles we collected, we prepared collagen-embedded sections of extracellular vesicle pellets collected from 293T cells and stained the vesicles with ARRDC1 antibody. ARRDC1 was indeed detected in the microvesicles (FIG. 2D, upper panel). In contrast, these microvesicles stained negative for the exosomal marker LAMP3/CD63 (FIG. 2D, lower panel). We refer to these extracellular microvesicles as ARRDC1-mediated microvesicles (ARMMs).

Figure 2E:
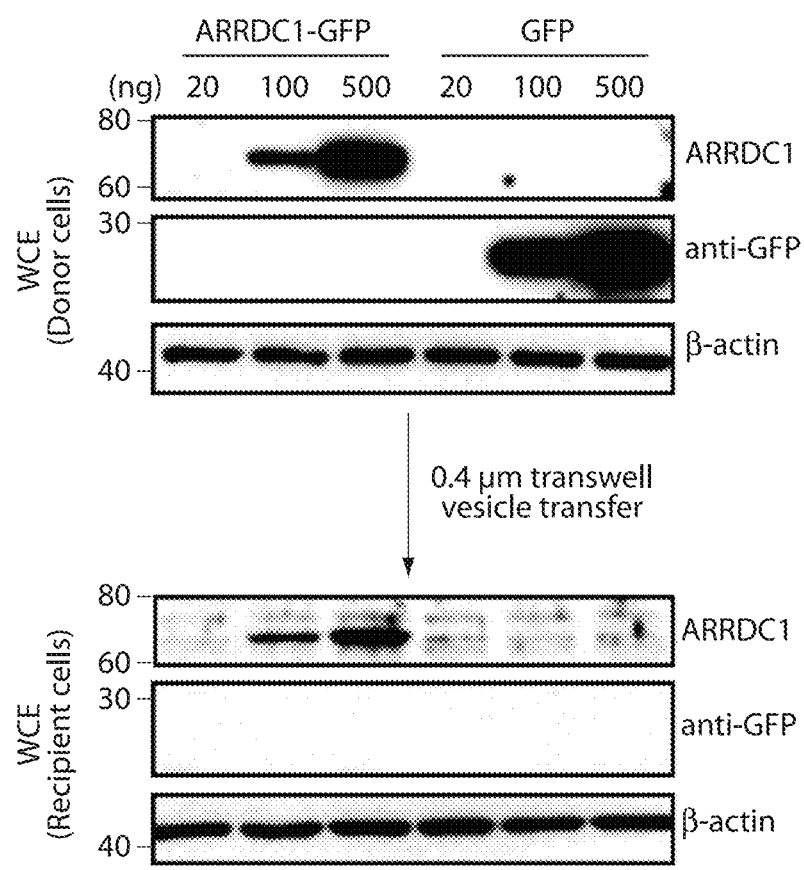

Using a co-culture system, we observed that ARRDC1 protein contained within ARMMs can be transferred between cells. ARMMs donor cells transfected with control GFP or ARRDC1-GFP were seeded atop untransfected recipient cells on a 0.4 μm porous membrane in a transwell (see Methods). After 30 h, cell lysates were collected from both donor and recipient cells and analyzed for ARRDC1-GFP or GFP. As shown in FIG. 2E, ARRDC1-GFP but not discrete GFP was detected in the recipient cells, indicating transfer of ARRDC1, which served in these experiments as a surrogate marker for ARMMs, to the recipient cells. Furthermore, the amount of ARRDC1 transferred to recipient cells was proportional to the abundance of adventitiously expressed ARRDC1 in the donor cells, providing further evidence of the functional role of ARRDC1 in ARMMs formation and indicating ARMMs-mediated protein transfer.

Release of ARMMs Requires TSG101 and the VPS4 ATPase.

Figure 3A:
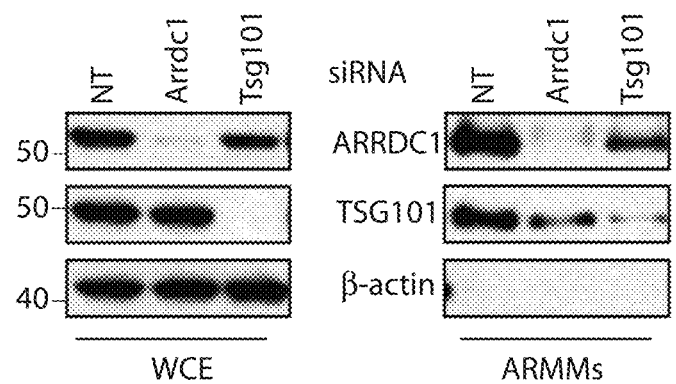
FIGS. 3A-3C. The ARRDC1-TSG101 interaction and the budding-related protein VPS4a are required for release of ARRDC1-regulated microvesicles (ARMMs).
Figure 3B:
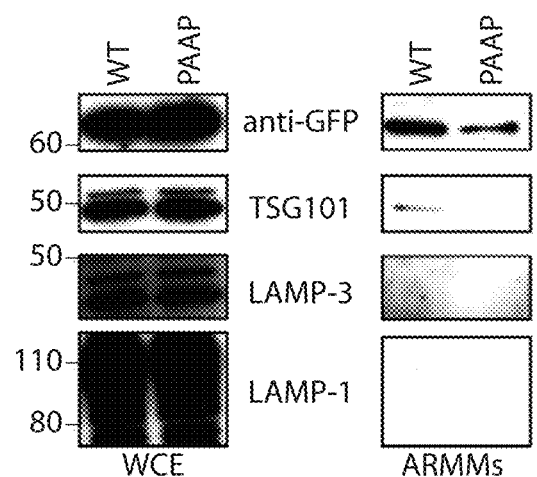

TSG101 is essential for MVB formation (33) and HIV budding (19). We determined whether the release of ARMMs also requires TSG101. As shown in FIG. 3A, knockdown of TSG101 expression reduced ARRDC1 in ARMMs by ~3 fold compared to control. TSG101 was also released into ARMMs, as it is in viral particles produced by Gag mediated budding (34). Moreover, when ARRDC1 was reduced, TSG101 abundance in ARMMs was reduced by ~70%. These data demonstrate a mutual dependency of ARRDC1 and TSG101 for inclusion in ARMMs. We next determined whether ARMMs release specifically requires the ARRDC1/TSG101 interaction. As shown in FIG. 3B, PSAP mutant ARRDC1 exhibited much decreased ARMMs release. Moreover, TSG101 was undetectable in culture medium fractions containing vesicles produced by cells expressing the ARRDC1 PSAP mutant (FIG. 3B). Collectively, these findings indicate that ARMMs release requires both TSG101 and its interaction with ARRDC1. Consistent with our immunogold staining observations (FIG. 2D), known exosomal markers LAMP3/CD63 and LAMP1 were not detected the ARRDC1-containing vesicles by Western blot analysis (FIG. 3B), indicating the non-exosomal nature of ARMMs.

Figure 3C:
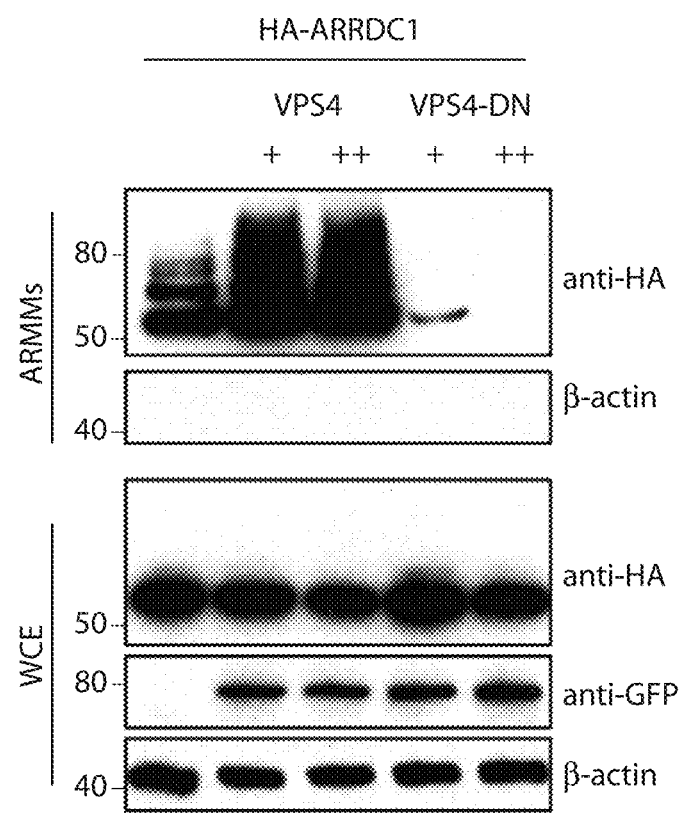

The VPS4 ATPase catalyzes the final "pinch-off" of the membranes in the formation of both MVBs and viral buds (35, 36) and is another essential component of the endosomal sorting pathway. We found that this ATPase is necessary also for ARMMs production. As shown in FIG. 3C, whereas expression of wild type VPS4 enhanced ARMMs release, expression of a catalytically inactive mutant of the ATPase (E228Q) almost completely blocked such release. The inhibitory effect is greater than TSG101 knockdown and may be attributable to the more potent effect by the VPS4 dominant negative overexpression on the function of the ESCRT pathway. Similarly greater effects of VPS4 in comparison with TSG101 have been observed for HIV Gag budding (19). Together, our data argue strongly that the ESCRT pathway is essential for the release of ARMMs, as it is for MVB formation and viral budding.

Arrestin Domain-Mediated ARRDC1 Localization at the Plasma Membrane is Required for ARMMs Release.

Figure 4A:
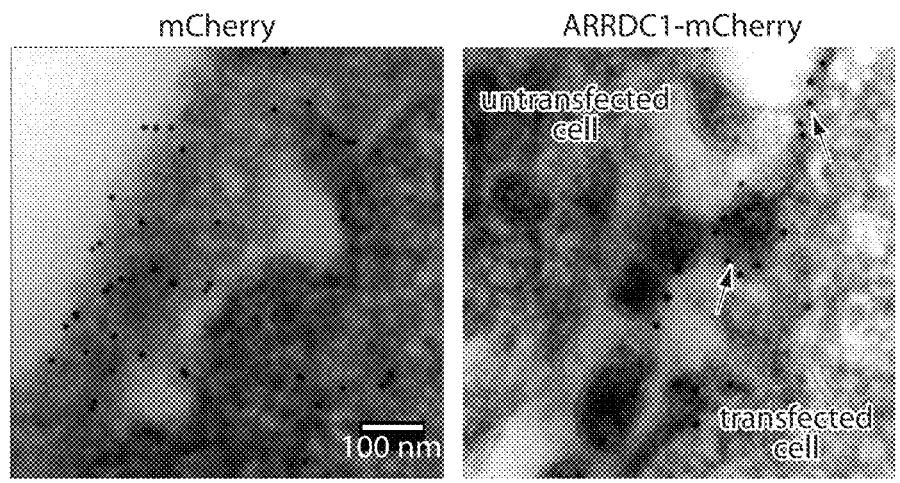
FIGS. 4A-4C. Arrestin domain-mediated association of ARRDC1 with the plasma membrane is essential for cell surface-derived budding of ARMMs.

To further establish that ARMMs are derived from the plasma membrane, we examined frozen sections of ARRDC1-expressing cells by electron microscopy. Cells were transfected with mCherry or ARRDC1-mCherry and treated with immunogold-labeled anti-mCherry antibody. Whereas mCherry displayed ubiquitous localization, ARRDC1-mCherry was limited to the cell membrane, and staining was specifically observed in budding vesicles emanating from the cell surface and also in ARMMs secreted into the extracellular space (FIG. 4A). This result supports the notion that ARMMs originate from and are formed at the cell surface.

Figure 4B:
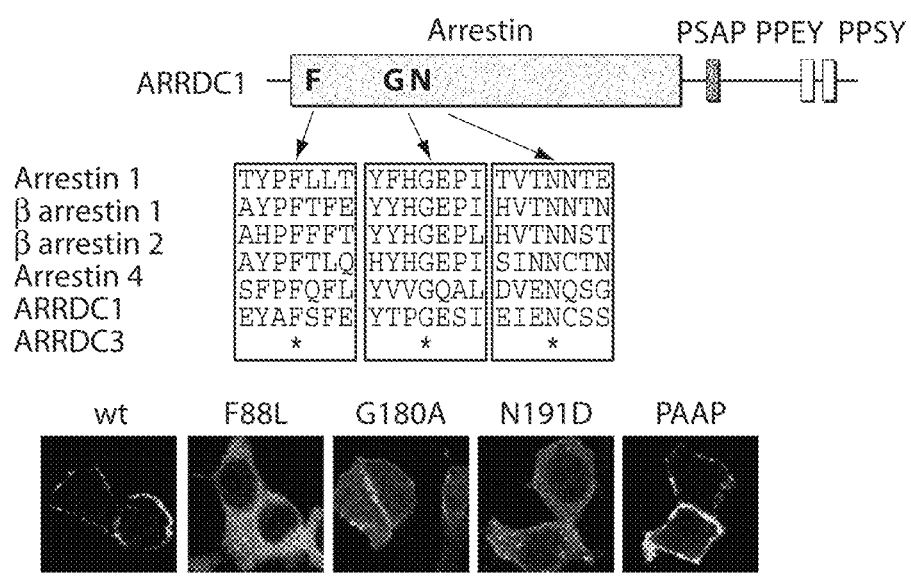
Figure 4C:
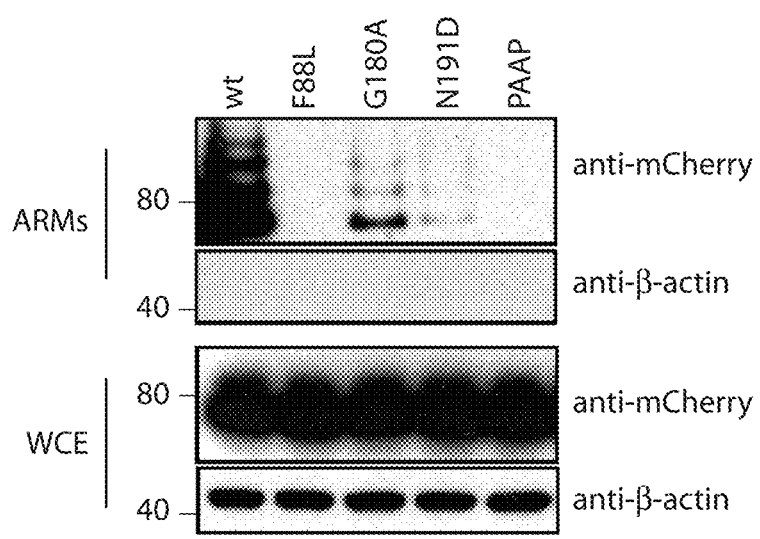

ARRDC1 contains a N-terminal domain that is highly homologous to arrestins (37). The arrestin proteins, and particularly the β-arrestins, have been shown to associate with receptors at the cell membrane to regulate their signaling (38). We hypothesized that the arrestin domain of ARRDC1 mediates its plasma membrane localization. To find highly conserved residues that might be important for the plasma membrane localization of ARRDC1, we aligned amino acid residues of human arrestin paralogues with ARRDC1 and with another ARRDC protein, ARRDC3, which is also known to localize to plasma membrane (39, 40) (FIG. 4B, upper panel). Several conserved residues (F88, G180, and N191) in the arrestin domain of ARRDC1 were identified. We mutated these conserved residues and determined the cellular location of the corresponding ARRDC1-mCherry fusion proteins. The F88L mutation completely abolished ARRDC1 association with the plasma membrane, leaving the mutant protein evenly distributed in the cytosol, whereas the G180A and N191D mutants retained partial plasma membrane localization (FIG. 3B). Consistent with data shown in FIG. 1E, the plasma membrane localization of ARRDC1 protein was not perturbed by mutation of PSAP (SEQ ID NO: 37) to PAAP (SEQ ID NO: 32). We then examined the effects of arrestin domain mutants on ARMMs release. Unlike PAAP mutant ARRDC1, which localizes to the plasma membrane but is not released, arrestin domain mutants of ARRDC1 proteins interfered with ARMMs release in a manner that correlated with the extent of disruption of plasma membrane-association by the mutations (FIG. 4C). The F88L mutant completely blocked ARMMs release, whereas the other two mutants had partial inhibitory effects (FIG. 4C). These results demonstrate that the arrestin domain mediates ARRDC1 localization to the plasma membrane and is required for the release of ARMMs.

Ubiquitination of ARRDC1 by HECT Domain Ubiquitin Ligase WWP2 Facilitates ARMMs Release.

Figure 5A:
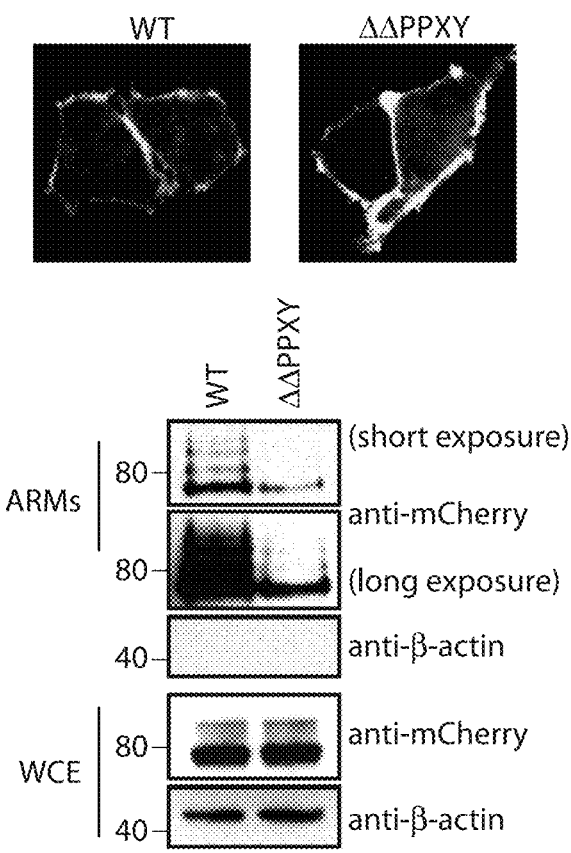
FIGS. 5A-5B. WWP2 interacts with and ubiquitinates ARRDC1 to enhances ARMMs release.
Figure 8:
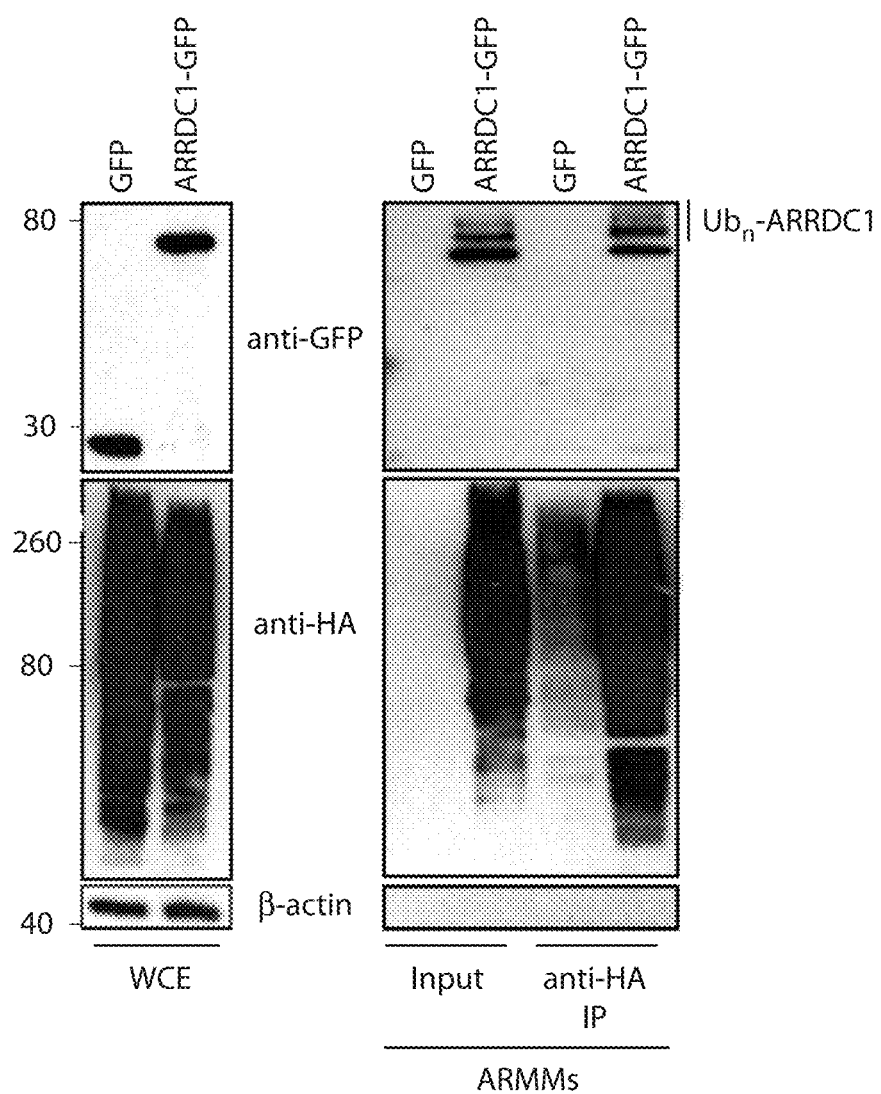
FIG. 8. ARRDC1 ubiquitination in ARMMs. 293T cells were co-transfected with HA-ubiquitin and GFP or ARRDC1-GFP. Cells and ARMMs were later lysed in NP-40 lysis buffer. ARMMs lysates were pre-cleared with protein A agarose beads and subjected to an anti-HA immunoprecipitation to collect ubiquitinated proteins. Cell lysates, ARMM lysates, and anti-HA ARMMs immunoprecipitates were analyzed by Western blotting with the indicated antibodies.

ARRDC1 contains two highly conserved PPXY motifs, which in Gag and analogous viral proteins are targets for ubiquitin ligases, near its C-terminus. Although cellular localization of PPXY mutant ARRDC1 proteins was not perturbed, expression of these proteins markedly inhibited ARMMs release (FIG. 5A). In addition, we observed a corresponding decrease in ARRDC1 band laddering (FIG. 5A). Such laddering is suggestive of ubiquitination, and to learn whether ARRDC1 in ARMMs is in fact ubiquitinated, we co-transfected 293T cells with HA-tagged ubiquitin and ARRDC1-GFP, and collected ARMMs for immunoprecipitation by anti-HA antibody. As shown in FIG. 8, total lysates of ARMMs collected from ARRDC1-expressing cells also showed increased ubiquitination, compared with a GFP control (FIG. 8) supporting the notion that the observed laddering of ARMMs-associated ARRDC1 protein results from ubiquitination and additionally suggesting that ubiquitination facilitates ARMMs release.

Figure 5B:
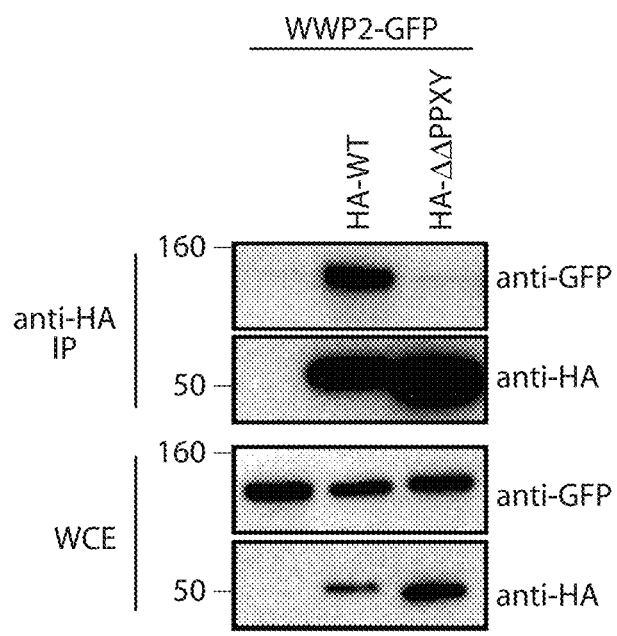

To identify possible candidates for the ubiquitin E3 ligase that mediates ARRDC1 ubiquitination and which may have a role in ARMMs release, anti-ARRDC1 rabbit antibody was used to immunoprecipitate endogenous ARRDC1 and associated proteins from 293T cell lysates, and immunoprecipitates were analyzed by mass spectrometry. Among the proteins identified in ARRDC1 immunoprecipitates was WWP2, which is a member of the NEDD4 E3 ligase family (41, 42). We confirmed the interaction between ARRDC1 and WWP2 by co-immunoprecipitation (FIG. 5B). WWP2 contains WW domains that are known to interact with PPXY motifs (41, 42). We found that mutations in the PPXY domains in ARRDC1 almost completely inhibited its interaction with WWP2 (FIG. 5B). Additionally, ubiquitination of ARRDC1 was enhanced by WWP2 but was not observed in cells expressing the fragment containing only the WW domains, indicating a dominant negative effect of the WW domain expression on ARRDC1 ubiquitination. Interestingly, both WWP2 and the WW domain fragment were also detected in extracellular vesicle fractions, consistent with the observed WW domain-mediated interaction between ARRDC1 and WWP2. Furthermore, a specific role for WWP2 in ARMMs release was demonstrated, as siRNA-mediated WWP2 knockdown markedly reduced the amount of ARRDC1 released in ARMMs. The data obtained in this series of experiments indicate that WWP2, through interaction with PPXY motifs in ARRDC1, ubiquitinates ARRDC1 and enhances ARMMs release.

Identification of Proteins in ARMMs.

Purification of ARMMs.

Figure 10:
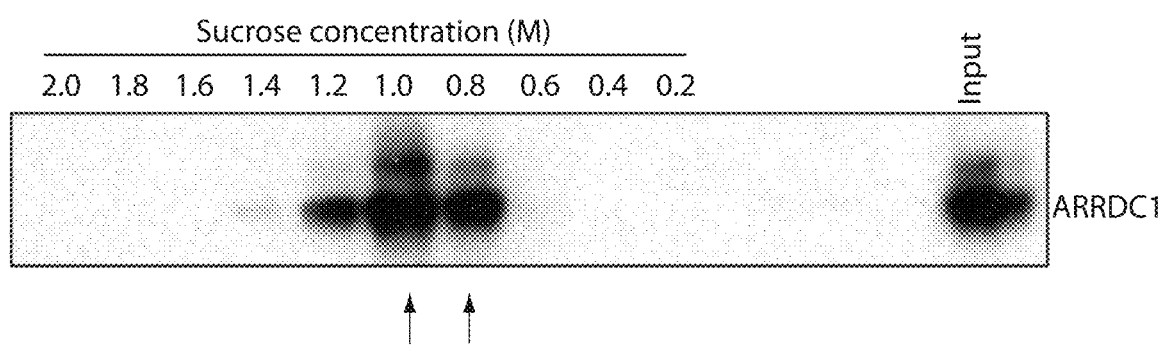
FIG. 10. Sucrose density gradient separation of ARMMs. ARMMs were initially collected through ultracentrifugation of ~200 ml of media supernatant of actively growing HCC1419 cells. ARMMs were then subjected to further purification by sucrose gradient separation as follows. Briefly, ARMMs were re-suspended in 0.5 ml PBS and laid on top of a sucrose step-wise gradient (from 0.2 to 2 M, 1 ml of each concentration). The sample was then centrifuged in a swinging bucket (SW50.1 rotor, Beckman) at 130,000×g for 18 hours. After centrifugation, ten (10) fractions of 1 ml volume were collected. A small volume (~10 μl) of each fraction was subjected to SDS-PAGE followed by Western blotting analysis for ARRDC1.

ARMMs were initially collected through ultracentrifugation of ~200 ml of media supernatant of actively growing HCC1419 cells. ARMMs were then subjected to further purification by sucrose gradient separation as follows. Briefly, ARMMs were re-suspended in 0.5 ml PBS and laid on top of a sucrose step-wise gradient (from 0.2 to 2 M, 1 ml of each concentration, FIG. 10). The sample was then centrifuged in a swinging bucket (SW50.1 rotor, Beckman) at 130,000× g for 18 hours. After centrifugation, about ten (10) fractions of 1 ml volume were collected. A small volume (~10 μl) of each fraction was subjected to SDS-PAGE followed by Western blotting analysis for ARRDC1. As shown in FIG. 10, ARRDC1 was detected in mostly three sucrose fractions (0.8, 1.0 and 1.2 M).

Identification of Proteins in ARMMs.

Figure 11:
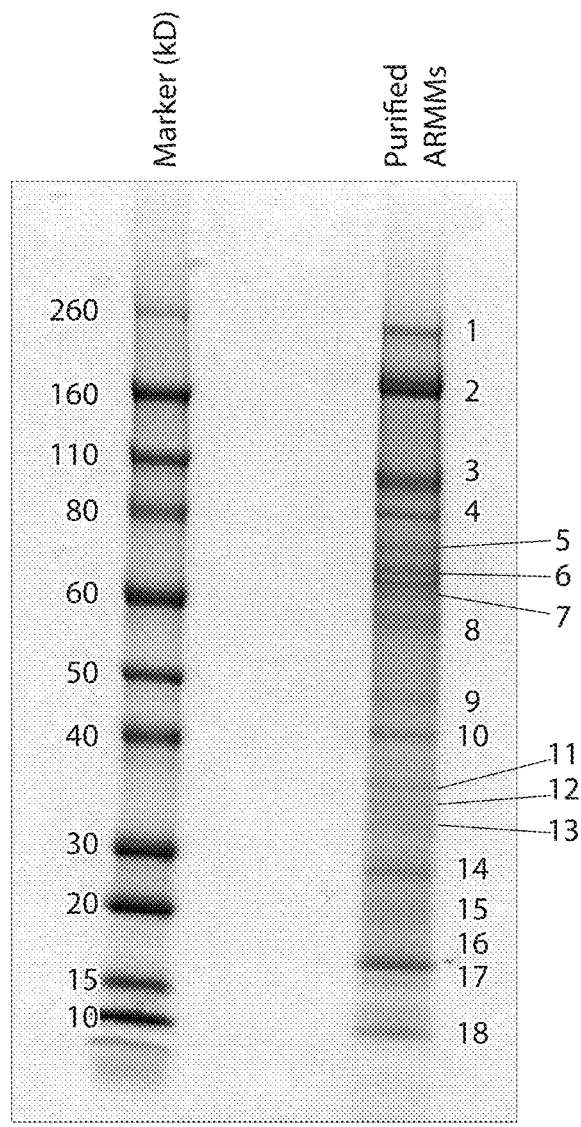
FIG. 11. SDS-PAGE of purified ARMMs. Following sucrose gradient separation, two fractions (4, 5, see arrows in FIG. 10) that contain most of ARMMs were combined together, diluted with PBS to a volume of 10 ml, and re-centrifuged (100,000×g for 2 hours). The resulting pellet was lysed in SDS-PAGE loading buffer, and proteins were resolved by SDS-PAGE (12% gel) followed by Coomassie-blue staining. About 18 distinct protein bands were identified and analyzed by mass spectrometry.
Figure 12:
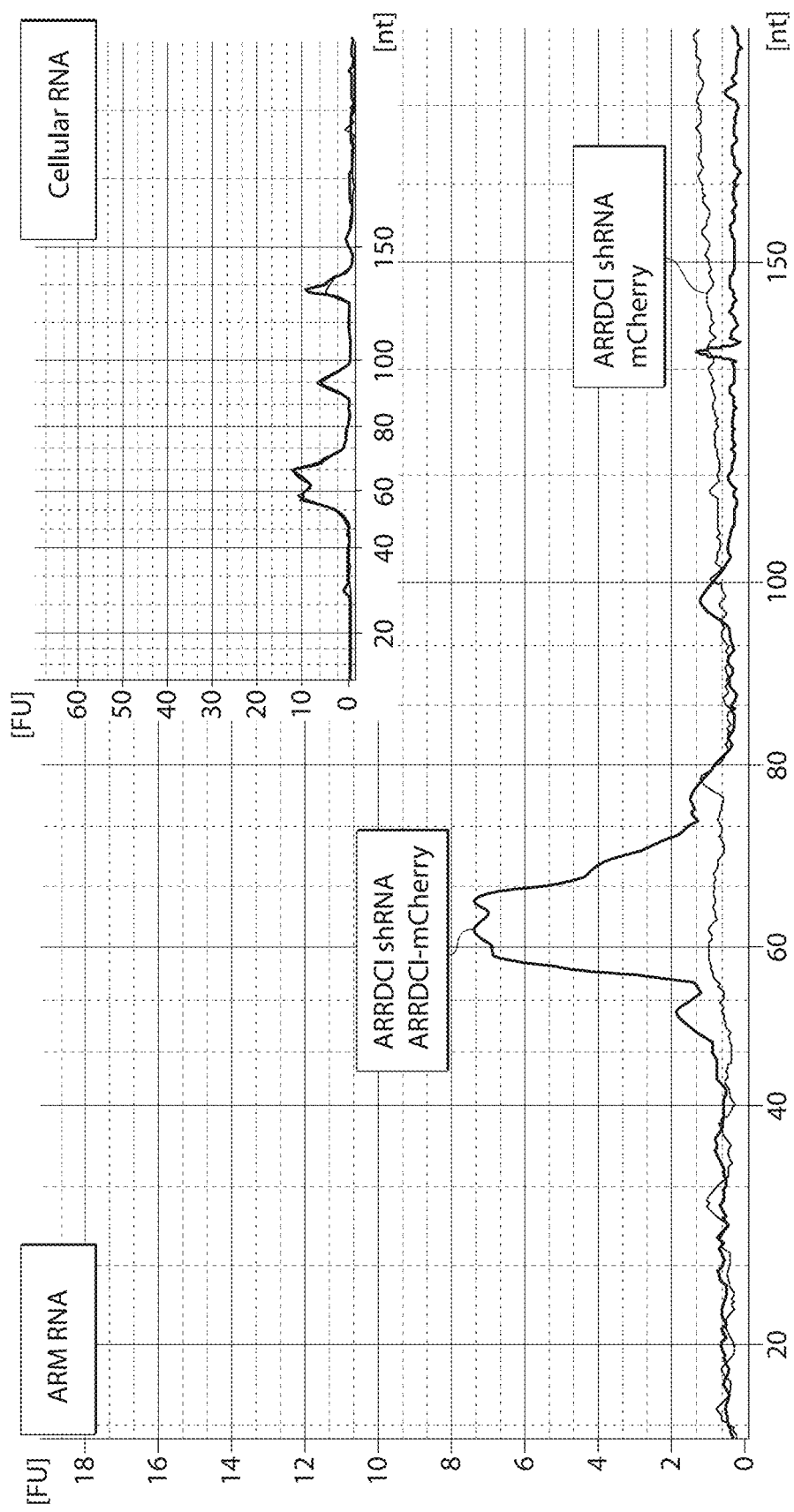
FIG. 12. Detection of small RNA species in ARMMs. HEK293 cells were first stably transduced with ARRDC1-shRNA to knock down endogenous ARRDC1. ARRDC1-knockdown cells were then transfected with constructs expressing either mCherry or ARRDC1-mCherry. Supernatant medium from both cells were subjected to ultracentrifugation. RNAs in centrifuged pellets were extracted by Trizol reagent (Invitrogen) and analyzed by Bioanalyzer (Agilent). Cells expressing ARRDC1-mcherry but not the control mCherry contain detectable RNA species, including small ones ranging from 50-80 nucleotides. The cellular RNA profiles from mCherry- and ARRDC1-mCherry-expressing cells are very similar (figure inset).

Following sucrose gradient separation, two fractions (0.8 and 1.0 M sucrose) that contain most of ARMMs (marked by arrows in FIG. 10) were combined together, diluted with PBS to a volume of 10 ml and re-centrifuged (100,000×g for 2 hours). The resulting pellet was lysed in SDS-PAGE loading buffer, and proteins were resolved by SDS-PAGE (12% gel) followed by coomassie-blue staining (FIG. 11). About 18 distinct protein bands were identified and analyzed by mass spectrometry. Over 500 proteins were identified with at least two peptides. ARRDC1 was identified in several fractions, consistent with results of ARRDC1 modification by ubiquitination described herein (see also Nabhan et al., Formation and release of arrestin domain-containing protein 1-mediated microvesicles (ARMMs) at plasma membrane by recruitment of TSG101 protein. *Proc Natl Acad Sci USA.* 2012; 109(11):4146-51; the entire contents of which are incorporated herein by reference). The notion of ARRDC1 modification by ubiquitination is further supported by the identification of several ubiquitin E3 ligases (WWP1, WWP2 and ITCH) in the ARMMs (Table 1). Gene/Protein Nomenclature follows official guidelines for gene nomenclature (see Hester et al., Guidelines for Human Gene Nomenclature Genomics 79(4):464-470 (2002), and the HUGO Gene Nomenclature Committee gene name database, accessible at genenames.org).

TABLE 1

Proteins identified in ARMMs.

| Band | # of Peptides identified in Mass-Spec | Gene/Protein Symbol |
|---|---|---|
| #1 | | |
| | 52 | MYO10 |
| | 22 | TLN2 |
| | 18 | MYO18A |
| | 16 | MTOR |
| | 5 | KIF13B |
| | 5 | KIAA1244 |
| #2 | | |
| | 14 | LNPEP |
| | 14 | ERBB2IP |
| | 10 | TNS3 |
| | 7 | MON2 |
| | 9 | KIAA1522 |
| #3 | | |
| | 36 | CASK |
| | 22 | NOTCH2 |
| | 16 | AP1B1 |
| | 15 | USP5 |
| | 9 | EXOC2 |
| | 7 | VAV2 |
| | 7 | EXOC1 |
| | 5 | MTSS1 |
| | 5 | ITCH |
| | 6 | XPOT |
| | 5 | ARRDC1 |
| #4 | | |
| | 21 | MARK2 |
| | 17 | PIK3R2 |
| | 16 | ENAH |
| | 8 | QARS |
| | 7 | CNNM4 |
| | 6 | EFCAB4B |
| | 5 | KIAA1598 |
| #5 | | |
| | 26 | EXOC7 |
| | 17 | ZDHHC5 |
| | 14 | EXOC8 |
| | 13 | PERMT2 |
| | 12 | MLPH |
| | 10 | RHPN2 |
| | 9 | LSS |
| | 9 | IPI:IPI00719051.3 |
| | 9 | PVRL2 |
| | 11 | ZYX |
| | 8 | ARRDC1 |
| | 5 | EIF4B |
| | 6 | TRIM3 |
| #6 | | |
| | 7 | SYTL1 |
| | 5 | PVRL2 |
| | 8 | PKM2 |
| | 6 | NF2 |
| | 5 | GALNT7 |
| #7 | | |
| | 8 | PTPRD |
| | 5 | ARRDC1 |
| #8 | | |
| | 42 | PKM2 |
| | 22 | SPAG1 |
| | 18 | YARS |
| | 16 | SNTB2 |
| | 13 | GRB7 |
| | 9 | FAM83F |
| | 10 | CPM |
| | 12 | ARRDC1 |
| | 8 | RAD23B |
| | 8 | EPB41L5 |

TABLE 1-continued

Proteins identified in ARMMs.

| Band | # of Peptides identified in Mass-Spec | Gene/Protein Symbol |
|---|---|---|
|  | 6 | ILK-2 |
|  | 10 | GRB7 |
|  | 7 | SPINT1 |
|  | 6 | FNBP1L |
|  | 5 | LRRC1 |
|  | 6 | AHCYL2 |
| #9 |  |  |
|  | 16 | AP1M2 |
|  | 14 | PSMC3 |
|  | 12 | IPI:IPI00328587.4 |
|  | 14 | CXADR |
|  | 19 | ARRDC1 |
|  | 10 | PARVA |
|  | 8 | C8orf30A |
|  | 9 | KIAA0174 |
|  | 6 | TUBB2C |
|  | 6 | OCLN |
| #10 |  |  |
|  | 10 | CSNK2A1 |
|  | 8 | INPP5A |
|  | 8 | MAPK3 |
|  | 7 | PPID |
|  | 7 | FAM102A |
|  | 7 | ARRDC1 |
|  | 8 | SH3GL1 |
|  | 5 | TUBB2C |
|  | 5 | KIAA0174 |
| #11 |  |  |
|  | 14 | STX16 |
|  | 8 | AIP |
|  | 10 | FAM84B |
|  | 8 | CSNK1A1 |
|  | 6 | PRKAG1 |
| #12 |  |  |
|  | 14 | STARD10 |
|  | 15 | LASP1 |
|  | 12 | AKR7L |
|  | 9 | STX16 |
|  | 8 | SRM |
|  | 7 | KIAA0174 |
|  | 8 | TWF1 |
|  | 6 | CSNK1A1L |
|  | 7 | CSNK1A1 |
|  | 7 | PPCS |
|  | 5 | STUB1 |
| #13 |  |  |
|  | 10 | VAV3 |

Many of the identified proteins, including CD9, TSG101, PDCD6IP, Annexins, and heat shock protein HSPA8, have previously been identified in exosomes. This could be due to the inclusion of some exosomes in the purified ARMMs fractions or could suggest that ARMMs and exosomes may share some common components. To identify unique ARMMs proteins, the protein list obtained from mass spec was compared with known exosomal proteins in the ExoCarta database (exocarta.org). This analysis resulted in the identification of over 100 proteins that were not found in exosomes and thus are likely unique components of ARMMs (Table 1). Among the proteins are several member of the exocyst complex (EXOC7, EXOC8, EXOC1, and EXOC2), which is involved in exocytosis and mediates the tethering and spatial targeting of post-Golgi vesicles to plasma membrane. The presence of exocyst proteins in ARMMs suggests new function of these proteins and may point to specific targeting mechanism for ARMMs.

ARMMs Contain RNA Species.

HEK293 cells were first stably transduced with ARRDC1-shRNA to knock down endogenous ARRDC1. ARRDC1-knockdown cells were then transfected with nucleic acid constructs expressing either mCherry or ARRDC1-mcherry. Supernatant medium from both types of cells were subjected to ultracentrifugation. RNAs in centrifuged pellets were extracted by Trizol reagent (Invitrogen) and analyzed by Bioanalyzer (Agilent). While the cellular RNA profiles from mCherry- and ARRDC1-mCherry-expressing cells are very similar (figure inset), supernatants from cells expressing ARRDC1-mcherry, but not the control mCherry cells, contained detectable RNA species, including small ones ranging from 50-80 nucleotides. Delivery of these RNA species through ARMMs to target cell or tissue may mediate specific biological functions.

Discussion

Mammalian cells are capable of secreting into the extracellular milieu a variety of microvesicles, among which are particles termed exosomes, which are derived from MVBs of late endosomes (2, 14, 43). The results we report reveal a type of microvesicle that is generated by direct plasma membrane budding (DPMB) and is distinct from exosomes. Whereas TSG101 is located at the surface of late endosomes during the formation of MVBs, TSG101 is recruited by ARRDC1 to the surface of cells for production of ARMMs. Consistent with the plasma membrane origin of ARMMs, our data show that ARMMs lack late endosomal markers such as CD63 and LAMP1 (FIG. 2D and FIG. 3B).

Figure 6:
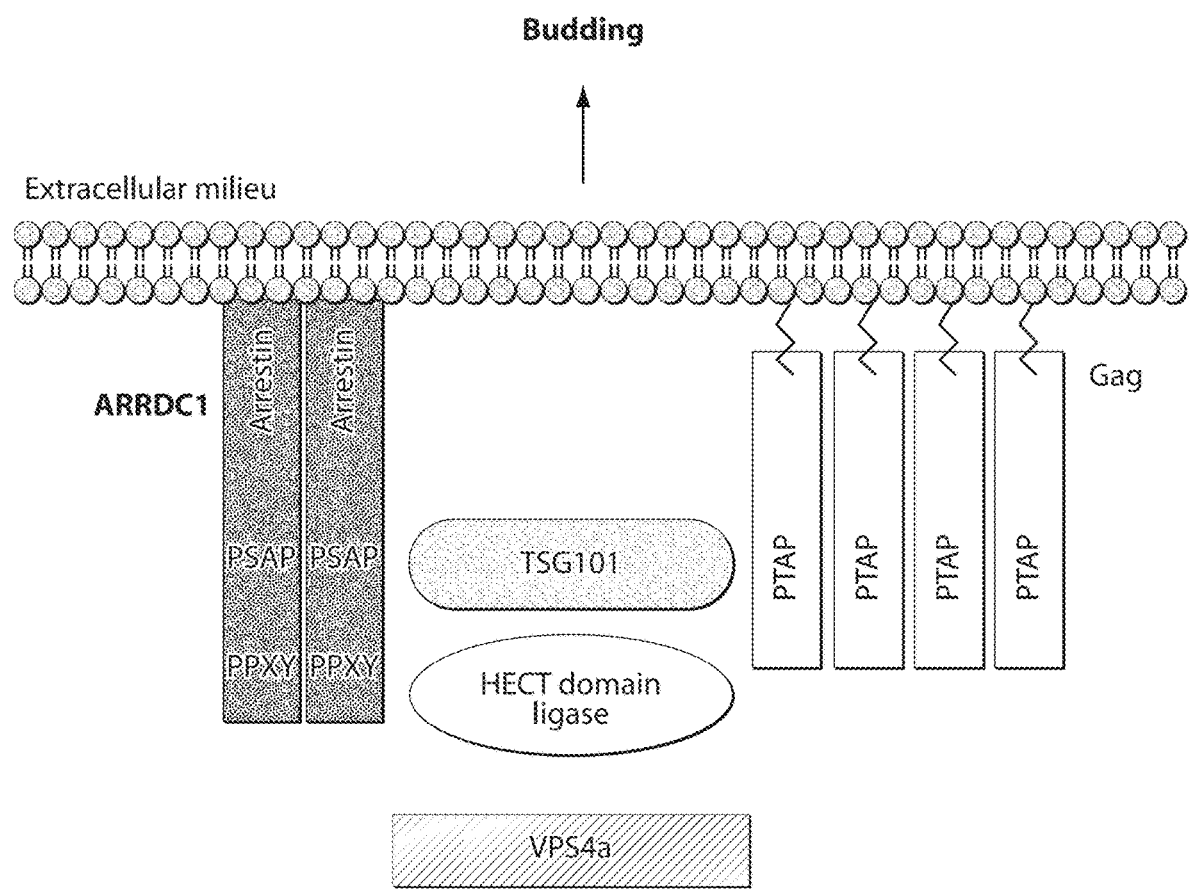
FIG. 6. A model for ARRDC1-mediated ARMMs formation and Gag-mediated viral budding. Both ARRDC1 and Gag interact with TSG101, are ubiquitinated by HECT domain ligases, and require VPS4 ATPase to produce budding vesicles. The sequences listed from left to right correspond to SEQ ID NOs: 37 and 40.
Figure 9:
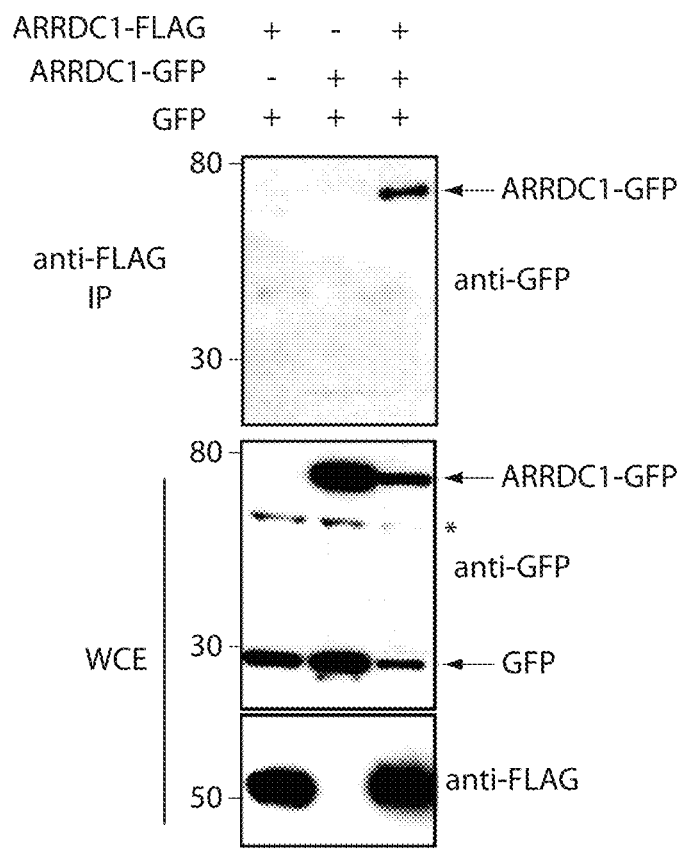
FIG. 9. Self-association of ARRDC1. 293T cells were transfected with the specified plasmids and then harvested in NP-40 lysis buffer. Lysates were pre-cleared and then subjected to an anti-FLAG immunoprecipitation (IP). Corresponding samples were analyzed by Western blotting with indicated antibodies. WCE: whole cell extracts.

Our findings suggest a direct analogy between ARMMs formation and budding mediated by Gag and other viral proteins (FIG. 6). It has been well established that many viruses including HIV utilize cellular machinery for their egress (16-18). HIV Gag uses PSAP motifs to recruit TSG101 and other endosomal pathway proteins to bud from the cell surface. It has been suggested that Gag protein functionally mimics host protein Hrs, which interacts with TSG101 through a PSAP motif (11). However, while Hrs and Gag interact with TSG101 similarly, Hrs is an early endosome-associated protein and does not localize to the plasma membrane, where viral budding occurs (6, 44). In contrast, ARRDC1 is directed to the plasma membrane by its arrestin-like domain and multimerizes there (FIG. 9), as does Gag (45). Moreover, both Gag and ARRDC1, when adventitiously expressed, are sufficient to induce vesicle formation. Additionally, our results demonstrate that like HIV Gag budding, ARMMs release requires both TSG101 and VPS4. These data strongly suggest that HIV Gag and likely other viral proteins mimic ARRDC1 to mediate the release of viral particles from host cells. Whether ARMMs production also requires ESCRT-III and Alix, which are involved in Gag-mediated HIV budding (46), currently is not known. Recently, the shedding of ESCRT-dependent microvesicles that may prove to be ARMMs has been found to be increased in C. elegans embryos by loss of the evolutionarily-conserved P4-ATPase, TAT-5, and consequent exposure of phosphaidylethanolamine at the cell surface (47).

ARRDC1 belongs to a family of ARRDC proteins that share a common domain structure: an arrestin domain at the N-termini and two PPXY motifs at the C-termini (37). ARRDC1 contains a highly conserved PSAP motif that is not found in other ARRDC proteins. The PSAP motif directly interacts with TSG101, and in cells that adventitiously overexpress ARRDC1, redirects TSG101 from endosomes to the cell surface. Potentially, such ARRDC1-mediated relocalization of TSG101 may alter endosomal trafficking and sorting and consequently, signal transduction by receptors subjected to endosomal sorting mechanisms. As the arrestin domain of ARRDC1 mediates localization of this protein to the plasma membrane, and as β-arrestins are known to bind to phosphorylated receptor proteins (38), ARRDC1 may prove to be a multifaceted regulator of receptor-mediated signaling, Our data also indicate a role for ARRDC1 ubiquitination in ARMMs release. We showed that ARRDC1 PPXY motifs interact with the ubiquitin E3 ligase WWP2 (FIG. 5B), and that WWP2 mediates the ubiquitination of ARRDC1—in particular the ARDDC1 species that are incorporated into ARMMs. A recent study has shown that another E3 ligase WWP1 can also interact with and ubiquitinate ARRDC1 (28). It remains unclear whether WWP1 also has a role in ARMMs production. Interestingly, our previous study has shown that the ARRDC1 relative, ARRDC3, also interacts with members of the NEDD4 E3 ligase family (40). Through interaction with NEDD4 E3 ligases, ARRDC3 mediates ubiquitination of β2-adrenergic receptors.

Extracellular microvesicles have the potential to function as mediators of cell-cell communication (2). Indeed, several studies have identified functional proteins and RNA molecules from exosomal microvesicles and have shown that macromolecules transferred by exosomes can produce functional effects in recipient cells (48, 49). ARMMs may function similarly in cellular communication, and consistent with this notion, we found that ARMMs can transfer ARRDC1 between cells. ARMMs, like exosomes, may contain RNAs or additional proteins involved in cell-cell communication, and given the ability of ARRDC1 to localize to the plasma membrane, some of these proteins may be plasma membrane receptors.

REFERENCES

1. Hurley J H, Boura E, Carlson L A, & Rozycki B (2010) Membrane budding. Cell 143:875-887.
2. Thery C, Ostrowski M, & Segura E (2009) Membrane vesicles as conveyors of immune responses. Nat Rev Immunol 9:581-593.
3. Henne W M, Buchkovich N J, & Emr S D (2011) The ESCRT pathway. Dev Cell 21:77-91.
4. Katzmann D J, Odorizzi G, & Emr S D (2002) Receptor downregulation and multivesicular-body sorting. Nat Rev Mol Cell Biol 3:893-905.
5. Babst M, Odorizzi G, Estepa E J, & Emr S D (2000) Mammalian tumor susceptibility gene 101 (TSG101) and the yeast homologue, Vps23p, both function in late endosomal trafficking. Traffic 1:248-258.
6. Lu Q, Hope L W, Brasch M, Reinhard C, & Cohen S N (2003) TSG101 interaction with HRS mediates endosomal trafficking and receptor down-regulation. Proc Natl Acad Sci USA 100:7626-7631.
7. Pornillos O, Alam S L, Davis D R, & Sundquist W I (2002) Structure of the Tsg101 UEV domain in complex with the PTAP motif of the HIV-1 p6 protein. Nat Struct Biol 9:812-817.
8. Pornillos O, Alam S L, Rich R L, Myszka D G, Davis D R, & Sundquist W I (2002) Structure and functional interactions of the Tsg101 UEV domain. EMBO J 21:2397-2406.
9. Sundquist W I, Schubert H L, Kelly B N, Hill G C, Holton J M, & Hill C P (2004) Ubiquitin recognition by the human TSG101 protein. Mol Cell 13:783-789.
10. Bache K G, Brech A, Mehlum A, & Stenmark H (2003) Hrs regulates multivesicular body formation via ESCRT recruitment to endosomes. J Cell Biol 162:435-442.
11. Pornillos O, Higginson D S, Stray K M, Fisher R D, Garrus J E, Payne M, He G P, Wang H E, Morham S G, & Sundquist W I (2003) HIV Gag mimics the Tsg101-recruiting activity of the human Hrs protein. J Cell Biol 162:425-434.
12. von Schwedler U K, Stuchell M, Muller B, Ward D M, Chung H Y, Morita E, Wang H E, Davis T, He G P, Cimbora D M, et al. (2003) The protein network of HIV budding. Cell 114:701-713.
13. Hurley J H & Stenmark H (2011) Molecular mechanisms of ubiquitin-dependent membrane traffic. Annu Rev Biophys 40:119-142.
14. Schorey J S & Bhatnagar S (2008) Exosome function: from tumor immunology to pathogen biology. Traffic 9:871-881.
15. Thery C, Zitvogel L, & Amigorena S (2002) Exosomes: composition, biogenesis and function. Nat Rev Immunol 2:569-579.
16. Bieniasz P D (2009) The cell biology of HIV-1 virion genesis. Cell Host Microbe 5:550-558.
17. Demirov D G & Freed E O (2004) Retrovirus budding. Virus Res 106:87-102.
18. Morita E & Sundquist W I (2004) Retrovirus budding. Annu Rev Cell Dev Biol 20:395-425.
19. Garrus J E, von Schwedler U K, Pornillos O W, Morham S G, Zavitz K H, Wang H E, Wettstein D A, Stray K M, Cote M, Rich R L, et al. (2001) Tsg101 and the vacuolar protein sorting pathway are essential for HIV-1 budding. Cell 107:55-65.
20. VerPlank L, Bouamr F, LaGrassa T J, Agresta B, Kikonyogo A, Leis J, & Carter C A (2001) Tsg101, a homologue of ubiquitin-conjugating (E2) enzymes, binds the L domain in HIV type 1 Pr55(Gag). Proc Natl Acad Sci USA 98:7724-7729.
21. Martin-Serrano J, Zang T, & Bieniasz P D (2001) HIV-1 and Ebola virus encode small peptide motifs that recruit Tsg101 to sites of particle assembly to facilitate egress. Nat Med 7:1313-1319.
22. Martin-Serrano J, Zang T, & Bieniasz P D (2003) Role of ESCRT-I in retroviral budding. J Virol 77:4794-4804.
23. Demirov D G, Ono A, Orenstein J M, & Freed E O (2002) Overexpression of the N-terminal domain of TSG101 inhibits HIV-1 budding by blocking late domain function. Proc Natl Acad Sci USA 99:955-960.
24. Gottlinger H G, Dorfman T, Sodroski J G, & Haseltine W A (1991) Effect of mutations affecting the p6 gag protein on human immunodeficiency virus particle release. Proc Natl Acad Sci USA 88:3195-3199.
25. Huang M, Orenstein J M, Martin M A, & Freed E O (1995) p6Gag is required for particle production from full-length human immunodeficiency virus type 1 molecular clones expressing protease. J Virol 69:6810-6818.
26. Freed E O & Mouland A J (2006) The cell biology of HIV-1 and other retroviruses. Retrovirology 3:77.
27. Martin-Serrano J & Neil S J Host factors involved in retroviral budding and release. Nat Rev Microbiol 9:519-531.
28. Rauch S & Martin-Serrano J (2011) Multiple interactions between the ESCRT machinery and arrestin-related proteins: implications for PPXY-dependent budding. J Virol 85:3546-3556.

29. Ono A & Freed E O (2004) Cell-type-dependent targeting of human immunodeficiency virus type 1 assembly to the plasma membrane and the multivesicular body. J Virol 78:1552-1563.
30. Pisitkun T, Shen R F, & Knepper M A (2004) Identification and proteomic profiling of exosomes in human urine. Proc Natl Acad Sci USA 101:13368-13373.
31. Welton J L, Khanna S, Giles P J, Brennan P, Brewis I A, Staffurth J, Mason M D, & Clayton A (2010) Proteomics analysis of bladder cancer exosomes. Mol Cell Proteomics 9:1324-1338.
32. Mathivanan S, Lim J W, Tauro B J, Ji H, Moritz R L, & Simpson R J (2009) Proteomics analysis of A33 immunoaffinity-purified exosomes released from the human colon tumor cell line LIM1215 reveals a tissue-specific protein signature. Mol Cell Proteomics 9:197-208.
33. Razi M & Futter C E (2006) Distinct roles for Tsg101 and Hrs in multivesicular body formation and inward vesiculation. Mol Biol Cell 17:3469-3483.
34. Hammarstedt M & Garoff H (2004) Passive and active inclusion of host proteins in human immunodeficiency virus type 1 gag particles during budding at the plasma membrane. J Virol 78:5686-5697.
35. Babst M (2005) A protein's final ESCRT. Traffic 6:2-9.
36. Scott A, Chung H Y, Gonciarz-Swiatek M, Hill G C, Whitby F G, Gaspar J, Holton J M, Viswanathan R, Ghaffarian S, Hill C P, et al. (2005) Structural and mechanistic studies of VPS4 proteins. EMBO J 24:3658-3669.
37. Alvarez C E (2008) On the origins of arrestin and rhodopsin. BMC Evol Biol 8:222.
38. Lefkowitz R J & Shenoy S K (2005) Transduction of receptor signals by beta-arrestins. Science 308:512-517.
39. Draheim K M, Chen H B, Tao Q, Moore N, Roche M, & Lyle S (2010) ARRDC3 suppresses breast cancer progression by negatively regulating integrin beta4. Oncogene 29:5032-5047.
40. Nabhan J F, Pan H, & Lu Q (2010) Arrestin domain-containing protein 3 recruits the NEDD4 E3 ligase to mediate ubiquitination of the beta2-adrenergic receptor. EMBO Rep 11:605-611.
41. Chantry A (2011) WWP2 ubiquitin ligase and its isoforms: new biological insight and promising disease targets. Cell Cycle 10:2437-2439.
42. Rotin D & Kumar S (2009) Physiological functions of the HECT family of ubiquitin ligases. Nat Rev Mol Cell Biol 10:398-409.
43. Denzer K, Kleijmeer M J, Heijnen H F, Stoorvogel W, & Geuze H J (2000) Exosome: from internal vesicle of the multivesicular body to intercellular signaling device. J Cell Sci 113 Pt 19:3365-3374.
44. Komada M & Soriano P (1999) Hrs, a FYVE finger protein localized to early endosomes, is implicated in vesicular traffic and required for ventral folding morphogenesis. Genes Dev 13:1475-1485.
45. Ono A, Demirov D, & Freed E O (2000) Relationship between human immunodeficiency virus type 1 Gag multimerization and membrane binding. J Virol 74:5142-5150.
46. Fujii K, Hurley J H, & Freed E O (2007) Beyond Tsg101: the role of Alix in 'ESCRTing' HIV-1. Nat Rev Microbiol 5:912-916.
47. Wehman A M, Poggioli C, Schweinsberg P, Grant B D, & Nance J (2011) The P4-ATPase TAT-5 Inhibits the Budding of Extracellular Vesicles in C. elegans Embryos. Curr Biol 21:1951-1959.
48. Skog J, Wurdinger T, van Rijn S, Meijer D H, Gainche L, Sena-Esteves M, Curry W T, Jr., Carter B S, Krichevsky A M, & Breakefield X O (2008) Glioblastoma microvesicles transport RNA and proteins that promote tumour growth and provide diagnostic biomarkers. Nat Cell Biol 10:1470-1476.
49. Valadi H, Ekstrom K, Bossios A, Sjostrand M, Lee J J, & Lotvall J O (2007) Exosome-mediated transfer of mRNAs and microRNAs is a novel mechanism of genetic exchange between cells. Nat Cell Biol 9:654-659.

The contents of all publications, patents, websites, and database entries mentioned herein, including references 1-49 listed above, are hereby incorporated by reference in their entirety as if each individual publication, patent, website, and database entry was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment described herein may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. An arrestin domain-containing protein 1 (ARRDC1)-mediated microvesicle (ARMM), comprising
   (a) a lipid bilayer; and
      (i) an ARRDC1 protein, or fragment thereof, associated with an enzyme; or
      (ii) a TSG101 protein, or fragment thereof, associated with an enzyme.

2. The microvesicle of claim 1, wherein the enzyme is selected from the group consisting of kinases, phosphatases, ligases, recombinases, chromatin modulators, reprogramming factors, proteases, RNA editing enzymes, and nucleases.

3. The microvesicle of claim 1, wherein the enzyme is a nuclease.

4. The microvesicle of claim 3, wherein the nuclease is a zinc finger nuclease.

5. The microvesicle of claim 1, wherein the enzyme is covalently bound to the ARRDC1 protein or fragment thereof.

6. The microvesicle of claim 1, wherein the enzyme is non-covalently bound to
   (i) the ARRDC1 protein, or fragment thereof; or
   (ii) the TSG101 protein, or fragment thereof.

7. The microvesicle of claim 1, wherein the ARRDC1 protein fragment comprises an ARRDC1 PSAP domain.

8. The microvesicle of claim 1, wherein the enzyme is covalently bound to the TSG101 protein or fragment thereof.

9. The microvesicle of claim 1, wherein the microvesicle further comprises an integrin, a receptor tyrosine kinase, a G-protein coupled receptor, or a membrane-bound immunoglobulin.

10. The microvesicle of claim 1, wherein the microvesicle further comprises a protein selected from the group consisting of AHCYL2, AIP, AKR7L, AP1B1, AP1M2, C8orf30A, CASK, CNNM4, CPM, CSNK1A1, CSNK1A1L, CSNK2A1, CXADR, EFCAB4B, EIF4B, ENAH, EPB41L5, ERBB2IP, EXOC1, EXOC2, EXOC7, EXOC8, FAM102A, FAM83F, FAM84B, FERMT2, FNBP1L, GALNT7, GRB7, GRB7, ILK-2, INPP5A, IPI:IPI00328587.4, IPI:IPI00719051.3, ITCH, KIAA0174, KIAA1244, KIAA1522, KIAA1598, KIF13B, LASP1, LNPEP, LRRC1, LSS, MAPK3, MARK2, MLPH, MON2, MTOR, MTSS1, MYO10, MYO18A, NF2, NOTCH2, OCLN, PARVA, PIK3R2, PKM2, PPCS, PPID, PRKAG1, PSMC3, PTPRD, PVRL2, QARS, RAD23B, RHPN2, SH3GL1, SNTB2, SPAG1, SPINT1, SRM, STARD10, STUB1, STX16, SYTL1, TLN2, TNS3, TRIM3, TUBB2C, TWF1, USPS, VAV2, VAV3, XPOT, YARS, ZDHHC5, and ZYX.

11. The microvesicle of claim 9, wherein the microvesicle comprises an integrin selected from the group consisting of α1β1, α2β1, α4β1, α5β1, α6β1, αLβ2, αMβ2, αIIbβ3, αVβ3, αVβ5, αVβ6, and α6β4 integrins; a receptor tyrosine kinase chosen from the group consisting of an EGF receptor (ErbB family), insulin receptor, PDGF receptor, FGF receptor, VEGF receptor, HGF receptor, Trk receptor, Eph receptor, AXL receptor, LTK receptor, TIE receptor, ROR receptor, DDR receptor, RET receptor, KLG receptor, RYK receptor, and MuSK receptor; a G-protein coupled receptor chosen from the group consisting of a Rhodopsin-like receptor, Secretin receptor, metabotropic glutamate/pheromone receptor, cyclic AMP receptor, frizzled/smoothened receptor, CXCR4, CCR5, or beta-adrenergic receptor; and/or an exocyst protein chosen from EXOC7, EXOC8, EXOC1, and EXOC2.

12. The microvesicle of claim 1, wherein the enzyme is bound to
   (i) the ARRDC1 protein, or fragment thereof via a linker; or
   (ii) the TSG101 protein, or fragment thereof via a linker.

13. The microvesicle of claim 12, wherein the linker is a cleavable linker.

14. The microvesicle of claim 13, wherein the cleavable linker comprises a protease recognition site or a UV-cleavable moiety.

15. The microvesicle of 87, wherein the microvesicle diameter is from about 30 nm to about 500 nm.

16. A method of delivering an enzyme to a target cell, the method comprising contacting the target cell with the microvesicle of claim 1.

17. The method of claim 16, wherein the target cell is a human cell.

18. The method of claim 16, wherein the target cell is a stem cell.

19. The method of claim 16, wherein the target cell is a cell in a subject, and wherein the method comprises administering the microvesicle to the subject.

20. The method of claim 19, wherein the subject is a human subject.

* * * * *

UNITED STATES PATENT AND TRADEMARK OFFICE
CERTIFICATE OF CORRECTION

Page 1 of 1

PATENT NO. : 10,945,954 B2
APPLICATION NO. : 15/669720
DATED : March 16, 2021
INVENTOR(S) : Quan Lu et al.

It is certified that error appears in the above-identified patent and that said Letters Patent is hereby corrected as shown below:

In the Claims

In Claim 10, Column 74, Line 41, the text: "USPS"
Should be replaced with: -- USP5 --.

In Claim 15, Column 75, Line 1, claim dependency: "87"
Should be replaced with: -- 1 --.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 40

<210> SEQ ID NO 1
<211> LENGTH: 238
<212> TYPE: PRT
<213> ORGANISM: Aequorea victoria

<400> SEQUENCE: 1

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 2
```

```
<211> LENGTH: 433
<212> TYPE: PRT
<213> ORGANISM: Homo sapiens

<400> SEQUENCE: 2

Met Gly Arg Val Gln Leu Phe Glu Ile Ser Leu Ser His Gly Arg Val
1               5                   10                  15

Val Tyr Ser Pro Gly Glu Pro Leu Ala Gly Thr Val Arg Val Arg Leu
            20                  25                  30

Gly Ala Pro Leu Pro Phe Arg Ala Ile Arg Val Thr Cys Ile Gly Ser
        35                  40                  45

Cys Gly Val Ser Asn Lys Ala Asn Asp Thr Ala Trp Val Val Glu Glu
    50                  55                  60

Gly Tyr Phe Asn Ser Ser Leu Ser Leu Ala Asp Lys Gly Ser Leu Pro
65                  70                  75                  80

Ala Gly Glu His Ser Phe Pro Phe Gln Phe Leu Leu Pro Ala Thr Ala
                85                  90                  95

Pro Thr Ser Phe Glu Gly Pro Phe Gly Lys Ile Val Gln Val Arg
            100                 105                 110

Ala Ala Ile His Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
    130                 135                 140

Glu Gln Pro Asn Val Ala Ser Ala Thr Lys Lys Phe Ser Tyr Lys Leu
145                 150                 155                 160

Val Lys Thr Gly Ser Val Val Leu Thr Ala Ser Thr Asp Leu Arg Gly
                165                 170                 175

Tyr Val Val Gly Gln Ala Leu Gln Leu His Ala Asp Val Glu Asn Gln
            180                 185                 190

Ser Gly Lys Asp Thr Ser Pro Val Ala Ser Leu Leu Gln Lys Val
        195                 200                 205

Ser Tyr Lys Ala Lys Arg Trp Ile His Asp Val Arg Thr Ile Ala Glu
    210                 215                 220

Val Glu Gly Ala Gly Val Lys Ala Trp Arg Arg Ala Gln Trp His Glu
225                 230                 235                 240

Gln Ile Leu Val Pro Ala Leu Pro Gln Ser Ala Leu Pro Gly Cys Ser
                245                 250                 255

Leu Ile His Ile Asp Tyr Tyr Leu Gln Val Ser Leu Lys Ala Pro Glu
            260                 265                 270

Ala Thr Val Thr Leu Pro Val Phe Ile Gly Asn Ile Ala Val Asn His
        275                 280                 285

Ala Pro Val Ser Pro Arg Pro Gly Leu Gly Leu Pro Pro Gly Ala Pro
    290                 295                 300

Pro Leu Val Val Pro Ser Ala Pro Pro Gln Glu Glu Ala Glu Ala Glu
305                 310                 315                 320

Ala Ala Ala Gly Gly Pro His Phe Leu Asp Pro Val Phe Leu Ser Thr
                325                 330                 335

Lys Ser His Ser Gln Arg Gln Pro Leu Leu Ala Thr Leu Ser Ser Val
            340                 345                 350

Pro Gly Ala Pro Glu Pro Cys Pro Gln Asp Gly Ser Pro Ala Ser His
        355                 360                 365

Pro Leu His Pro Pro Leu Cys Ile Ser Thr Gly Ala Thr Val Pro Tyr
    370                 375                 380

Phe Ala Glu Gly Ser Gly Gly Pro Val Pro Thr Thr Ser Thr Leu Ile
```

```
                385                 390                 395                 400
Leu Pro Pro Glu Tyr Ser Ser Trp Gly Tyr Pro Tyr Glu Ala Pro Pro
                    405                 410                 415

Ser Tyr Glu Gln Ser Cys Gly Gly Val Glu Pro Ser Leu Thr Pro Glu
                    420                 425                 430

Ser

<210> SEQ ID NO 3
<211> LENGTH: 434
<212> TYPE: PRT
<213> ORGANISM: Mus musculus

<400> SEQUENCE: 3

Met Gly Arg Val Gln Leu Phe Glu Ile Arg Leu Ser Gln Gly Arg Val
1               5                   10                  15

Val Tyr Gly Pro Gly Glu Pro Leu Ala Gly Thr Val His Leu Arg Leu
                20                  25                  30

Gly Ala Pro Leu Pro Phe Arg Ala Ile Arg Val Thr Cys Met Gly Ser
            35                  40                  45

Cys Gly Val Ser Thr Lys Ala Asn Asp Gly Ala Trp Val Val Glu Glu
        50                  55                  60

Ser Tyr Phe Asn Ser Ser Leu Ser Leu Ala Asp Lys Gly Ser Leu Pro
65                  70                  75                  80

Ala Gly Glu His Asn Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ser Ile Asp Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
130                 135                 140

Glu Gln Pro Asn Val Ala Ser Thr Thr Lys Lys Phe Ser Tyr Lys Leu
145                 150                 155                 160

Val Lys Thr Gly Asn Val Val Leu Thr Ala Ser Thr Asp Leu Arg Gly
                165                 170                 175

Tyr Val Val Gly Gln Val Leu Arg Leu Gln Ala Asp Ile Glu Asn Gln
            180                 185                 190

Ser Gly Lys Asp Thr Ser Pro Val Val Ala Ser Leu Leu Gln Lys Val
        195                 200                 205

Ser Tyr Lys Ala Lys Arg Trp Ile Tyr Asp Val Arg Thr Ile Ala Glu
    210                 215                 220

Val Glu Gly Thr Gly Val Lys Ala Trp Arg Arg Ala Gln Trp Gln Glu
225                 230                 235                 240

Gln Ile Leu Val Pro Ala Leu Pro Gln Ser Ala Leu Pro Gly Cys Ser
                245                 250                 255

Leu Ile His Ile Asp Tyr Tyr Leu Gln Val Ser Met Lys Ala Pro Glu
            260                 265                 270

Ala Thr Val Thr Leu Pro Leu Phe Val Gly Asn Ile Ala Val Asn Gln
        275                 280                 285

Thr Pro Leu Ser Pro Cys Pro Gly Arg Glu Ser Ser Pro Gly Thr Leu
    290                 295                 300

Ser Leu Val Val Pro Ser Ala Pro Pro Gln Glu Glu Ala Glu Ala Val
305                 310                 315                 320

Ala Ser Gly Pro His Phe Ser Asp Pro Val Ser Leu Ser Thr Lys Ser
```

His Ser Gln Gln Gln Pro Leu Ser Ala Pro Leu Gly Ser Val Ser Val
            325                 330                 335

Thr Thr Thr Glu Pro Trp Val Gln Val Gly Ser Pro Ala Arg His Ser
        340                 345                 350

Leu His Pro Pro Leu Cys Ile Ser Ile Gly Ala Thr Val Pro Tyr Phe
    355                 360                 365

Ala Glu Gly Ser Ala Gly Pro Val Pro Thr Thr Ser Ala Leu Ile Leu
370                 375                 380

Pro Pro Glu Tyr Ser Ser Trp Gly Tyr Pro Tyr Glu Ala Pro Pro Ser
385                 390                 395                 400

Tyr Glu Gln Ser Cys Gly Ala Ala Gly Thr Asp Leu Gly Leu Ile Pro
        405                 410                 415

Gly Ser
    420                 425                 430

<210> SEQ ID NO 4
<211> LENGTH: 433
<212> TYPE: PRT
<213> ORGANISM: Mus musculus

<400> SEQUENCE: 4

Met Gly Arg Val Gln Leu Phe Glu Ile Arg Leu Ser Gln Gly Arg Val
1               5                   10                  15

Val Tyr Gly Pro Gly Glu Pro Leu Ala Gly Thr Val His Leu Arg Leu
            20                  25                  30

Gly Ala Pro Leu Pro Phe Arg Ala Ile Arg Val Thr Cys Met Gly Ser
        35                  40                  45

Cys Gly Val Ser Thr Lys Ala Asn Asp Gly Ala Trp Val Val Glu Glu
    50                  55                  60

Ser Tyr Phe Asn Ser Ser Leu Ser Leu Ala Asp Lys Gly Ser Leu Pro
65                  70                  75                  80

Ala Gly Glu His Asn Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ser Ile Asp Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
    130                 135                 140

Glu Gln Pro Asn Val Ala Ser Thr Thr Lys Lys Phe Ser Tyr Lys Leu
145                 150                 155                 160

Val Lys Thr Gly Asn Val Val Leu Thr Ala Ser Thr Asp Leu Arg Gly
                165                 170                 175

Tyr Val Val Gly Gln Val Leu Arg Leu Gln Ala Asp Ile Glu Asn Gln
            180                 185                 190

Ser Gly Lys Asp Thr Ser Pro Val Val Ala Ser Leu Leu Gln Val Ser
        195                 200                 205

Tyr Lys Ala Lys Arg Trp Ile Tyr Asp Val Arg Thr Ile Ala Glu Val
    210                 215                 220

Glu Gly Thr Gly Val Lys Ala Trp Arg Arg Gln Trp Gln Glu Gln
225                 230                 235                 240

Ile Leu Val Pro Ala Leu Pro Gln Ser Ala Leu Pro Gly Cys Ser Leu
                245                 250                 255

Ile His Ile Asp Tyr Tyr Leu Gln Val Ser Met Lys Ala Pro Glu Ala

-continued

```
                260                 265                 270
Thr Val Thr Leu Pro Leu Phe Val Gly Asn Ile Ala Val Asn Gln Thr
            275                 280                 285

Pro Leu Ser Pro Cys Pro Gly Arg Glu Ser Ser Pro Gly Thr Leu Ser
        290                 295                 300

Leu Val Val Pro Ser Ala Pro Pro Gln Glu Glu Ala Glu Ala Val Ala
305                 310                 315                 320

Ser Gly Pro His Phe Ser Asp Pro Val Ser Leu Ser Thr Lys Ser His
            325                 330                 335

Ser Gln Gln Gln Pro Leu Ser Ala Pro Leu Gly Ser Val Ser Val Thr
        340                 345                 350

Thr Thr Glu Pro Trp Val Gln Val Gly Ser Pro Ala Arg His Ser Leu
        355                 360                 365

His Pro Pro Leu Cys Ile Ser Ile Gly Ala Thr Val Pro Tyr Phe Ala
        370                 375                 380

Glu Gly Ser Ala Gly Pro Val Pro Thr Thr Ser Ala Leu Ile Leu Pro
385                 390                 395                 400

Pro Glu Tyr Ser Ser Trp Gly Tyr Pro Tyr Glu Ala Pro Pro Ser Tyr
            405                 410                 415

Glu Gln Ser Cys Gly Ala Ala Gly Thr Asp Leu Gly Leu Ile Pro Gly
            420                 425                 430

Ser
```

<210> SEQ ID NO 5
<211> LENGTH: 390
<212> TYPE: PRT
<213> ORGANISM: Homo sapiens

<400> SEQUENCE: 5

```
Met Ala Val Ser Glu Ser Gln Leu Lys Lys Met Val Ser Lys Tyr Lys
1               5                   10                  15

Tyr Arg Asp Leu Thr Val Arg Glu Thr Val Asn Val Ile Thr Leu Tyr
            20                  25                  30

Lys Asp Leu Lys Pro Val Leu Asp Ser Tyr Val Phe Asn Asp Gly Ser
        35                  40                  45

Ser Arg Glu Leu Met Asn Leu Thr Gly Thr Ile Pro Val Pro Tyr Arg
    50                  55                  60

Gly Asn Thr Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
            85                  90                  95

Ile Lys Thr Gly Lys His Val Asp Ala Asn Gly Lys Ile Tyr Leu Pro
        100                 105                 110

Tyr Leu His Glu Trp Lys His Pro Gln Ser Asp Leu Leu Gly Leu Ile
    115                 120                 125

Gln Val Met Ile Val Val Phe Gly Asp Glu Pro Val Phe Ser Arg
    130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
```

-continued

```
                195                 200                 205
Pro Val Thr Thr Val Gly Pro Ser Arg Asp Gly Thr Ile Ser Glu Asp
210                 215                 220
Thr Ile Arg Ala Ser Leu Ile Ser Ala Val Ser Asp Lys Leu Arg Trp
225                 230                 235                 240
Arg Met Lys Glu Glu Met Asp Arg Ala Gln Ala Glu Leu Asn Ala Leu
                245                 250                 255
Lys Arg Thr Glu Glu Asp Leu Lys Lys Gly His Gln Lys Leu Glu Glu
            260                 265                 270
Met Val Thr Arg Leu Asp Gln Glu Val Ala Glu Val Asp Lys Asn Ile
        275                 280                 285
Glu Leu Leu Lys Lys Lys Asp Glu Glu Leu Ser Ser Ala Leu Glu Lys
290                 295                 300
Met Glu Asn Gln Ser Glu Asn Asn Asp Ile Asp Glu Val Ile Ile Pro
305                 310                 315                 320
Thr Ala Pro Leu Tyr Lys Gln Ile Leu Asn Leu Tyr Ala Glu Glu Asn
                325                 330                 335
Ala Ile Glu Asp Thr Ile Phe Tyr Leu Gly Glu Ala Leu Arg Arg Gly
            340                 345                 350
Val Ile Asp Leu Asp Val Phe Leu Lys His Val Arg Leu Leu Ser Arg
        355                 360                 365
Lys Gln Phe Gln Leu Arg Ala Leu Met Gln Lys Ala Arg Lys Thr Ala
370                 375                 380
Gly Leu Ser Asp Leu Tyr
385                 390

<210> SEQ ID NO 6
<211> LENGTH: 391
<212> TYPE: PRT
<213> ORGANISM: Mus musculus

<400> SEQUENCE: 6

Met Ala Val Ser Glu Ser Gln Leu Lys Lys Met Met Ser Lys Tyr Lys
1               5                   10                  15
Tyr Arg Asp Leu Thr Val Arg Gln Thr Val Asn Val Ile Ala Met Tyr
            20                  25                  30
Lys Asp Leu Lys Pro Val Leu Asp Ser Tyr Val Phe Asn Asp Gly Ser
        35                  40                  45
Ser Arg Glu Leu Val Asn Leu Thr Gly Thr Ile Pro Val Arg Tyr Arg
    50                  55                  60
Gly Asn Ile Tyr Asn Ile Pro Ile Cys Leu Trp Leu Leu Asp Thr Tyr
65                  70                  75                  80
Pro Tyr Asn Pro Pro Ile Cys Phe Val Lys Pro Thr Ser Ser Met Thr
                85                  90                  95
Ile Lys Thr Gly Lys His Val Asp Ala Asn Gly Lys Ile Tyr Leu Pro
            100                 105                 110
Tyr Leu His Asp Trp Lys His Pro Arg Ser Glu Leu Leu Glu Leu Ile
        115                 120                 125
Gln Ile Met Ile Val Ile Phe Gly Glu Glu Pro Pro Val Phe Ser Arg
130                 135                 140
Pro Thr Val Ser Ala Ser Tyr Pro Pro Tyr Thr Ala Thr Gly Pro Pro
145                 150                 155                 160
Asn Thr Ser Tyr Met Pro Gly Met Pro Ser Gly Ile Ser Ala Tyr Pro
                165                 170                 175
```

```
Ser Gly Tyr Pro Pro Asn Pro Ser Gly Tyr Pro Gly Cys Pro Tyr Pro
            180                 185                 190

Pro Ala Gly Pro Tyr Pro Ala Thr Thr Ser Ser Gln Tyr Pro Ser Gln
            195                 200                 205

Pro Pro Val Thr Thr Val Gly Pro Ser Arg Asp Gly Thr Ile Ser Glu
            210                 215                 220

Asp Thr Ile Arg Ala Ser Leu Ile Ser Ala Val Ser Asp Lys Leu Arg
225                 230                 235                 240

Trp Arg Met Lys Glu Glu Met Asp Gly Ala Gln Ala Glu Leu Asn Ala
                245                 250                 255

Leu Lys Arg Thr Glu Glu Asp Leu Lys Lys Gly His Gln Lys Leu Glu
            260                 265                 270

Glu Met Val Thr Arg Leu Asp Gln Glu Val Ala Glu Val Asp Lys Asn
        275                 280                 285

Ile Glu Leu Leu Lys Lys Lys Asp Glu Glu Leu Ser Ser Ala Leu Glu
    290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
                325                 330                 335

Asn Ala Ile Glu Asp Thr Ile Phe Tyr Leu Gly Glu Ala Leu Arg Arg
            340                 345                 350

Gly Val Ile Asp Leu Asp Val Phe Leu Lys His Val Arg Leu Leu Ser
        355                 360                 365

Arg Lys Gln Phe Gln Leu Arg Ala Leu Met Gln Lys Ala Arg Lys Thr
    370                 375                 380

Ala Gly Leu Ser Asp Leu Tyr
385                 390

<210> SEQ ID NO 7
<211> LENGTH: 391
<212> TYPE: PRT
<213> ORGANISM: Rattus norvegicus

<400> SEQUENCE: 7

Met Ala Val Ser Glu Ser Gln Leu Lys Lys Met Met Ser Lys Tyr Lys
1               5                   10                  15

Tyr Arg Asp Leu Thr Val Arg Gln Thr Val Asn Val Ile Ala Met Tyr
            20                  25                  30

Lys Asp Leu Lys Pro Val Leu Asp Ser Tyr Val Phe Asn Asp Gly Ser
        35                  40                  45

Ser Arg Glu Leu Val Asn Leu Thr Gly Thr Ile Pro Val Arg Tyr Arg
    50                  55                  60

Gly Asn Ile Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Asp Trp Lys His Pro Arg Ser Glu Leu Leu Glu Leu Ile
        115                 120                 125

Gln Ile Met Ile Val Ile Phe Gly Glu Glu Pro Pro Val Phe Ser Arg
    130                 135                 140

Pro Thr Val Ser Ala Ser Tyr Pro Pro Tyr Thr Ala Ala Gly Pro Pro
145                 150                 155                 160
```

```
Asn Thr Ser Tyr Leu Pro Ser Met Pro Ser Gly Ile Ser Ala Tyr Pro
            165                 170                 175

Ser Gly Tyr Pro Pro Asn Pro Ser Gly Tyr Pro Gly Cys Pro Tyr Pro
            180                 185                 190

Pro Ala Gly Pro Tyr Pro Ala Thr Thr Ser Ser Gln Tyr Pro Ser Gln
            195                 200                 205

Pro Pro Val Thr Thr Ala Gly Pro Ser Arg Asp Gly Thr Ile Ser Glu
210                 215                 220

Asp Thr Ile Arg Ala Ser Leu Ile Ser Ala Val Ser Asp Lys Leu Arg
225                 230                 235                 240

Trp Arg Met Lys Glu Glu Met Asp Gly Ala Gln Ala Glu Leu Asn Ala
            245                 250                 255

Leu Lys Arg Thr Glu Glu Asp Leu Lys Lys Gly His Gln Lys Leu Glu
            260                 265                 270

Glu Met Val Thr Arg Leu Asp Gln Glu Val Ala Glu Val Asp Lys Asn
            275                 280                 285

Ile Glu Leu Leu Lys Lys Lys Asp Glu Glu Leu Ser Ser Ala Leu Glu
290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
            325                 330                 335

Asn Ala Ile Glu Asp Thr Ile Phe Tyr Leu Gly Glu Ala Leu Arg Arg
            340                 345                 350

Gly Val Ile Asp Leu Asp Val Phe Leu Lys His Val Arg Leu Leu Ser
            355                 360                 365

Arg Lys Gln Phe Gln Leu Arg Ala Leu Met Gln Lys Ala Arg Lys Thr
            370                 375                 380

Ala Gly Leu Ser Asp Leu Tyr
385                 390

<210> SEQ ID NO 8
<211> LENGTH: 10
<212> TYPE: PRT
<213> ORGANISM: Homo sapiens

<400> SEQUENCE: 8

Leu Val Val Pro Ser Ala Pro Pro Gln Glu
1               5                   10

<210> SEQ ID NO 9
<211> LENGTH: 10
<212> TYPE: PRT
<213> ORGANISM: Rattus norvegicus

<400> SEQUENCE: 9

Pro Val Val Pro Ser Ala Pro Pro Gln Glu
1               5                   10

<210> SEQ ID NO 10
<211> LENGTH: 10
<212> TYPE: PRT
<213> ORGANISM: Mus musculus

<400> SEQUENCE: 10

Leu Val Val Pro Ser Ala Pro Pro Gln Glu
1               5                   10
```

-continued

<210> SEQ ID NO 11
<211> LENGTH: 10
<212> TYPE: PRT
<213> ORGANISM: Didelphis virginiana

<400> SEQUENCE: 11

Pro Leu Val Pro Thr Ala Pro Pro Glu Asp
1               5                   10

<210> SEQ ID NO 12
<211> LENGTH: 10
<212> TYPE: PRT
<213> ORGANISM: Gallus gallus

<400> SEQUENCE: 12

Ala Val Val Pro Ser Ala Pro Pro Glu Glu
1               5                   10

<210> SEQ ID NO 13
<211> LENGTH: 10
<212> TYPE: PRT
<213> ORGANISM: Danio rerio

<400> SEQUENCE: 13

Ala Pro Ser Pro Ser Ala Pro Glu Ser Glu
1               5                   10

<210> SEQ ID NO 14
<211> LENGTH: 7
<212> TYPE: PRT
<213> ORGANISM: Homo sapiens

<400> SEQUENCE: 14

Thr Tyr Pro Phe Leu Leu Thr
1               5

<210> SEQ ID NO 15
<211> LENGTH: 7
<212> TYPE: PRT
<213> ORGANISM: Homo sapiens

<400> SEQUENCE: 15

Ala Tyr Pro Phe Thr Phe Glu
1               5

<210> SEQ ID NO 16
<211> LENGTH: 7
<212> TYPE: PRT
<213> ORGANISM: Homo sapiens

<400> SEQUENCE: 16

Ala His Pro Phe Phe Phe Thr
1               5

<210> SEQ ID NO 17
<211> LENGTH: 7
<212> TYPE: PRT
<213> ORGANISM: Homo sapiens

<400> SEQUENCE: 17

Ala Tyr Pro Phe Thr Leu Gln
1               5

<210> SEQ ID NO 18

```
<211> LENGTH: 7
<212> TYPE: PRT
<213> ORGANISM: Homo sapiens

<400> SEQUENCE: 18

Ser Phe Pro Phe Gln Phe Leu
1               5

<210> SEQ ID NO 19
<211> LENGTH: 7
<212> TYPE: PRT
<213> ORGANISM: Homo sapiens

<400> SEQUENCE: 19

Glu Tyr Ala Phe Ser Phe Glu
1               5

<210> SEQ ID NO 20
<211> LENGTH: 7
<212> TYPE: PRT
<213> ORGANISM: Homo sapiens

<400> SEQUENCE: 20

Tyr Phe His Gly Glu Pro Ile
1               5

<210> SEQ ID NO 21
<211> LENGTH: 7
<212> TYPE: PRT
<213> ORGANISM: Homo sapiens

<400> SEQUENCE: 21

Tyr Tyr His Gly Glu Pro Ile
1               5

<210> SEQ ID NO 22
<211> LENGTH: 7
<212> TYPE: PRT
<213> ORGANISM: Homo sapiens

<400> SEQUENCE: 22

Tyr Tyr His Gly Glu Pro Leu
1               5

<210> SEQ ID NO 23
<211> LENGTH: 7
<212> TYPE: PRT
<213> ORGANISM: Homo sapiens

<400> SEQUENCE: 23

His Tyr His Gly Glu Pro Ile
1               5

<210> SEQ ID NO 24
<211> LENGTH: 7
<212> TYPE: PRT
<213> ORGANISM: Homo sapiens

<400> SEQUENCE: 24

Tyr Val Val Gly Gln Ala Leu
1               5

<210> SEQ ID NO 25
<211> LENGTH: 7
<212> TYPE: PRT
```

```
<213> ORGANISM: Homo sapiens

<400> SEQUENCE: 25

Tyr Thr Pro Gly Glu Ser Ile
1               5

<210> SEQ ID NO 26
<211> LENGTH: 7
<212> TYPE: PRT
<213> ORGANISM: Homo sapiens

<400> SEQUENCE: 26

Thr Val Thr Asn Asn Thr Glu
1               5

<210> SEQ ID NO 27
<211> LENGTH: 7
<212> TYPE: PRT
<213> ORGANISM: Homo sapiens

<400> SEQUENCE: 27

His Val Thr Asn Asn Thr Asn
1               5

<210> SEQ ID NO 28
<211> LENGTH: 7
<212> TYPE: PRT
<213> ORGANISM: Homo sapiens

<400> SEQUENCE: 28

His Val Thr Asn Asn Ser Thr
1               5

<210> SEQ ID NO 29
<211> LENGTH: 7
<212> TYPE: PRT
<213> ORGANISM: Homo sapiens

<400> SEQUENCE: 29

Ser Ile Asn Asn Cys Thr Asn
1               5

<210> SEQ ID NO 30
<211> LENGTH: 7
<212> TYPE: PRT
<213> ORGANISM: Homo sapiens

<400> SEQUENCE: 30

Asp Val Glu Asn Gln Ser Gly
1               5

<210> SEQ ID NO 31
<211> LENGTH: 7
<212> TYPE: PRT
<213> ORGANISM: Homo sapiens

<400> SEQUENCE: 31

Glu Ile Glu Asn Cys Ser Ser
1               5

<210> SEQ ID NO 32
<211> LENGTH: 4
<212> TYPE: PRT
<213> ORGANISM: Artificial Sequence
<220> FEATURE:
```

<223> OTHER INFORMATION: Synthetic polypeptide

<400> SEQUENCE: 32

Pro Ala Ala Pro
1

<210> SEQ ID NO 33
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 33

Ala Gly Val Phe
1

<210> SEQ ID NO 34
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 34

Gly Phe Leu Gly
1

<210> SEQ ID NO 35
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 35

Ala Leu Ala Leu
1

<210> SEQ ID NO 36
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 36

Ala Leu Ala Leu Ala
1               5

<210> SEQ ID NO 37
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 37

Pro Ser Ala Pro
1

<210> SEQ ID NO 38
<211> LENGTH: 4
<212> TYPE: PRT
<213> ORGANISM: Artificial Sequence
<220> FEATURE:
<223> OTHER INFORMATION: Synthetic polypeptide

```
<400> SEQUENCE: 38

Pro Pro Glu Tyr
1

<210> SEQ ID NO 39
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 39

Pro Pro Ser Tyr
1

<210> SEQ ID NO 40
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 40

Pro Thr Ala Pro
1
```